United States Patent [19]

Matsui et al.

[11] Patent Number: 5,776,367
[45] Date of Patent: Jul. 7, 1998

[54] ALKENYLCYCLOHEXANE DERIVATIVES, LIQUID CRYSTAL COMPOSITION AND LIQUID CRYSTAL DISPLAY ELEMENT

[75] Inventors: Shuichi Matsui; Yasuyuki Koizumi; Takashi Kato; Kazutoshi Miyazawa; Norihisa Hachiya; Etsuo Nakagawa, all of Chiba, Japan

[73] Assignee: Chisso Corporation, Osaka, Japan

[21] Appl. No.: 666,832

[22] Filed: Jun. 19, 1996

[30] Foreign Application Priority Data

Jun. 22, 1995 [JP] Japan .................. 7-180745

[51] Int. Cl.⁶ .................. C09K 19/30; C09K 19/52; C07C 19/08
[52] U.S. Cl. .................. 252/299.63; 252/299.01; 252/299.61; 252/299.67; 570/127; 570/130; 570/131
[58] Field of Search .................. 252/299.01, 299.63, 252/299.61, 299.67; 544/242; 549/13, 369; 570/127, 130, 131; 349/182

[56] References Cited

U.S. PATENT DOCUMENTS 5,468,421  11/1995  Matsui et al. .................. 252/299.63

FOREIGN PATENT DOCUMENTS

| 0480217 | 4/1992 | European Pat. Off. . |
| 0568040 | 11/1993 | European Pat. Off. . |
| WO92/13928 | 8/1992 | WIPO . |

*Primary Examiner*—Shean C. Wu
*Attorney, Agent, or Firm*—Wenderoth, Lind & Ponack

[57] ABSTRACT

A novel liquid crystalline compound having a low viscosity and a high elastic constant ratio and at the same time, a superior compatibility with other known liquid crystalline compounds, and a liquid crystal composition and a liquid crystal display element containing the novel compound, are provided.

The compound is an alkenylcyclohexane derivative expressed by the formula (1):

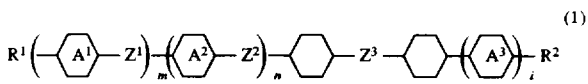

wherein $R^1$ and $R^2$ represent a linear or branched alkyl group of 1 to 15 carbon atoms or alkenyl group of 2 to 15 carbon atoms; at least one of $R^1$ and $R^2$ represents an alkenyl group; in these groups, one or more non-adjacent $CH_2$ groups may be replaced by oxygen atom, sulfur atom or $-C\equiv C-$ group; ring $A^1$, ring $A^2$ and ring $A^3$ each independently represent 1,4-cyclohexylene group wherein one or more $CH_2$ groups on the ring may be replaced by oxygen atom or sulfur atom, or 1,4-phenylene group wherein one or more CH groups on the ring may be replaced by nitrogen atom; $Z^1$ and $Z^2$ each independently represent $-CH_2CH_2-$, $-CH_2O-$, $-OCH_2-$, $-CH=CH-$, $-C\equiv C-$ or single bond; $Z^3$ represents $-(CH_2)_4-$, $-CH=CH-(CH_2)_2-$, $-CH_2-CH=CH-CH_2-$ or $-(CH_2)_2-CH=CH-$; and m, n and i each independently represent 0 or 1.

18 Claims, No Drawings

ALKENYLCYCLOHEXANE DERIVATIVES, LIQUID CRYSTAL COMPOSITION AND LIQUID CRYSTAL DISPLAY ELEMENT

BACKGRGUND OF THE INVENTION

1. Field of the Invention

This invention relates to a novel liquid crystalline compound exhibiting various preferable physical properties in liquid crystal compositions mainly for those for TN and STN, and a liquid crystal composition containing the above novel liquid crystalline compound and having various preferable physical properties.

2. Description of the Related Art

Liquid crystal display elements utilize the optical anisotropy and the dielectric anisotropy of liquid crystal substances, and have been broadly utilized for electronic calculator, word processor, television, etc. including watches, and the demand thereof is increasing year after year. Liquid crystal phase is positioned between solid phase and liquid phase, and it is roughly classified into nematic phase, smectic phase and cholesteric phase. Among them, display elements utilizing nematic phase have now been utilized most broadly. On the other hand, as to display mode, a number of modes have been so far devised, but at present, three kinds of twist-nematic (TN) mode, supertwisted nematic (STN) mode and thin film transistor (TFT) mode are becoming mainly used. Among these modes, the supertwisted nematic (STN) mode is a superior mode in general for a liquid crystal display element of a simple matrix drive, in an aspect of many characteristics such as display capacity, response speed, angle of view, tone property, etc. Further, in the case of color display, too, STN mode has been broadly popularized in the market in view of economic characteristic of being produced at a cheaper cost than TFT mode. The properties required for liquid crystal elements of such various modes are different depending upon their use applications, but it is required for any liquid crystal substances in common, to be stable to environment factors such as air, heat, light, etc.; to exhibit liquid crystal phase in a temperature range as broad as possible, around room temperature; and to have a low viscosity and a low driving voltage. However, any single liquid crystal substance simultaneously satisfying these conditions has not yet been found.

As to liquid crystal substances used for liquid crystal display elements, in order to adjust various physical properties such as dielectric anisotropy value ($\Delta\epsilon$), optical anisotropy value ($\Delta n$), viscosity, elastic constant ratio, $K_{33}/K_{11}$ ($K_{33}$: bend elastic constant; $K_{11}$: splay elastic constant), etc., to the optimum values required for individual display elements, there have been used for display elements, liquid crystal compositions having blended liquid crystalline compounds of several kinds to several tens kinds, and if necessary, non-liquid crystalline compounds of several kinds. Thus, it is required for the liquid crystal compositions to have good miscibility with other liquid crystal compounds, and also have good low temperature miscibility in view of requirement of use under various environments, recently.

In recent years, as colorization of display has advanced as well as use environments of the display has been diversified, it has been particularly required for liquid crystalline compounds to have low viscosity, high elastic constant ratio ($K_{33}/K_{11}$), broad temperature range of nematic phase and good miscibility with other liquid crystalline compounds. Use of liquid crystalline compounds having a low viscosity makes possible a high speed response of liquid crystal elements; further, a high elastic constant ratio $K_{33}/K_{11}$ makes steep the change in the transmission percentage in the vicinity of threshold voltage; and makes possible a liquid crystal display element having a high contrast. Further, a broad temperature range exhibiting nematic phase, and a superior miscibility makes possible the use of liquid crystal display elements under notable temperature change. Development of compounds having focussed on these characteristics has been vigorously made. As a result, the following compounds (a) to (d) were prepared:

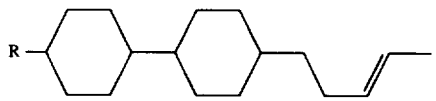

(a) Japanese patent application laid-open No. Sho 61-83136

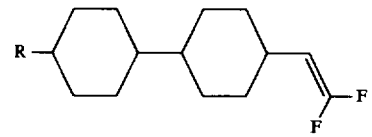

(b) Japanese patent application F 1 laid-open No. Hei 1-308239

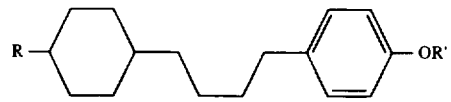

(c) Japanese patent application laid-open No. Hei 3-66632

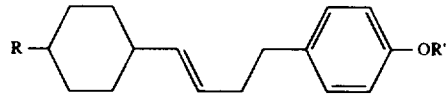

(d) Japanese patent application laid-open No. Hei 4-330019

In these formulas, R and R' each represent an alkyl group. Compound (a) (Japanese patent application laid-open No. Sho 61-83136) and compound (b) (Japanese patent application laid-open No. Hei 1-308239) have an alkenyl group or 1,1-difluorovinyl group on the side chain and a relatively high elastic constant ratio. However, due to its bicyclohexane core, it has a strong smectic property and its miscibility with other liquid crystalline compounds, particularly at low temperature, is insufficient. Further, compound (b) has a higher viscosity than that of compound (a), due to its terminal fluorine atom, to be unable to be used for liquid crystal compositions aiming at high speed response.

On the other hand, compound (c) having a cyclohexane ring and benzene ring linked with butane-1,4-diyl (Japanese patent application laid-open No. Hei 3-66632), and compound (d) having the same rings linked with butene-1,4-diyl group (Japanese patent application laid-open No. Hei 4-330019) have a relatively high elastic constant ratio, but according to the data described in the specification, smectic property is very strong, and liquid crystal compositions using them are liable to exhibit smectic phase at low temperature.

As described above, it is the present status that liquid crystal compounds satisfying the above desires have not been found, and compounds having further improved characteristics have been sought.

SUMMARY OF THE INVENTION

The object of the present invention is to provide a novel liquid crystalline compound having a low viscosity and a high elastic constant ratio and at the same time, a superior miscibility with other known liquid crystalline compounds, particularly, low temperature compatibility, and a liquid crystal composition containing the same, and further a liquid crystal display element using them.

The present inventors made extensive research in order to solve the above problems, and noted that the effect of butane-1,4-diyl group or butene-1,4-diyl group inserted as a bonding group in the prior art compounds (c) and (d) described above, has not been sufficiently exhibited, and devised a compound having a core structure having two cyclohexane rings linked with butane-1,4-diyl or butene-1, 4-diyl group and having an alkenyl group as a substituent on the cyclohexane ring, and studied its physical properties. As a result, they found that the compound not only exhibited nematic phase within a relatively broad temperature range, but also had a very low viscosity exceeding their anticipation and had a high elastic constant ratio and further, had superior miscibility with other liquid crystal compounds, particularly, low temperature miscibility. Thus the present invention has been achieved.

The present invention has the following aspects:

(1) An alkenylcyclohexane derivative expressed by the formula (1):

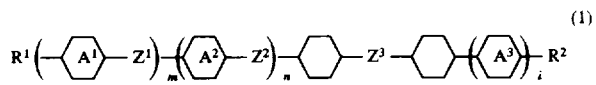

wherein $R^1$ and $R^2$ represent a linear or branched alkyl group of 1 to 15 carbon atoms or alkenyl group of 2 to 15 carbon atoms; at least one of $R^1$ and $R^2$ represents an alkenyl group; in these groups, one or more non-adjacent $CH_2$ groups may be replaced by oxygen atom, sulfur atom or —C≡C— group; ring $A^1$, ring $A^2$ and ring $A^3$ each independently represent 1,4-cyclohexylene group wherein one or more $CH_2$ groups in the ring may be replaced by oxygen atom or sulfur atom, or 1,4-phenylene group wherein one or more CH groups in the ring may be replaced by nitrogen atom; $Z^1$ and $Z^2$ each independently represent —$CH_2CH_2$—, —$CH_2O$—, —$OCH_2$—, —CH═CH—, —C≡C— or single bond; $Z^3$ represents —$(CH_2)_4$—, —CH═CH—$(CH_2)_2$—, —$CH_2$—CH═CH—$CH_2$— or —$(CH_2)_2$—CH═CH—; and m, n and i each independently represent 0 or 1.

(2) A compound according to item (1), wherein m=n=i=0 in the formula (1).

(3) A compound according to item (2), wherein, in the formula (1), $R^1$ represents an alkyl group, $R^2$ represents an alkenyl group, and $Z^3$ represents —$(CH_2)_4$—.

(4) A compound according to item (2), wherein, in the formula (1), $R^1$ represents an alkyl group, $R^2$ represents an alkenyl group and $Z^3$ represents —CH═CH—$(CH_2)_2$ or —$(CH_2)_2$—CH═CH—.

(5) A compound according to item (1), wherein in the formula (1), m=1 and n=i=0.

(6) A compound according to item (5), wherein, in the formula (1), $R^1$ represents an alkyl group, $R^2$ represents an alkenyl group and $Z^3$ represents —$(CH_2)_4$—.

(7) A compound according to item (5), wherein, in the formula (1), $R^1$ represents an alkyl group, $R^2$ represents an alkenyl group and $Z^3$ represents —CH═CH—$(CH_2)_2$— or —$(CH_2)_2$—CH═CH—.

(8) A compound according to item (1), wherein, in the formula (1), m=n=1 and i=0.

(9) A compound according to item (8), wherein, in the formula (1), $R^1$ represents an alkyl group, $R^2$ represents an alkenyl group and $Z^3$ represents —$(CH_2)_4$—.

(10) A compound according to item (8), wherein, in the formula (1), $R^1$ represents an alkyl group, $R^2$ represents an alkenyl group, and $Z^3$ represents —CH═CH—$(CH_2)_2$— or —$(CH_2)_2$—CH═CH—.

(11) A liquid crystal composition consisting of at least two components, which composition comprises at least one compound expressed by the formula (1) set forth in item (1).

(12) A liquid crystal composition which comprises as a first component, at least alkenylcyclohexane derivative according to either one of items (1) to (10), and as a second component, at least one compound selected from the group consisting of the formulas (2), (3) and (4).

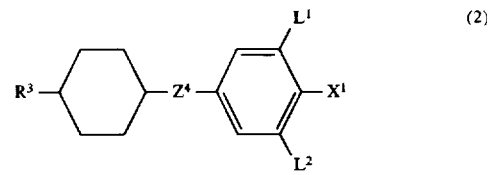

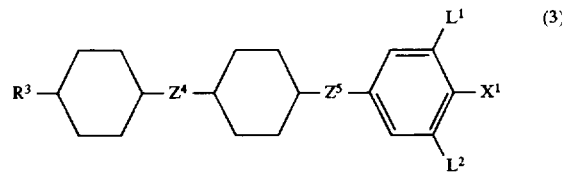

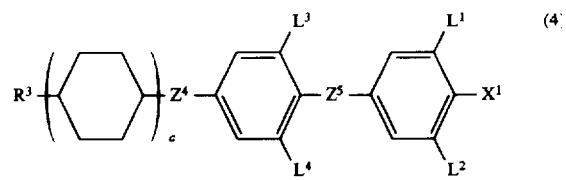

wherein $R^3$ represents an alkyl group of 1 to 10 carbon atoms; $X^1$ represents F, Cl, $OCF_3$, $OCF_2H$, $CF_3$, $CF_2H$ or $CFH_2$; $L^1$, $L^2$, $L^3$ and $L^4$ each independently represent H or F; $Z^4$ and $Z^5$ each independently represent —$(CH_2)_2$—, —CH═CH— or single bond; and a represents 1 or 2.

(13) A liquid crystal composition which comprises as a first component, at least alkenylcyclohexane derivative according to either one of items (1) to (10), and as a second component, at least one compound selected from the group consisting of the formulas (5), (6), (7), (8) and (9).

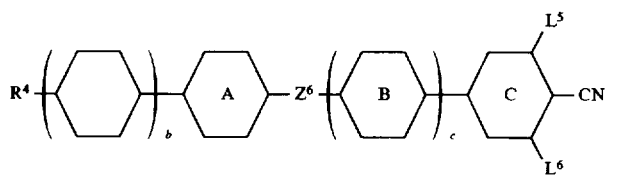
(5)

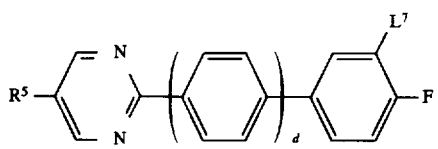
(6)

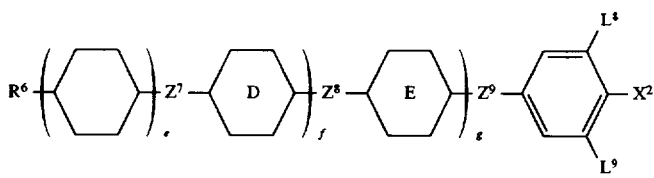
(7)

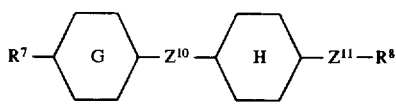
(8)

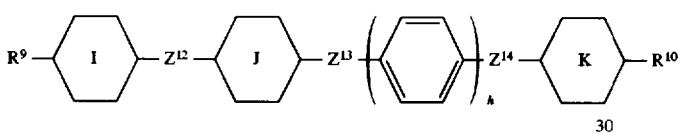
(9)

wherein $R^4$ represents fluorine atom (F), an alkyl group of 1 to 10 carbon atoms or an alkenyl group of 2 to 10 carbon atoms; in these groups, optional methylene groups (—$CH_2$—) may be replaced by oxygen atom (—O—), but two or more adjacent methylene groups are not continuously replaced by oxygen atom; ring A represents trans-1,4-cyclohexylene group, 1,4-phenylene group, pyrimidine-2,5-diyl group or 1,3-dioxane-2,5-diyl group; ring B represents trans-1,4-cyclohexylene group, 1,4-phenylene group or pyrimidine-2,5-diyl group; ring C represents trans-1,4-cyclohexylene group or 1,4-phenylene group; $Z^6$ represents —($CH_2$)$_2$—, —COO— or single bond; $L^5$ and $L^6$ each independently represent H or F; and b and c each independently represent 0 or 1;

$R^5$ represents an alkyl group of 1 to 10 carbon atoms; $L^7$ represents H or F; and d represents 0 or 1;

$R^6$ represents an alkyl group of 1 to 10 carbon atoms; ring D and ring E each independently represent trans-1,4-cyclohexylene group or 1,4-phenylene group; $Z^7$ and $Z^8$ each independently represent —COO— or single bond; $Z^9$ represents —COO— or —C≡C—; $L^8$ and $L^9$ each independently represent H or F; $X^2$ represents F, $OCF_3$, $OCF_2H$, $CF_3$, $CF_2H$ or $CFH_2$, but when $X^2$ represents $OCF_3$, $OCF_2H$, $CF_3$, $CF_2H$ or $CFH_2$, $L^8$ and $L^9$ both represent H; e, f and g each independently represent 0 or 1;

$R^7$ and $R^8$ each independently represent an alkyl group of 1 to 10 carbon atoms or an alkenyl group of 2 to 10 carbon atoms, and in either, optional methylene groups (—$CH_2$—) among them may be replaced by oxygen atom (—O—), but two or more methylene groups are not continuously replaced by oxygen atom; ring G represents trans-1,4-cyclohexylene group, 1,4-phenylene group or pyrimidine-2,5-diyl; ring H represents trans-1,4-cyclohexylene group or 1,4-phenylene group; $Z^{10}$ represents —C≡C—, —COO—, —($CH_2$)$_2$—, —CH=CH—C≡C— or single bond; $Z^{11}$ represents —COO— or single bond;

$R^9$ and $R^{10}$ each independently represent an alkyl group of 1 to 10 carbon atoms or an alkenyl group of 2 to 10 carbon atoms, and in either, optional methylene groups (—$CH_2$—) among them may be replaced by oxygen atom (—O—), but two or more methylene groups are not continuously replaced by oxygen atom; ring I represents trans-1,4-cyclohexylene group, 1,4-phenylene group or pyrimidine-2,5-diyl group; ring J represents trans-1,4-cyclohexylene group, 1,4-phenylene group wherein one or more hydrogen atoms on the ring may be replaced by F, or pyrimidine-2,5-diyl group; ring K represents trans-1,4-cyclohexylene group or 1,4-phenylene group; $Z^{12}$ and $Z^{14}$ each independently represent —COO—, —($CH_2$)$_2$— or single bond; $Z^{13}$ represents —CH=CH—, —C≡C—, —COO— or single bond; and h represents 0 or 1.

(14) A liquid crystal composition which comprises as a first component, at least one alkenylcyclohexane derivative according to either one of items (1) to (10), and as a part of a second component, at least one compound selected from the group consisting of the formulas (2), (3) and (4), and further as another part of the second component, at least one compound selected from the group consisting of the formulas (5), (6), (7), (8) and (9).

(15) A liquid crystal display element constituted by using a liquid crystal composition according to either one of items (11) to (14).

DETAILED DESCRIPTION OF THE INVENTION

Preferable embodiments of the alkenylcyclohexane derivative expressed by the formula (1) in the first aspect of the present invention are compounds expressed by the following groups of (1-a) to (1-o):

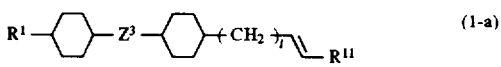
(1-a)

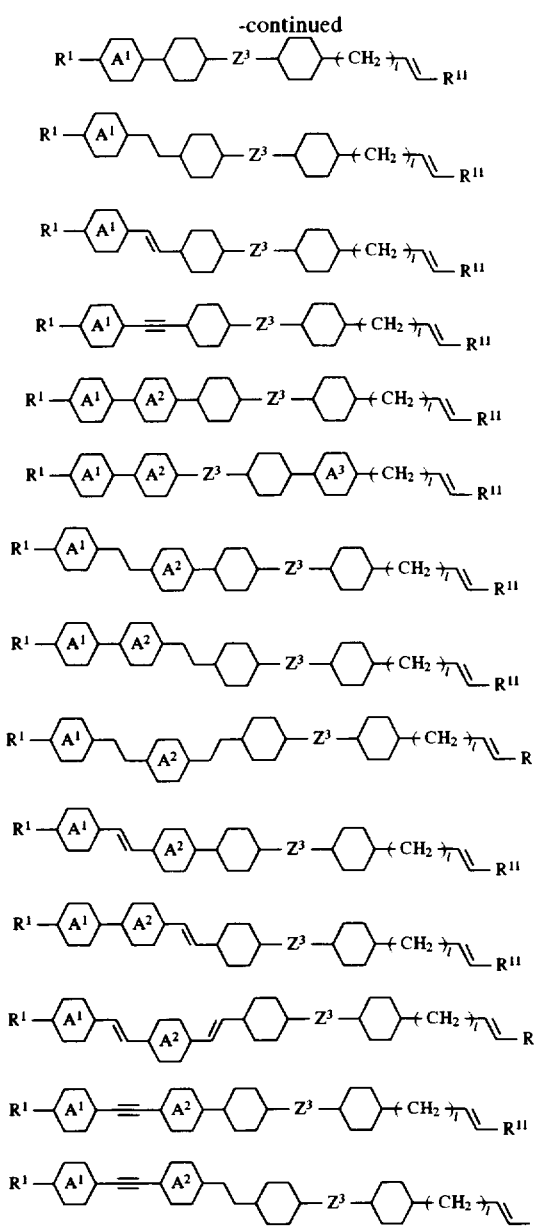

In these formulas, rings $A^1$, $A^2$, $A^3$, $R^1$ and $Z^3$ are as defined above. $R^{11}$ represents hydrogen atom or a linear or branched alkyl group of 1 to 13 carbon atoms and l represents an integer of 0 to 6.

In addition, in compounds expressed by the formulas (1-a) to (1-o), as an alkenyl group corresponding to $R^2$ in the formula (1), 1E-alkenyl, 2Z-alkenyl, 3E-alkenyl and 4-alkenyl group are preferred, and concretely, 1-ethenyl, 1E-propenyl, 1E-butenyl, 1E-pentenyl, 1E-hexenyl, 2Z-propenyl, 2-propenyl, 2Z-butenyl, 2Z-pentenyl, 2Z-hexenyl, 3-butenyl, 3E-pentenyl and 3E-hexenyl group are preferred.

Any of compounds expressed by the group of the formulas (1-a) to (1-o) have a very low viscosity and exhibit a high elastic constant ratio ($K_{33}/K_{11}$). Among them, the bicyclic and tricyclic compounds expressed by the formulas (1-a) to (1-e) have a very low viscosity, and when the compounds are added as a component of a liquid crystal composition, it is possible to notably reduce the viscosity without reducing the clearing point of the liquid crystal composition. Further, tetracyclic compounds expressed by the formulas (1-f) to (1-o) have a broad nematic phase temperature range, and when the compounds are added as a component of a liquid crystal composition, it is possible to elevate the clearing point without increasing the viscosity.

Further, any of compounds expressed by the group of the formulas (1-a) to (1-o) wherein $R^1$ represents an alkenyl group and $Z^3$ represents butene-1,4-diyl group, exhibit a very high elastic constant ratio ($K_{33}/K_{11}$) and have a characteristic of exhibiting a notably low viscosity and a high clearing point, as compared with saturated type compounds having the same core.

As described above, the compound of the present invention has superior characteristics, and when the compound of the present invention is used, it is possible to provide a liquid crystal composition and a liquid crystal display element having more improved characteristics.

As concrete examples of alkenylcyclohexane derivatives of the group of the formulas (1-a) to (1-o), the following compounds of Nos. 1 to 516 can be listed:

| No | $R^1-$ | $A^1$ | $-Z^1-$ | $A^2$ | $-Z^2-$ | $-Z^3-$ | $A^3$ | $-R^2$ |
|---|---|---|---|---|---|---|---|---|
| 1 | $CH_3$ | | | | | ⌐⌐ | | ⟍ |
| 2 | $C_2H_5$ | | | | | ⌐⌐ | | ⟍ |
| 3 | $C_3H_7$ | | | | | ⌐⌐ | | ⟍ |
| 4 | $C_4H_9$ | | | | | ⌐⌐ | | ⟍ |

-continued

| No | R¹— | —⬡A¹— | —Z¹— | —⬡A²— | —Z²— | —Z³— | —⬡A³— | —R² |
|---|---|---|---|---|---|---|---|---|
| 5 | C₅H₁₁ | | | | | ⌴ | | ⫽ |
| 6 | C₇H₁₅ | | | | | ⌴ | | ⫽ |
| 7 | CH₃ | | | | | ⌴ | | ⫽ |
| 8 | C₂H₅ | | | | | ⌴ | | ⫽ |
| 9 | C₃H₇ | | | | | ⌴ | | ⫽ |
| 10 | C₅H₁₁ | | | | | ⌴ | | ⫽ |
| 11 | C₇H₁₅ | | | | | ⌴ | | ⫽ |
| 12 | CH₃ | | | | | ⌴ | | ⫽ |
| 13 | C₂H₅ | | | | | ⌴ | | ⫽ |
| 14 | C₃H₇ | | | | | ⌴ | | ⫽ |
| 15 | C₅H₁₁ | | | | | ⌴ | | ⫽ |
| 16 | C₇H₁₅ | | | | | ⌴ | | ⫽ |
| 17 | CH₃ | | | | | ⌴ | | ⫽ |
| 18 | C₂H₅ | | | | | ⌴ | | ⫽ |
| 19 | C₃H₇ | | | | | ⌴ | | ⫽ |
| 20 | C₅H₁₁ | | | | | ⌴ | | ⫽ |
| 21 | C₇H₁₅ | | | | | ⌴ | | ⫽ |
| 22 | CH₃ | | | | | ⌴ | | ⫽ |
| 23 | C₂H₅ | | | | | ⌴ | | ⫽ |
| 24 | C₃H₇ | | | | | ⌴ | | ⫽ |
| 25 | C₅H₁₁ | | | | | ⌴ | | ⫽ |
| 26 | C₇H₁₅ | | | | | ⌴ | | ⫽ |
| 27 | CH₃ | | | | | ⌴ | | ⫽ |

-continued
| No | R¹— | —⬡A¹— | —Z¹— | —⬡A²— | —Z²— | —Z³— | —⬡A³— | —R² |
|---|---|---|---|---|---|---|---|---|
| 28 | C₂H₅ | | | | |  | | 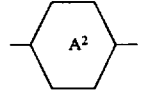 |
| 29 | C₃H₇ | | | | | 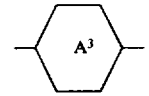 | | 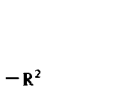 |
| 30 | C₅H₁₁ | | | | |  | |  |
| 31 | C₇H₁₅ | | | | | 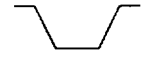 | | 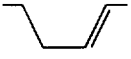 |
| 32 | CH₃ | | | | |  | | 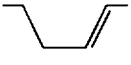 |
| 33 | C₂H₅ | | | | | 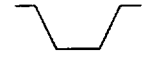 | | 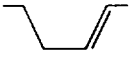 |
| 34 | C₃H₇ | | | | | 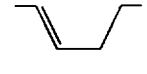 | |  |
| 35 | C₅H₁₁ | | | | | 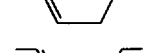 | |  |
| 36 | C₇H₁₅ | | | | | 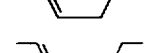 | |  |
| 37 | CH₃ | | | | | 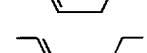 | |  |
| 38 | C₂H₅ | | | | | 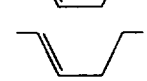 | |  |
| 39 | C₃H₇ | | | | |  | |  |
| 40 | C₅H₁₁ | | | | |  | |  |
| 41 | C₇H₁₅ | | | | |  | |  |
| 42 | CH₃ | | | | |  | |  |
| 43 | C₂H₅ | | | | |  | |  |
| 44 | C₃H₇ | | | | | 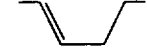 | |  |
| 45 | C₅H₁₁ | | | | | 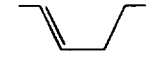 | |  |
| 46 | C₇H₁₅ | | | | | 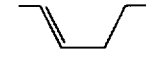 | | 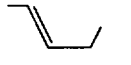 |
| 47 | CH₃ | | | | | 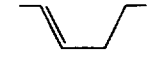 | | 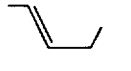 |
| 48 | C₂H₅ | | | | | 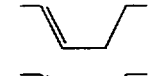 | | 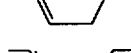 |
| 49 | C₃H₇ | | | | | 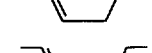 | | 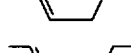 |
| 50 | C₅H₁₁ | | | | | 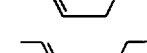 | | 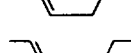 |

| No | R¹— | —A¹— | —Z¹— | —A²— | —Z²— | —Z³— | —A³— | —R² |
|---|---|---|---|---|---|---|---|---|
| 51 | $C_7H_{15}$ | | | | | 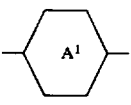 | | 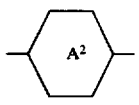 |
| 52 | $CH_3$ | | | | | 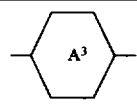 | |  |
| 53 | $C_2H_5$ | | | | |  | |  |
| 54 | $C_3H_7$ | | | | |  | |  |
| 55 | $C_5H_{11}$ | | | | |  | |  |
| 56 | $C_7H_{15}$ | | | | |  | |  |
| 57 | $CH_3$ | | | | |  | |  |
| 58 | $C_2H_5$ | | | | |  | |  |
| 59 | $C_3H_7$ | | | | |  | | 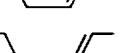 |
| 60 | $C_5H_{11}$ | | | | |  | | 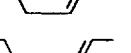 |
| 61 | $C_7H_{15}$ | | | | | 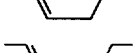 | | 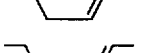 |
| 62 | $CH_3$ | | | | | 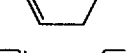 | | 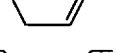 |
| 63 | $C_2H_5$ | | | | | 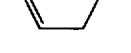 | | 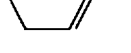 |
| 64 | $C_3H_7$ | | | | | 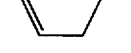 | | 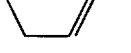 |
| 65 | $C_5H_{11}$ | | | | |  | |  |
| 66 | $C_7H_{15}$ | | | | |  | |  |
| 67 | $CH_3$ | | | | |  | |  |
| 68 | $C_2H_5$ | | | | |  | |  |
| 69 | $C_3H_7$ | | | | |  | |  |
| 70 | $C_5H_{11}$ | | | | |  | |  |
| 71 | $C_7H_{15}$ | | | | |  | |  |
| 72 | $CH_3$ | | | | | 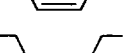 | |  |
| 73 | $C_2H_5$ | | | | | 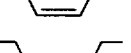 | |  |

| No | R¹− | ⬡ A¹ | −Z¹− | ⬡ A² | −Z²− | −Z³− | ⬡ A³ | −R² |
|---|---|---|---|---|---|---|---|---|
| 74 | C₃H₇ | | | | | 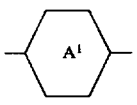 | | 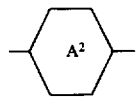 |
| 75 | C₅H₁₁ | | | | | 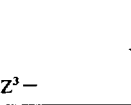 | |  |
| 76 | C₇H₁₅ | | | | |  | |  |
| 77 | CH₃ | | | | |  | |  |
| 78 | C₂H₅ | | | | |  | |  |
| 79 | C₃H₇ | | | | |  | |  |
| 80 | C₅H₁₁ | | | | |  | |  |
| 81 | C₇H₁₅ | | | | | 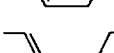 | | 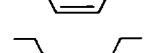 |
| 82 | CH₃ | | | | | 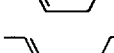 | | 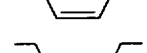 |
| 83 | C₂H₅ | | | | | 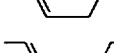 | | 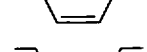 |
| 84 | C₃H₇ | | | | | 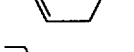 | | 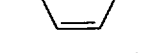 |
| 85 | C₅H₁₁ | | | | | 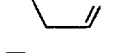 | |  |
| 86 | C₇H₁₅ | | | | | 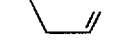 | |  |
| 87 | CH₃ | | | | |  | |  |
| 88 | C₂H₅ | | | | | 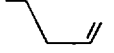 | |  |
| 89 | C₃H₇ | | | | |  | |  |
| 90 | C₅H₁₁ | | | | |  | |  |
| 91 | C₇H₁₅ | | | | |  | |  |
| 92 | CH₃ | | | | |  | | 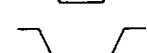 |
| 93 | C₂H₅ | | | | |  | | 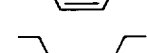 |
| 94 | C₃H₇ | | | | | 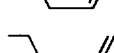 | | 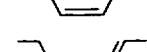 |
| 95 | C₅H₁₁ | | | | | 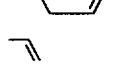 | | 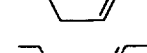 |
| 96 | C₇H₁₅ | | | | |  | | 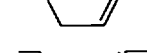 |

5,776,367

-continued

| No | R¹— | —A¹— | —Z¹— | —A²— | —Z²— | —Z³— | —A³— | —R² |
|---|---|---|---|---|---|---|---|---|
| 97 | CH₃ | | | | | | | |
| 98 | C₂H₅ | | | | | | | |
| 99 | C₃H₇ | | | | | | | |
| 100 | C₅H₁₁ | | | | | | | |
| 101 | C₇H₁₅ | | | | | | | |
| 102 | CH₃ | | | | | | | |
| 103 | C₂H₅ | | | | | | | |
| 104 | C₃H₇ | | | | | | | |
| 105 | C₅H₁₁ | | | | | | | |
| 106 | C₇H₁₅ | | | | | | | |
| 107 | CH₃ | | | | | | | |
| 108 | C₂H₅ | | | | | | | |
| 109 | C₃H₇ | | | | | | | |
| 110 | C₅H₁₁ | | | | | | | |
| 111 | C₇H₁₅ | | | | | | | |
| 112 | CH₃ | | | | | | | |
| 113 | C₂H₅ | | | | | | | |
| 114 | C₃H₇ | | | | | | | |
| 115 | C₅H₁₁ | | | | | | | |
| 116 | C₇H₁₅ | | | | | | | |
| 117 | CH₃ | | | | | | | |
| 118 | C₂H₅ | | | | | | | |
| 119 | C₃H₇ | | | | | | | |

-continued
| No | R¹— | —A¹— | —Z¹— | —A²— | —Z²— | —Z³— | —A³— | —R² |
|----|-----|------|------|------|------|------|------|------|
| 120 | C₅H₁₁ | | | | | 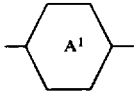 | | 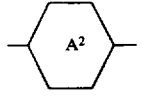 |
| 121 | C₇H₁₅ | | | | | 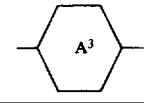 | | 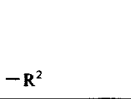 |
| 122 | 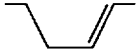 | | | | |  | |  |
| 123 |  | | | | |  | |  |
| 124 |  | | | | |  | |  |
| 125 |  | | | | |  | |  |
| 126 |  | | | | |  | |  |
| 127 |  | | | | |  | | 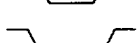 |
| 128 | 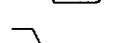 | | | | |  | |  |
| 129 | 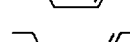 | | | | | 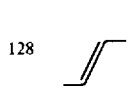 | | 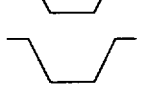 |
| 130 | 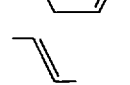 | | | | | 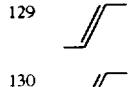 | | 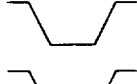 |
| 131 | 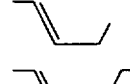 | | | | | 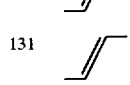 | |  |
| 132 |  | | | | | 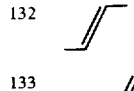 | | 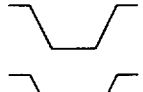 |
| 133 | 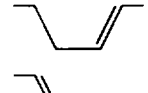 | | | | | 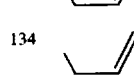 | |  |
| 134 | 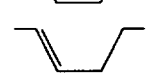 | | | | |  | |  |
| 135 |  | | | | |  | |  |
| 136 |  | | | | |  | |  |
| 137 |  | | | | |  | |  |
| 138 |  | | | | |  | |  |
| 139 |  | | | | |  | |  |
| 140 |  | | | | |  | |  |
| 141 |  | | | | | 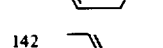 | | 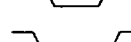 |
| 142 | 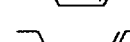 | | | | |  | | 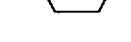 |

-continued

| No | R¹- | A¹ | -Z¹- | A² | -Z²- | -Z³- | A³ | -R² |
|---|---|---|---|---|---|---|---|---|
| 143 | | | | | | | | |
| 144 | | | | | | | | |
| 145 | | | | | | | | |
| 146 | | | | | | | | |
| 147 | | | | | | | | |
| 148 | | | | | | | | |
| 149 | | | | | | | | |
| 150 | | | | | | | | |
| 151 | | | | | | | | |
| 152 | | | | | | | | |
| 153 | | | | | | | | |
| 154 | | | | | | | | |
| 155 | | | | | | | | |
| 156 | | | | | | | | |
| 157 | | | | | | | | |
| 158 | | | | | | | | |
| 159 | | | | | | | | |
| 160 | | | | | | | | |
| 161 | | | | | | | | |
| 162 | | | | | | | | |
| 163 | | | | | | | | |
| 164 | -O | | | | | | | |
| 165 | -O | | | | | | | |

| No | R¹– | A¹ | –Z¹– | A² | –Z²– | –Z³– | A³ | –R² |
|---|---|---|---|---|---|---|---|---|
| 166 |  | | | | | 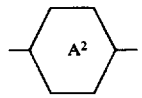 | | 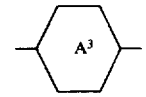 |
| 167 |  | | | | | 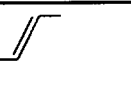 | |  |
| 168 |  | | | | |  | | 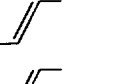 |
| 169 |  | | | | |  | |  |
| 170 | 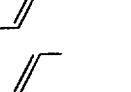 | | | | |  | |  |
| 171 |  | | | | |  | |  |
| 172 |  | | | | |  | |  |
| 173 |  | | | | |  | |  |
| 174 | 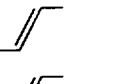 | | | | |  | |  |
| 175 |  | | | | | 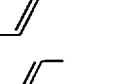 | |  |
| 176 |  | | | | |  | | 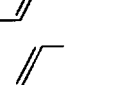 |
| 177 |  | | | | |  | |  |
| 178 | 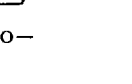 | | | | |  | |  |
| 179 |  | | | | |  | |  |
| 180 |  | | | | |  | |  |
| 181 |  | | | | |  | |  |
| 182 |  | | | | |  | |  |
| 183 |  | | | | |  | |  |
| 184 |  | | | | |  | |  |
| 185 |  | | | | |  | |  |
| 186 |  | | | | |  | |  |
| 187 |  | | | | |  | |  |
| 188 |  | | | | |  | |  |

| No | R¹– | –A¹– | –Z¹– | –A²– | –Z²– | –Z³– | –A³– | –R² |
|---|---|---|---|---|---|---|---|---|
| 189 | CH₂=CH-CH₂-O– | | | | | (cyclohexyl) | | vinyl |
| 190 | CH₂=CH-CH₂-O– | | | | | (cyclohexyl) | | allyl |
| 191 | CH₂=CH-CH₂-O– | | | | | (cyclohexyl) | | 1-butenyl |
| 192 | CH₂=CH-CH₂-O– | | | | | (cyclohexyl) | | 3-butenyl |
| 193 | CH₂=CH-CH₂-O– | | | | | (cyclohexyl) | | 2-pentenyl |
| 194 | CH₂=CH-CH₂-O– | | | | | (cyclohexyl) | | vinyl |
| 195 | CH₂=CH-CH₂-O– | | | | | (cyclohexyl) | | allyl |
| 196 | CH₂=CH-CH₂-O– | | | | | (cyclohexyl) | | allyl |
| 197 | CH₂=CH-CH₂-O– | | | | | (cyclohexyl) | | 1-butenyl |
| 198 | CH₂=CH-CH₂-O– | | | | | (cyclohexyl) | | 3-butenyl |
| 199 | CH₂=CH-CH₂-O– | | | | | (cyclohexyl) | | 2-pentenyl |
| 200 | C₂H₅ | (cyclohexyl) | | | | (cyclohexyl) | | vinyl |
| 201 | C₃H₇ | (cyclohexyl) | | | | (cyclohexyl) | | vinyl |
| 202 | C₅H₁₁ | (cyclohexyl) | | | | (cyclohexyl) | | vinyl |
| 203 | C₂H₅ | (cyclohexyl) | | | | (cyclohexyl) | | allyl |
| 204 | C₃H₇ | (cyclohexyl) | | | | (cyclohexyl) | | allyl |
| 205 | C₅H₁₁ | (cyclohexyl) | | | | (cyclohexyl) | | allyl |
| 206 | C₂H₅ | (cyclohexyl) | | | | (cyclohexyl) | | 1-butenyl |

| No | R¹— | A¹ | —Z¹— | A² | —Z²— | —Z³— | A³ | —R² |
|----|-----|----|----|----|----|----|----|----|
| 207 | C₃H₇ |  | | | | 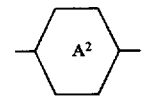 | | 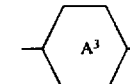 |
| 208 | C₅H₁₁ | 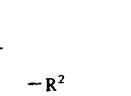 | | | | 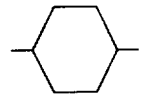 | |  |
| 209 | C₂H₅ |  | | | | 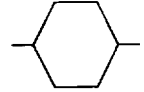 | | 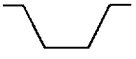 |
| 210 | C₃H₇ | 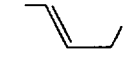 | | | | 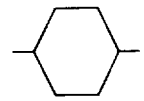 | |  |
| 211 | C₅H₁₁ | 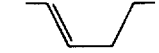 | | | | 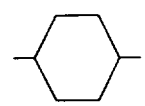 | |  |
| 212 | C₂H₅ |  | | | | 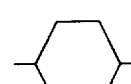 | |  |
| 213 | C₃H₇ | 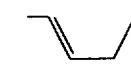 | | | | 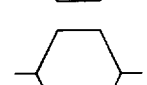 | |  |
| 214 | C₅H₁₁ | 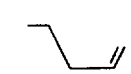 | | | | 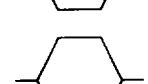 | |  |
| 215 | C₂H₅ | 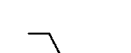 | | | | 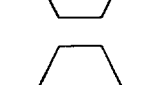 | |  |
| 216 | C₃H₇ | 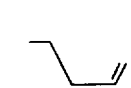 | | | | 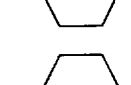 | |  |
| 217 | C₅H₁₁ |  | | | | 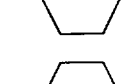 | |  |
| 218 | C₂H₅ |  | | | |  | |  |
| 219 | C₃H₇ |  | | | | 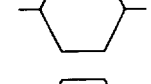 | | 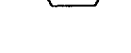 |
| 220 | C₅H₁₁ | 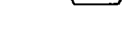 | | | | 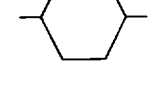 | | 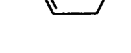 |

| No | R¹— | —A¹— | —Z¹— | —A²— | —Z²— | —Z³— | —A³— | —R² |
|---|---|---|---|---|---|---|---|---|
| 221 | C₂H₅ | cyclohexane | | | | CH=CH | | CH=CH- |
| 222 | C₃H₇ | cyclohexane | | | | CH=CH | | CH=CH- |
| 223 | C₅H₁₁ | cyclohexane | | | | CH=CH | | CH=CH- |
| 224 | C₂H₅ | cyclohexane | | | | CH=CH | | -CH=CH |
| 225 | C₃H₇ | cyclohexane | | | | CH=CH | | -CH=CH |
| 226 | C₅H₁₁ | cyclohexane | | | | CH=CH | | -CH=CH |
| 227 | C₂H₅ | cyclohexane | | | | CH=CH | | CH=CH |
| 228 | C₃H₇ | cyclohexane | | | | CH=CH | | CH=CH |
| 229 | C₅H₁₁ | cyclohexane | | | | CH=CH | | CH=CH |
| 230 | C₂H₅ | cyclohexane | | | | CH=CH | | C=CH₂ |
| 231 | C₃H₇ | cyclohexane | | | | CH=CH | | C=CH₂ |
| 232 | C₅H₁₁ | cyclohexane | | | | CH=CH | | C=CH₂ |
| 233 | C₂H₅ | cyclohexane | | | | CH=CH | | CH₂-CH=CH |
| 234 | C₃H₇ | cyclohexane | | | | CH=CH | | CH₂-CH=CH |

5,776,367

-continued

| No | R¹— | A¹ | —Z¹— | A² | —Z²— | —Z³— | A³ | —R² |
|---|---|---|---|---|---|---|---|---|
| 235 | $C_5H_{11}$ | cyclohexyl | | | | CH=CH | | CH=CH |
| 236 | $C_2H_5$ | cyclohexyl | | | | CH=CH | | C=C |
| 237 | $C_3H_7$ | cyclohexyl | | | | CH=CH | | C=C |
| 238 | $C_5H_{11}$ | cyclohexyl | | | | CH=CH | | C=C |
| 239 | $C_2H_5$ | cyclohexyl | | | | CH=CH | | CH=CH |
| 240 | $C_3H_7$ | cyclohexyl | | | | CH=CH | | CH=CH |
| 241 | $C_5H_{11}$ | cyclohexyl | | | | CH=CH | | CH=CH |
| 242 | $C_2H_5$ | cyclohexyl | | | | CH=CH | | CH=CH |
| 243 | $C_3H_7$ | cyclohexyl | | | | CH=CH | | CH=CH |
| 244 | $C_5H_{11}$ | cyclohexyl | | | | CH=CH | | CH=CH |
| 245 | $C_2H_5$ | cyclohexyl | | | | CH=CH | | CH=CH |
| 246 | $C_3H_7$ | cyclohexyl | | | | CH=CH | | CH=CH |
| 247 | $C_5H_{11}$ | cyclohexyl | | | | CH=CH | | CH=CH |
| 248 | $C_2H_5$ | cyclohexyl | | | | CH=CH | | CH=C |

| No | R¹— | A¹ | —Z¹— | A² | —Z²— | —Z³— | A³ | —R² |
|---|---|---|---|---|---|---|---|---|
| 249 | C₃H₇ | cyclohexyl | | | | CH=CH | | CH₂-CH=CH₂ |
| 250 | C₅H₁₁ | cyclohexyl | | | | CH=CH | | CH₂-CH=CH₂ |
| 251 | C₂H₅ | cyclohexyl | | | | CH=CH | | CH=CH-CH₃ |
| 252 | C₃H₇ | cyclohexyl | | | | CH=CH | | CH=CH-CH₃ |
| 253 | C₅H₁₁ | cyclohexyl | | | | CH=CH | | CH=CH-CH₃ |
| 254 | C₂H₅ | phenyl | | | | CH=CH | | CH=CH₂ |
| 255 | C₃H₇ | phenyl | | | | CH=CH | | CH=CH₂ |
| 256 | C₅H₁₁ | phenyl | | | | CH=CH | | CH=CH₂ |
| 257 | C₂H₅ | phenyl | | | | CH=CH | | CH=CH-CH₃ |
| 258 | C₃H₇ | phenyl | | | | CH=CH | | CH=CH-CH₃ |
| 259 | C₅H₁₁ | phenyl | | | | CH=CH | | CH=CH-CH₃ |
| 260 | C₂H₅ | phenyl | | | | CH=CH | | CH₂-CH=CH₂ |
| 261 | C₃H₇ | phenyl | | | | CH=CH | | CH₂-CH=CH₂ |
| 262 | C₅H₁₁ | phenyl | | | | CH=CH | | CH₂-CH=CH₂ |

-continued
| No | R¹— | —A¹— | —Z¹— | —A²— | —Z²— | —Z³— | —A³— | —R² |
|---|---|---|---|---|---|---|---|---|
| 263 | C₂H₅ |  | | | | 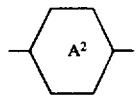 | |  |
| 264 | C₃H₇ |  | | | |  | | 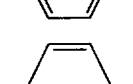 |
| 265 | C₅H₁₁ | 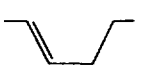 | | | | 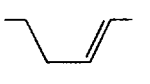 | |  |
| 266 | C₂H₅ | 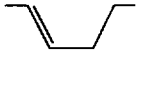 | | | | 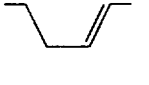 | | 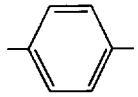 |
| 267 | C₃H₇ | 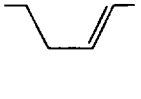 | | | |  | | 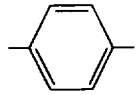 |
| 268 | C₅H₁₁ | 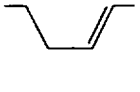 | | | |  | | 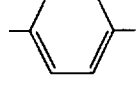 |
| 269 | C₂H₅ | 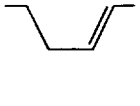 | | | |  | | 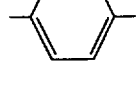 |
| 270 | C₃H₇ | 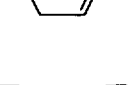 | | | | 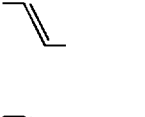 | | 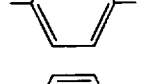 |
| 271 | C₅H₁₁ |  | | | |  | | 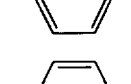 |
| 272 | C₂H₅ | 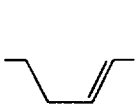 | | | | 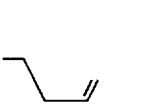 | | 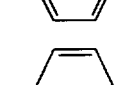 |
| 273 | C₃H₇ |  | | | |  | | 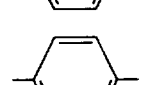 |
| 274 | C₅H₁₁ |  | | | | 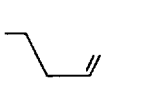 | | 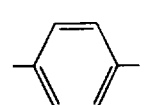 |
| 275 | C₂H₅ |  | | | |  | | 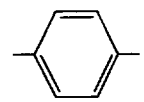 |
| 276 | C₃H₇ |  | | | |  | |  |

| No | R¹— | —A¹— | —Z¹— | —A²— | —Z²— | —Z³— | —A³— | —R² |
|---|---|---|---|---|---|---|---|---|
| 277 | C₅H₁₁ | phenyl | | | | alkenyl | | alkenyl |
| 278 | C₂H₅ | cyclohexyl | CH₂ | | | alkyl | | alkenyl |
| 279 | C₃H₇ | cyclohexyl | CH₂ | | | alkyl | | alkenyl |
| 280 | C₂H₅ | cyclohexyl | CH₂ | | | alkyl | | alkenyl |
| 281 | C₃H₇ | cyclohexyl | CH₂ | | | alkyl | | alkenyl |
| 282 | C₂H₅ | cyclohexyl | CH₂ | | | alkyl | | alkenyl |
| 283 | C₃H₇ | cyclohexyl | CH₂ | | | alkyl | | alkenyl |
| 282 | C₂H₅ | cyclohexyl | CH₂ | | | alkyl | | alkenyl |
| 283 | C₃H₇ | cyclohexyl | CH₂ | | | alkyl | | alkenyl |
| 284 | C₂H₅ | cyclohexyl | CH₂ | | | alkenyl | | alkenyl |
| 285 | C₃H₇ | cyclohexyl | CH₂ | | | alkenyl | | alkenyl |
| 286 | C₂H₅ | cyclohexyl | CH₂ | | | alkenyl | | alkenyl |
| 287 | C₃H₇ | cyclohexyl | CH₂ | | | alkenyl | | alkenyl |
| 288 | C₂H₅ | cyclohexyl | CH₂ | | | alkenyl | | alkenyl |

| No | R¹— | —A¹— | —Z¹— | —A²— | —Z²— | —Z³— | —A³— | —R² |
|---|---|---|---|---|---|---|---|---|
| 289 | C₃H₇ | | | | | | | |
| 290 | C₂H₅ | | | | | | | |
| 291 | C₃H₇ | | | | | | | |
| 292 | C₂H₅ | | | | | | | |
| 293 | C₃H₇ | | | | | | | |
| 294 | C₂H₅ | | | | | | | |
| 295 | C₃H₇ | | | | | | | |
| 296 | C₂H₅ | | | | | | | |
| 297 | C₃H₇ | | | | | | | |
| 298 | C₂H₅ | | | | | | | |
| 299 | C₃H₇ | | | | | | | |
| 300 | C₂H₅ | | | | | | | |
| 301 | C₃H₇ | | | | | | | |
| 302 | C₂H₅ | | | | | | | |

-continued
| No | R¹− | ─A¹─ | −Z¹− | ─A²─ | −Z²− | −Z³− | ─A³─ | −R² |
|----|-----|------|------|------|------|------|------|-----|
| 303 | C₃H₇ |  | 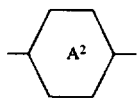 | | | 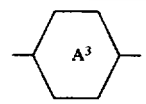 | | 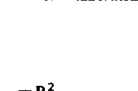 |
| 304 | C₂H₅ |  |  | | |  | |  |
| 305 | C₃H₇ |  |  | | | 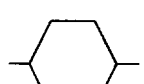 | |  |
| 306 | C₂H₅ | 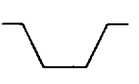 | 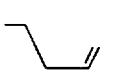 | | | 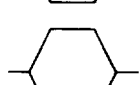 | |  |
| 307 | C₃H₇ | 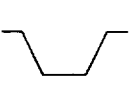 | 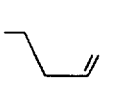 | | | 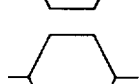 | |  |
| 308 | C₂H₅ | 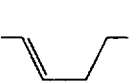 |  | | |  | |  |
| 309 | C₃H₇ |  |  | | | 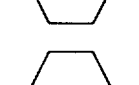 | |  |
| 310 | C₂H₅ | 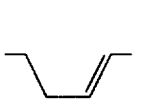 | 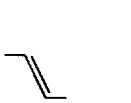 | | | 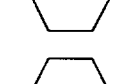 | |  |
| 311 | C₃H₇ | 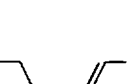 |  | | | 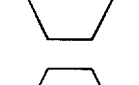 | |  |
| 312 | 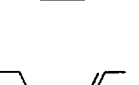 |  |  | | |  | | 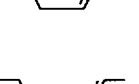 |
| 313 | 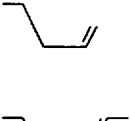 |  |  | | | 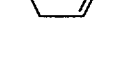 | | 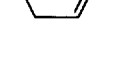 |
| 314 | 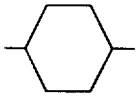 |  |  | | | 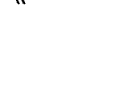 | | 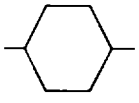 |
| 315 |  | 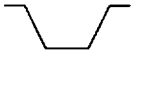 | 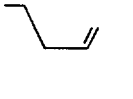 | | | 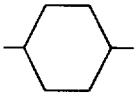 | |  |
| 316 | 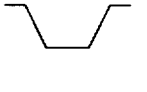 | 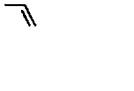 | 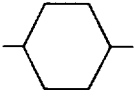 | | |  | | 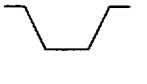 |

5,776,367

-continued

| No | R¹– | A¹ | –Z¹– | A² | –Z²– | –Z³– | A³ | –R² |
|----|-----|----|----|----|----|----|----|-----|
| 317 | CH≡C– | Cy | CH₂CH₂ | — | — | CH=CH | Cy | CH₂CH=CH₂ |
| 318 | CH≡C– | Cy | CH₂CH₂ | — | — | CH=CH | Cy | CH=CH₂ |
| 319 | CH≡C– | Cy | CH₂CH₂ | — | — | CH=CH | Cy | CH₂CH=CH₂ |
| 320 | C₃H₇ | Cy | C≡C | — | — | CH=CH | Cy | CH=CH₂ |
| 321 | C₃H₇ | Cy | C≡C | — | — | CH=CH | Cy | CH₂CH=CH₂ |
| 322 | C₃H₇ | Cy | C≡C | — | — | CH=CH | Cy | CH=CH₂ |
| 323 | C₃H₇ | Cy | C≡C | — | — | CH=CH | Cy | CH₂CH=CH₂ |
| 324 | C₃H₇ | Cy | C≡C | — | — | CH=CH | Cy | CH=CH₂ |
| 325 | C₃H₇ | Cy | C≡C | — | — | CH=CH | Cy | CH₂CH=CH₂ |
| 326 | C₃H₇ | Ph | C≡C | — | — | CH=CH | Cy | CH=CH₂ |
| 327 | C₃H₇ | Ph | C≡C | — | — | CH=CH | Cy | CH₂CH=CH₂ |
| 328 | C₃H₇ | Ph | C≡C | — | — | CH=CH | Cy | CH=CH₂ |
| 329 | C₃H₇ | Ph | C≡C | — | — | CH=CH | Cy | CH₂CH=CH₂ |
| 330 | C₃H₇ | Ph | C≡C | — | — | CH=CH | Cy | CH=CH₂ |

| No | R¹— | A¹ | —Z¹— | A² | —Z²— | —Z³— | A³ | —R² |
|---|---|---|---|---|---|---|---|---|
| 331 | C₃H₇ | 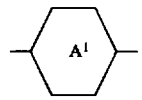 | 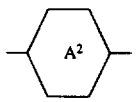 | 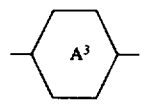 | | 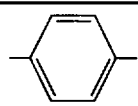 |  | 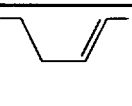 |
| 332 | C₃H₇ | 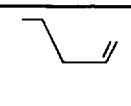 | | 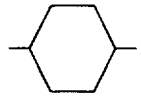 | | 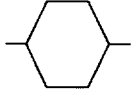 | 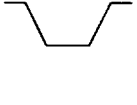 |  |
| 333 | C₅H₁₁ | 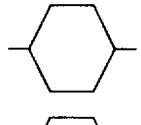 | | 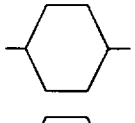 | |  | 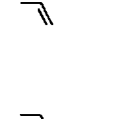 | 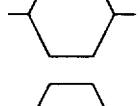 |
| 332 | C₃H₇ | 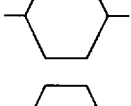 | | 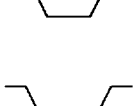 | | 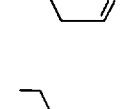 | 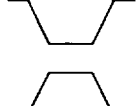 | 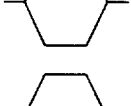 |
| 333 | C₅H₁₁ | 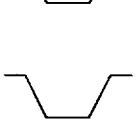 | | 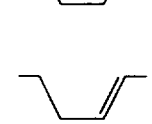 | | 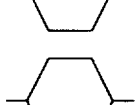 | 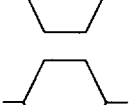 | 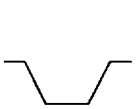 |
| 334 | C₃H₇ | 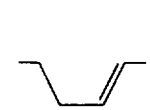 | | 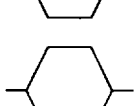 | | 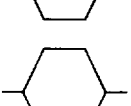 |  |  |
| 335 | C₅H₁₁ | 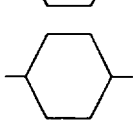 | | 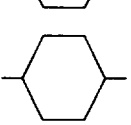 | |  |  | 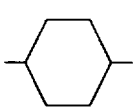 |
| 336 | C₃H₇ | 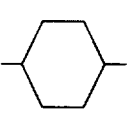 | | 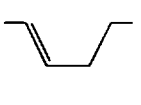 | |  | 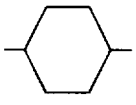 | 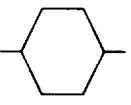 |
| 337 | C₅H₁₁ | 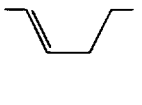 | | 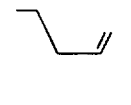 | | 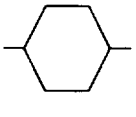 | 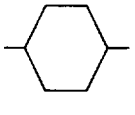 | 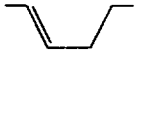 |
| 338 | C₃H₇ | 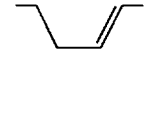 | | 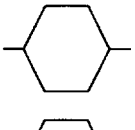 | | 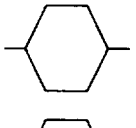 | | 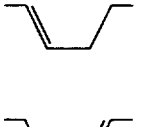 |
| 339 | C₅H₁₁ | 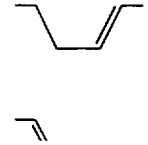 | | 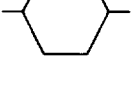 | | 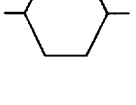 | | 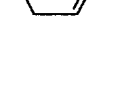 |
| 340 | C₃H₇ | | | | | | | |
| 341 | C₅H₁₁ | | | | | | | |
| 342 | C₃H₇ |  | |  | |  | |  |

5,776,367

| No | R¹– | A¹ | –Z¹– | A² | –Z²– | –Z³– | A³ | –R² |
|---|---|---|---|---|---|---|---|---|
| 343 | C₅H₁₁ | cyclohexane | | cyclohexane | | CH=CH | | CH=CH₂ |
| 344 | C₃H₇ | cyclohexane | | cyclohexane | | CH=CH | | CH₂-CH=CH₂ |
| 345 | C₅H₁₁ | cyclohexane | | cyclohexane | | CH=CH | | CH₂-CH=CH₂ |
| 346 | C₃H₇ | phenyl | | cyclohexane | | CH=CH | | CH=CH₂ |
| 347 | C₃H₇ | phenyl | | cyclohexane | | CH=CH | | CH₂-CH=CH₂ |
| 348 | C₃H₇ | phenyl | | cyclohexane | | CH=CH | | CH₂-CH=CH-CH₃ |
| 349 | C₃H₇ | phenyl | | cyclohexane | | CH=CH | | CH=CH₂ |
| 350 | C₃H₇ | phenyl | | cyclohexane | | CH=CH | | CH₂-CH=CH₂ |
| 351 | C₃H₇ | phenyl | | cyclohexane | | CH=CH | | CH₂-CH=CH-CH₃ |
| 352 | C₃H₇ | phenyl | | cyclohexane | | CH=CH | | CH=CH₂ |
| 353 | C₃H₇ | phenyl | | cyclohexane | | CH=CH | | CH₂-CH=CH₂ |
| 354 | C₃H₇ | phenyl | | cyclohexane | | CH=CH | | CH₂-CH=CH-CH₃ |
| 355 | C₃H₇ | phenyl | | phenyl | | CH=CH | | CH=CH₂ |
| 356 | C₃H₇ | phenyl | | phenyl | | CH=CH | | CH₂-CH=CH₂ |

-continued
| No | R¹— | A¹ | —Z¹— | A² | —Z²— | —Z³— | A³ | —R² |
|---|---|---|---|---|---|---|---|---|
| 357 | C₃H₇ | 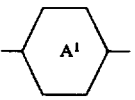 | |  | | 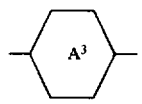 | |  |
| 358 | C₃H₇ |  | |  | |  | |  |
| 359 | C₃H₇ |  | |  | |  | |  |
| 360 | C₃H₇ |  | | 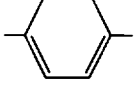 | | 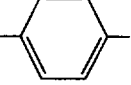 | |  |
| 361 | C₃H₇ | 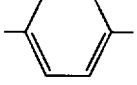 | |  | |  | | 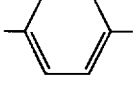 |
| 362 | C₃H₇ | 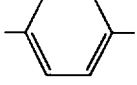 | |  | | 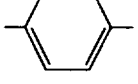 | | 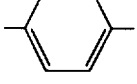 |
| 363 | C₃H₇ |  | | 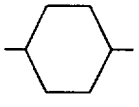 | | 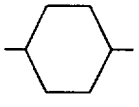 | |  |
| 364 | C₃H₇ |  | 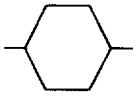 | 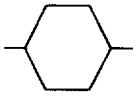 | | 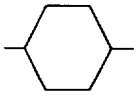 | |  |
| 365 | C₃H₇ | 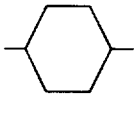 | 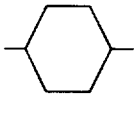 | 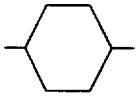 | |  | | 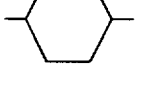 |
| 366 | C₃H₇ | 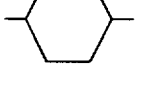 | 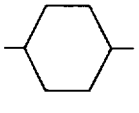 |  | | 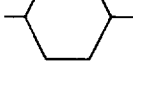 | | 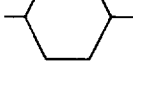 |
| 367 | C₃H₇ | 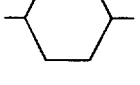 |  | 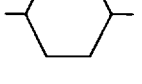 | | 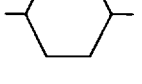 | | 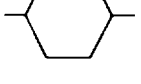 |
| 368 | C₃H₇ |  | | | | | | |
| 369 | C₃H₇ | | | | | | | |
| 370 | C₃H₇ | | | | | | | |

| No | R¹— | A¹ | —Z¹— | A² | —Z²— | —Z³— | A³ | —R² |
|---|---|---|---|---|---|---|---|---|
| 371 | C₃H₇ | cyclohexyl | CH₂CH₂ | cyclohexyl | — | CH=CH | | CH₂CH=CH |
| 372 | C₃H₇ | cyclohexyl | CH₂CH₂ | cyclohexyl | — | CH=CH | | CH=CHCH₃ |
| 373 | C₃H₇ | phenyl | CH₂CH₂ | cyclohexyl | — | CH₂CH₂ | | CH=CH₂ |
| 374 | C₃H₇ | phenyl | CH₂CH₂ | cyclohexyl | — | CH₂CH₂ | | CH₂CH=CH |
| 375 | C₃H₇ | phenyl | CH₂CH₂ | cyclohexyl | — | CH₂CH₂ | | CH=CHCH₃ |
| 376 | C₃H₇ | phenyl | CH₂CH₂ | cyclohexyl | — | CH=CH | | CH=CH₂ |
| 377 | C₃H₇ | phenyl | CH₂CH₂ | cyclohexyl | — | CH=CH | | CH₂CH=CH |
| 378 | C₃H₇ | phenyl | CH₂CH₂ | cyclohexyl | — | CH=CH | | CH=CHCH₃ |
| 379 | C₃H₇ | phenyl | CH₂CH₂ | cyclohexyl | — | CH₂CH₂ | | CH=CH₂ |
| 380 | C₃H₇ | phenyl | CH₂CH₂ | cyclohexyl | — | CH₂CH₂ | | CH₂CH=CH |
| 381 | C₃H₇ | phenyl | CH₂CH₂ | cyclohexyl | — | CH₂CH₂ | | CH=CHCH₃ |
| 382 | C₃H₇ | cyclohexyl | — | cyclohexyl | CH₂CH₂ | CH₂CH₂ | | CH=CH₂ |
| 383 | C₃H₇ | cyclohexyl | — | cyclohexyl | CH₂CH₂ | CH₂CH₂ | | CH₂CH=CH |
| 384 | C₃H₇ | cyclohexyl | — | cyclohexyl | CH₂CH₂ | CH₂CH₂ | | CH=CHCH₃ |

5,776,367
-continued
| No | R¹– | A¹ | –Z¹– | A² | –Z²– | –Z³– | A³ | –R² |
|---|---|---|---|---|---|---|---|---|
| 385 | C₃H₇ |  | | 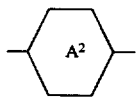 | 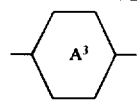 |  | |  |
| 386 | C₃H₇ |  | |  |  |  | | 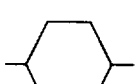 |
| 387 | C₃H₇ |  | |  |  |  | | 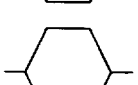 |
| 388 | C₃H₇ |  | |  |  | 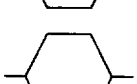 | | 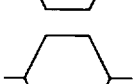 |
| 389 | C₃H₇ |  | |  |  | 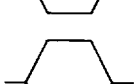 | | 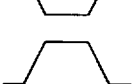 |
| 390 | C₃H₇ |  | |  |  | 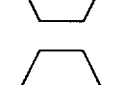 | | 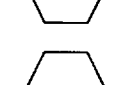 |
| 391 | C₃H₇ |  | |  |  | 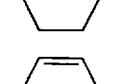 | | 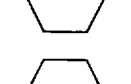 |
| 392 | C₃H₇ |  | |  |  |  | | 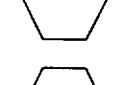 |
| 393 | C₃H₇ |  | |  |  | 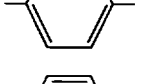 | |  |
| 394 | C₃H₇ |  | |  |  | 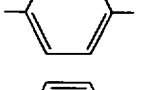 | |  |
| 395 | C₃H₇ |  | |  |  | 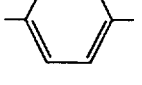 | | 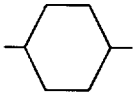 |
| 396 | C₃H₇ |  | |  |  | 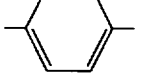 | |  |
| 397 | C₃H₇ |  | |  |  | 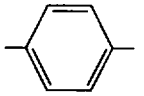 | | 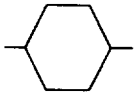 |
| 398 | C₃H₇ |  | |  |  | 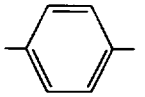 | |  |

-continued

| No | R¹– | A¹ | –Z¹– | A² | –Z²– | –Z³– | A³ | –R² |
|---|---|---|---|---|---|---|---|---|
| 399 | C₃H₇ | phenyl | | cyclohexyl | | CH=CH | cyclohexyl | CH₂CH=CHCH₃ |
| 400 | C₃H₇ | cyclohexyl | CH₂CH₂ | cyclohexyl | CH₂CH₂ | CH₂CH₂ | cyclohexyl | CH=CH₂ |
| 401 | C₃H₇ | cyclohexyl | CH₂CH₂ | cyclohexyl | CH₂CH₂ | CH₂CH₂ | cyclohexyl | CH₂CH=CH₂ |
| 402 | C₃H₇ | cyclohexyl | CH₂CH₂ | cyclohexyl | CH₂CH₂ | CH₂CH₂ | cyclohexyl | CH₂CH=CHCH₃ |
| 403 | C₃H₇ | cyclohexyl | CH₂CH₂ | cyclohexyl | CH₂CH₂ | CH=CH | cyclohexyl | CH=CH₂ |
| 404 | C₃H₇ | cyclohexyl | CH₂CH₂ | cyclohexyl | CH₂CH₂ | CH=CH | cyclohexyl | CH₂CH=CH₂ |
| 405 | C₃H₇ | cyclohexyl | CH₂CH₂ | cyclohexyl | CH₂CH₂ | CH=CH | cyclohexyl | CH₂CH=CHCH₃ |
| 406 | C₃H₇ | cyclohexyl | CH₂CH₂ | cyclohexyl | CH₂CH₂ | CH=CH | cyclohexyl | CH=CH₂ |
| 407 | C₃H₇ | cyclohexyl | CH₂CH₂ | cyclohexyl | CH₂CH₂ | CH=CH | cyclohexyl | CH₂CH=CH₂ |
| 408 | C₃H₇ | cyclohexyl | CH₂CH₂ | cyclohexyl | CH₂CH₂ | CH=CH | cyclohexyl | CH₂CH=CHCH₃ |
| 409 | C₃H₇ | phenyl | CH₂CH₂ | cyclohexyl | CH₂CH₂ | CH₂CH₂ | cyclohexyl | CH=CH₂ |
| 410 | C₃H₇ | phenyl | CH₂CH₂ | cyclohexyl | CH₂CH₂ | CH₂CH₂ | cyclohexyl | CH₂CH=CH₂ |
| 411 | C₃H₇ | phenyl | CH₂CH₂ | cyclohexyl | CH₂CH₂ | CH₂CH₂ | cyclohexyl | CH₂CH=CHCH₃ |
| 412 | C₃H₇ | phenyl | CH₂CH₂ | cyclohexyl | CH₂CH₂ | CH=CH | cyclohexyl | CH=CH₂ |

| No | R¹– | A¹ | –Z¹– | A² | –Z²– | –Z³– | A³ | –R² |
|---|---|---|---|---|---|---|---|---|
| 413 | C₃H₇ | phenyl | CH₂CH₂ | cyclohexyl | CH₂CH₂ | CH=CH | cyclohexyl | CH₂CH=CH₂ |
| 414 | C₃H₇ | phenyl | CH₂CH₂ | cyclohexyl | CH₂CH₂ | CH=CH | cyclohexyl | CH₂CH=CHCH₃ |
| 415 | C₃H₇ | phenyl | CH₂CH₂ | cyclohexyl | CH₂CH₂ | CH=CH | cyclohexyl | CH=CH₂ |
| 416 | C₃H₇ | phenyl | CH₂CH₂ | cyclohexyl | CH₂CH₂ | CH=CH | cyclohexyl | CH₂CH=CH₂ |
| 417 | C₃H₇ | phenyl | CH₂CH₂ | cyclohexyl | CH₂CH₂ | CH=CH | cyclohexyl | CH₂CH=CHCH₃ |
| 418 | C₃H₇ | cyclohexyl | CH=CH | cyclohexyl | CH₂CH₂ | CH=CH | cyclohexyl | CH=CH₂ |
| 419 | C₃H₇ | cyclohexyl | CH=CH | cyclohexyl | CH₂CH₂ | CH=CH | cyclohexyl | CH₂CH=CH₂ |
| 420 | C₃H₇ | cyclohexyl | CH=CH | cyclohexyl | CH₂CH₂ | CH=CH | cyclohexyl | CH₂CH=CHCH₃ |
| 421 | C₃H₇ | cyclohexyl | CH=CH | cyclohexyl | CH₂CH₂ | CH=CH | cyclohexyl | CH=CH₂ |
| 422 | C₃H₇ | cyclohexyl | CH=CH | cyclohexyl | CH₂CH₂ | CH=CH | cyclohexyl | CH₂CH=CH₂ |
| 423 | C₃H₇ | cyclohexyl | CH=CH | cyclohexyl | CH₂CH₂ | CH=CH | cyclohexyl | CH₂CH=CHCH₃ |
| 424 | C₃H₇ | cyclohexyl | CH=CH | cyclohexyl | CH₂CH₂ | CH=CH | cyclohexyl | CH=CH₂ |
| 425 | C₃H₇ | cyclohexyl | CH=CH | cyclohexyl | CH₂CH₂ | CH=CH | cyclohexyl | CH₂CH=CH₂ |
| 426 | C₃H₇ | cyclohexyl | CH=CH | cyclohexyl | CH₂CH₂ | CH=CH | cyclohexyl | CH₂CH=CHCH₃ |

| No | R¹− | −A¹− | −Z¹− | −A²− | −Z²− | −Z³− | −A³− | −R² |
|---|---|---|---|---|---|---|---|---|
| 427 | C₃H₇ | phenyl | CH=CH | cyclohexyl | — | CH₂CH₂ | — | vinyl |
| 428 | C₃H₇ | phenyl | CH=CH | cyclohexyl | — | CH₂CH₂ | — | CH₂CH=CH₂ |
| 429 | C₃H₇ | phenyl | CH=CH | cyclohexyl | — | CH₂CH₂ | — | CH=CHCH₃ |
| 430 | C₃H₇ | phenyl | CH=CH | cyclohexyl | — | CH=CHCH₂ | — | vinyl |
| 431 | C₃H₇ | phenyl | CH=CH | cyclohexyl | — | CH=CHCH₂ | — | CH₂CH=CH₂ |
| 432 | C₃H₇ | phenyl | CH=CH | cyclohexyl | — | CH=CHCH₂ | — | CH=CHCH₃ |
| 433 | C₃H₇ | phenyl | CH=CH | cyclohexyl | — | CH₂CH₂ | — | vinyl |
| 434 | C₃H₇ | phenyl | CH=CH | cyclohexyl | — | CH₂CH₂ | — | CH₂CH=CH₂ |
| 435 | C₃H₇ | phenyl | CH=CH | cyclohexyl | — | CH₂CH₂ | — | CH=CHCH₃ |
| 436 | C₃H₇ | cyclohexyl | — | cyclohexyl | CH=CH | CH₂CH₂ | — | vinyl |
| 437 | C₃H₇ | cyclohexyl | — | cyclohexyl | CH=CH | CH₂CH₂ | — | CH₂CH=CH₂ |
| 438 | C₃H₇ | cyclohexyl | — | cyclohexyl | CH=CH | CH₂CH₂ | — | CH=CHCH₃ |
| 439 | C₃H₇ | cyclohexyl | — | cyclohexyl | CH=CH | CH=CHCH₂ | — | vinyl |
| 440 | C₃H₇ | cyclohexyl | — | cyclohexyl | CH=CH | CH=CHCH₂ | — | CH₂CH=CH₂ |

-continued

| No | R¹— | A¹ | —Z¹— | A² | —Z²— | —Z³— | A³ | —R² |
|---|---|---|---|---|---|---|---|---|
| 441 | C₃H₇ | cyclohexane | | cyclohexane | CH=CH | CH=CH | | CH=CH |
| 442 | C₃H₇ | cyclohexane | | cyclohexane | CH=CH | CH=CH | | =CH |
| 443 | C₃H₇ | cyclohexane | | cyclohexane | CH=CH | CH=CH | | CH=CH |
| 444 | C₃H₇ | cyclohexane | | cyclohexane | CH=CH | CH=CH | | CH=CH |
| 445 | C₃H₇ | phenyl | | cyclohexane | CH=CH | CH=CH | | =CH |
| 446 | C₃H₇ | phenyl | | cyclohexane | CH=CH | CH=CH | | CH=CH |
| 447 | C₃H₇ | phenyl | | cyclohexane | CH=CH | CH=CH | | CH=CH |
| 448 | C₃H₇ | phenyl | | cyclohexane | CH=CH | CH=CH | | =CH |
| 449 | C₃H₇ | phenyl | | cyclohexane | CH=CH | CH=CH | | CH=CH |
| 450 | C₃H₇ | phenyl | | cyclohexane | CH=CH | CH=CH | | CH=CH |
| 451 | C₃H₇ | phenyl | | cyclohexane | CH=CH | CH=CH | | =CH |
| 452 | C₃H₇ | phenyl | | cyclohexane | CH=CH | CH=CH | | CH=CH |
| 453 | C₃H₇ | phenyl | | cyclohexane | CH=CH | CH=CH | | CH=CH |
| 454 | C₃H₇ | cyclohexane | CH=CH | cyclohexane | CH=CH | CH=CH | | =CH |

-continued

| No | R¹— | —A¹— | —Z¹— | —A²— | —Z²— | —Z³— | —A³— | —R² |
|---|---|---|---|---|---|---|---|---|
| 455 | C₃H₇ | cyclohexyl | CH=CH | cyclohexyl | CH=CH | CH₂CH₂ | | CH₂CH=CH₂ |
| 456 | C₃H₇ | cyclohexyl | CH=CH | cyclohexyl | CH=CH | CH₂CH₂ | | CH₂CH=CHCH₃ |
| 457 | C₃H₇ | cyclohexyl | CH=CH | cyclohexyl | CH=CH | CH=CH | | CH=CH₂ |
| 458 | C₃H₇ | cyclohexyl | CH=CH | cyclohexyl | CH=CH | CH=CH | | CH₂CH=CH₂ |
| 459 | C₃H₇ | cyclohexyl | CH=CH | cyclohexyl | CH=CH | CH=CH | | CH₂CH=CHCH₃ |
| 460 | C₃H₇ | cyclohexyl | CH=CH | cyclohexyl | CH=CH | CH₂CH=CH | | CH=CH₂ |
| 461 | C₃H₇ | cyclohexyl | CH=CH | cyclohexyl | CH=CH | CH₂CH=CH | | CH₂CH=CH₂ |
| 462 | C₃H₇ | cyclohexyl | CH=CH | cyclohexyl | CH=CH | CH₂CH=CH | | CH₂CH=CHCH₃ |
| 463 | C₃H₇ | cyclohexyl | C≡C | cyclohexyl | | CH₂CH₂ | | CH=CH₂ |
| 464 | C₃H₇ | cyclohexyl | C≡C | cyclohexyl | | CH₂CH₂ | | CH₂CH=CH₂ |
| 465 | C₃H₇ | cyclohexyl | C≡C | cyclohexyl | | CH₂CH₂ | | CH₂CH=CHCH₃ |
| 466 | C₃H₇ | cyclohexyl | C≡C | cyclohexyl | | CH=CH | | CH=CH₂ |
| 467 | C₃H₇ | cyclohexyl | C≡C | cyclohexyl | | CH=CH | | CH₂CH=CH₂ |
| 468 | C₃H₇ | cyclohexyl | C≡C | cyclohexyl | | CH=CH | | CH₂CH=CHCH₃ |

| No | R¹- | -A¹- | -Z¹- | -A²- | -Z²- | -Z³- | -A³- | -R² |
|---|---|---|---|---|---|---|---|---|
| 469 | C₃H₇ | cyclohexyl | ≡ | cyclohexyl | | CH₂-CH= | cyclohexyl | =CH |
| 470 | C₃H₇ | cyclohexyl | ≡ | cyclohexyl | | CH₂-CH= | cyclohexyl | CH₂-CH= |
| 471 | C₃H₇ | cyclohexyl | ≡ | cyclohexyl | | CH₂-CH= | cyclohexyl | CH₂-CH=CH |
| 472 | C₃H₇ | phenyl | ≡ | phenyl | | CH₂-CH= | cyclohexyl | =CH |
| 473 | C₃H₇ | phenyl | ≡ | phenyl | | CH₂-CH= | cyclohexyl | CH₂-CH= |
| 474 | C₃H₇ | phenyl | ≡ | phenyl | | CH₂-CH= | cyclohexyl | CH₂-CH=CH |
| 475 | C₃H₇ | phenyl | ≡ | phenyl | | =CH-CH₂ | cyclohexyl | =CH |
| 476 | C₃H₇ | phenyl | ≡ | phenyl | | =CH-CH₂ | cyclohexyl | CH₂-CH= |
| 477 | C₃H₇ | phenyl | ≡ | phenyl | | =CH-CH₂ | cyclohexyl | =CH-CH₂-CH= |
| 478 | C₃H₇ | phenyl | ≡ | phenyl | | CH₂-CH= | cyclohexyl | =CH |
| 479 | C₃H₇ | phenyl | ≡ | phenyl | | CH₂-CH= | cyclohexyl | CH₂-CH= |
| 480 | C₃H₇ | phenyl | ≡ | phenyl | | CH₂-CH= | cyclohexyl | CH₂-CH=CH |
| 481 | C₃H₇ | cyclohexyl | ≡ | cyclohexyl | CH₂-CH₂ | CH₂-CH= | cyclohexyl | =CH |
| 482 | C₃H₇ | cyclohexyl | ≡ | cyclohexyl | CH₂-CH₂ | CH₂-CH= | cyclohexyl | CH₂-CH= |

5,776,367
-continued
| No | R¹– | A¹ | –Z¹– | A² | –Z²– | –Z³– | A³ | –R² |
|---|---|---|---|---|---|---|---|---|
| 483 | C₃H₇ | 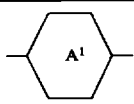 | 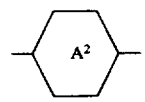 | 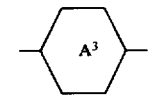 |  |  | | 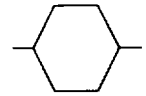 |
| 484 | C₃H₇ |  |  |  |  |  | |  |
| 485 | C₃H₇ | 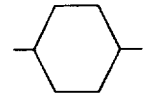 |  |  |  |  | |  |
| 486 | C₃H₇ | 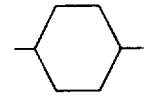 |  |  |  | 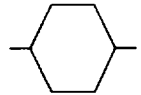 | |  |
| 487 | C₃H₇ | 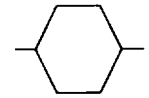 |  |  |  | 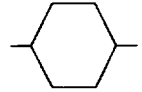 | |  |
| 488 | C₃H₇ |  |  |  |  | 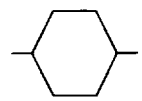 | |  |
| 489 | C₃H₇ | 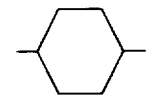 |  |  |  | 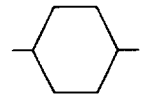 | |  |
| 490 | C₃H₇ | 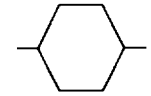 |  |  |  | 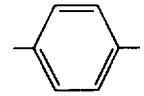 | |  |
| 491 | C₃H₇ | 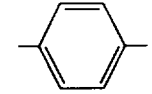 |  |  |  | 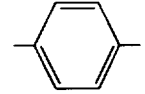 | |  |
| 492 | C₃H₇ | 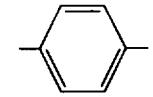 |  |  |  | 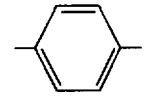 | |  |
| 493 | C₃H₇ | 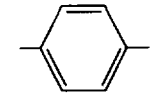 |  |  |  | 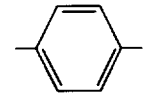 | |  |
| 494 | C₃H₇ | 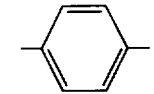 |  |  |  | 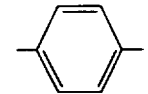 | |  |
| 495 | C₃H₇ | 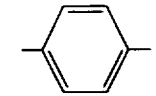 |  |  |  | 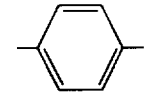 | |  |
| 496 | C₃H₇ | 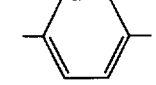 |  |  |  | 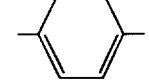 | |  |

5,776,367 -continued
| No | R¹– | A¹ | –Z¹– | A² | –Z²– | –Z³– | A³ | –R² |
|---|---|---|---|---|---|---|---|---|
| 497 | C₃H₇ | 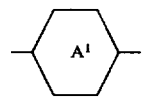 | ≡ | 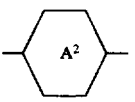 | 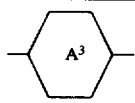 | 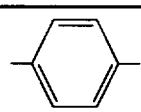 | | 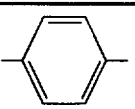 |
| 498 | C₃H₇ |  | ≡ |  |  | 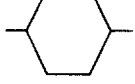 | | 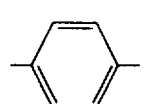 |
| 499 | C₂H₅ | 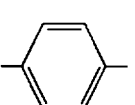 | | | |  |  |  |
| 500 | C₂H₅ | 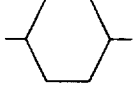 | | | | 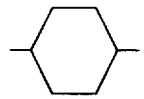 | 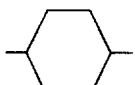 | 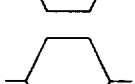 |
| 501 | C₂H₅ | 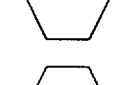 | | | | 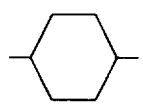 | 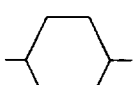 | 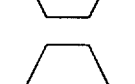 |
| 502 | C₃H₇ | 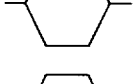 | | | | 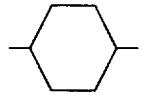 |  | 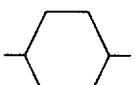 |
| 503 | C₃H₇ | 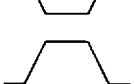 | | | | 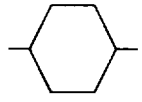 | 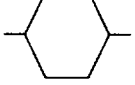 |  |
| 504 | C₃H₇ | 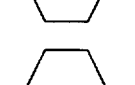 | | | |  | 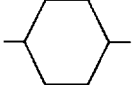 | 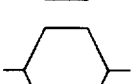 |
| 505 | C₅H₁₁ | 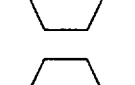 | | | |  | 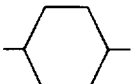 | 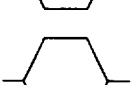 |
| 506 | C₅H₁₁ | 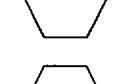 | | | |  |  | 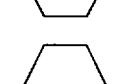 |
| 507 | C₅H₁₁ | 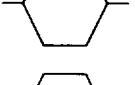 | | | | 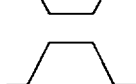 | 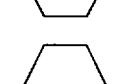 | 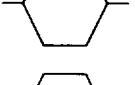 |
| 508 | C₂H₅ | 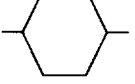 | | | |  | 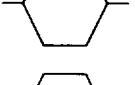 | 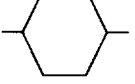 |
| 509 | C₂H₅ |  | | | |  | 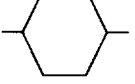 |  |
| 510 | C₂H₅ | 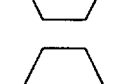 | | | | 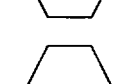 | 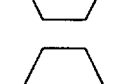 | 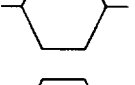 |

-continued

| No | R¹— | —A¹— | —Z¹— | —A²— | —Z²— | —Z³— | —A³— | —R² |
|----|-----|------|------|------|------|------|------|-----|
| 511 | C₃H₇ | cyclohexyl | | | | link | phenyl | vinyl |
| 512 | C₃H₇ | cyclohexyl | | | | link | phenyl | propenyl |
| 513 | C₃H₇ | cyclohexyl | | | | link | phenyl | propenyl |
| 514 | C₅H₁₁ | cyclohexyl | | | | link | phenyl | vinyl |
| 515 | C₅H₁₁ | cyclohexyl | | | | link | phenyl | propenyl |
| 516 | C₅H₁₁ | cyclohexyl | | | | link | phenyl | propenyl |

The liquid crystal composition provided according to the present invention is a composition containing at least one liquid crystalline compound expressed by the formula (1). As other components added to the liquid crystalline compound expressed by the formula (1), it is preferred to use at least one compound (hereinafter referred to as the second A component) selected from the groups consisting of the above formulas (2), (3) and (4), and/or at least one compound (hereinafter referred to as the second B component) selected from the group consisting of the formulas (5), (6), (7), (8) and (9), and further, in order to adjust the threshold voltage, liquid crystal phase temperature range, optical anisotropy value, dielectric anisotropy value, viscosity, etc., other known liquid crystalline compounds may be also blended as the third component.

Among the above second A component, compounds expressed by the formulas (2-1) to (2-15), (3-1) to (3-48) and (4-1) to (4-55) can be listed as preferable examples of the compounds expressed by the formulas (2), (3) and (4).

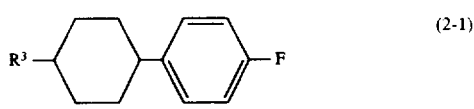  (2-1)

  (2-2)

-continued

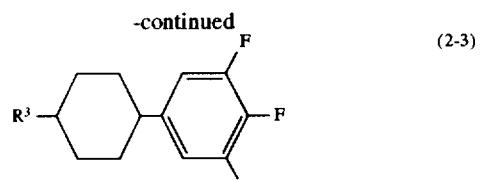  (2-3)

(2-4)

(2-5)

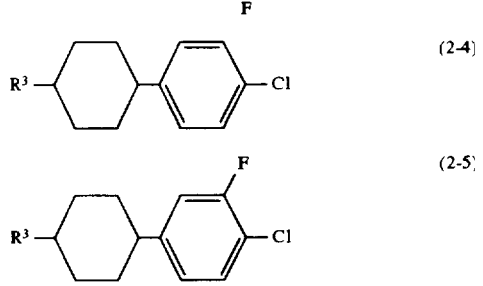  (2-6)

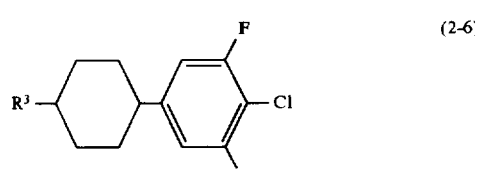  (2-7)

(2-8)

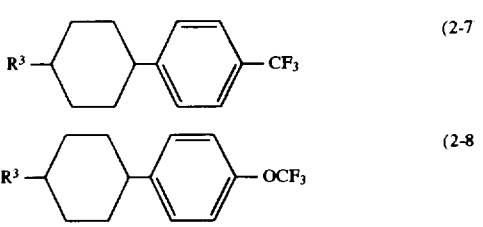

-continued
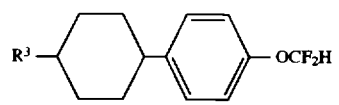 (2-9)
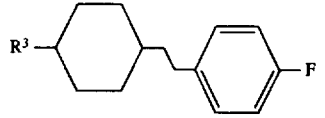 (2-10)
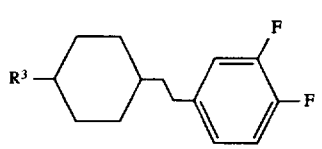 (2-11)
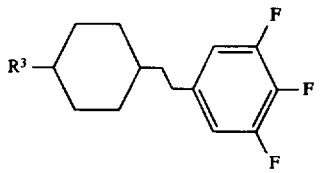 (2-12)
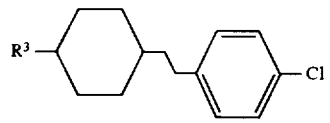 (2-13)
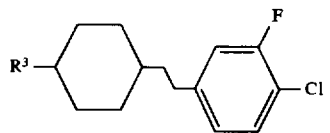 (2-14)
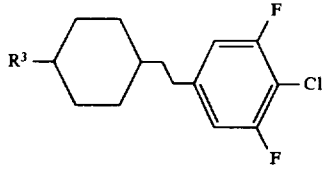 (2-15)
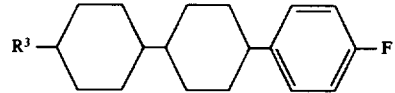 (3-1)
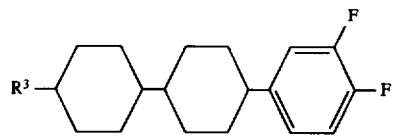 (3-2)
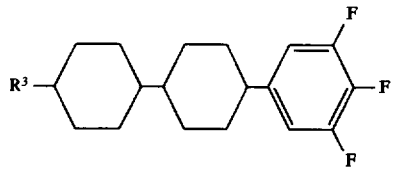 (3-3)
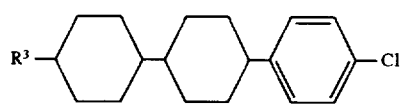 (3-4)
-continued
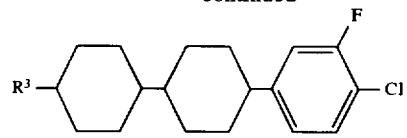 (3-5)
 (3-6)
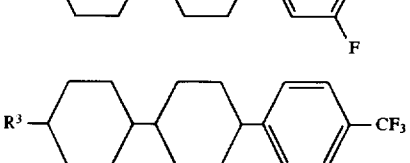 (3-7)
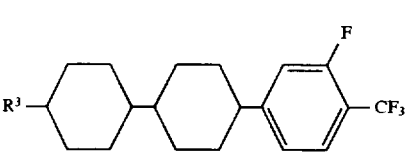 (3-8)
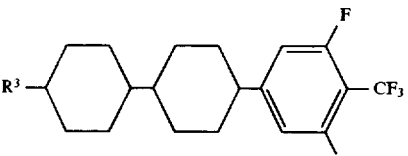 (3-9)
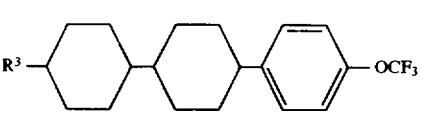 (3-10)
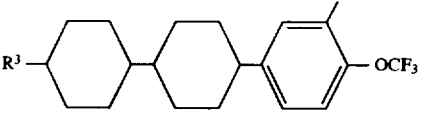 (3-11)
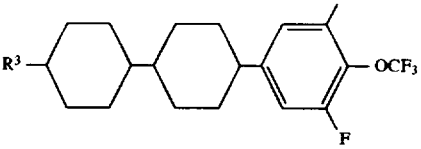 (3-12)
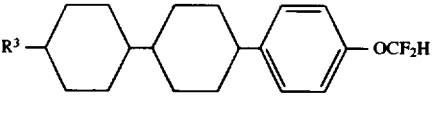 (3-13)
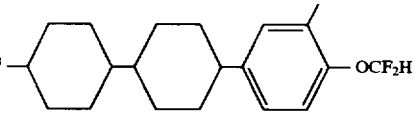 (3-14)
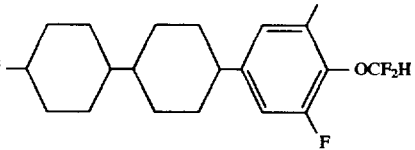 (3-15)

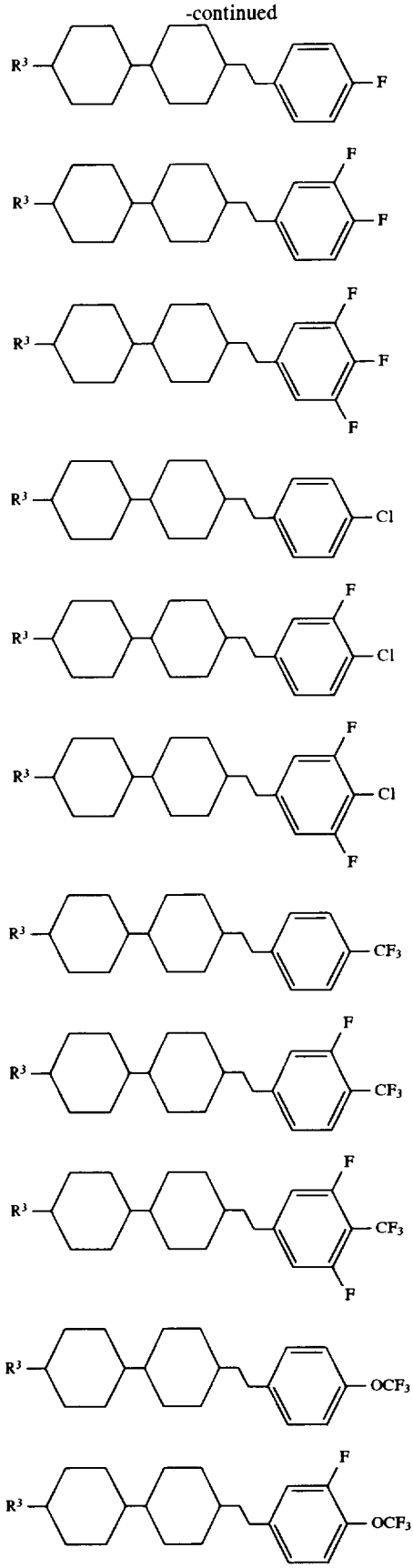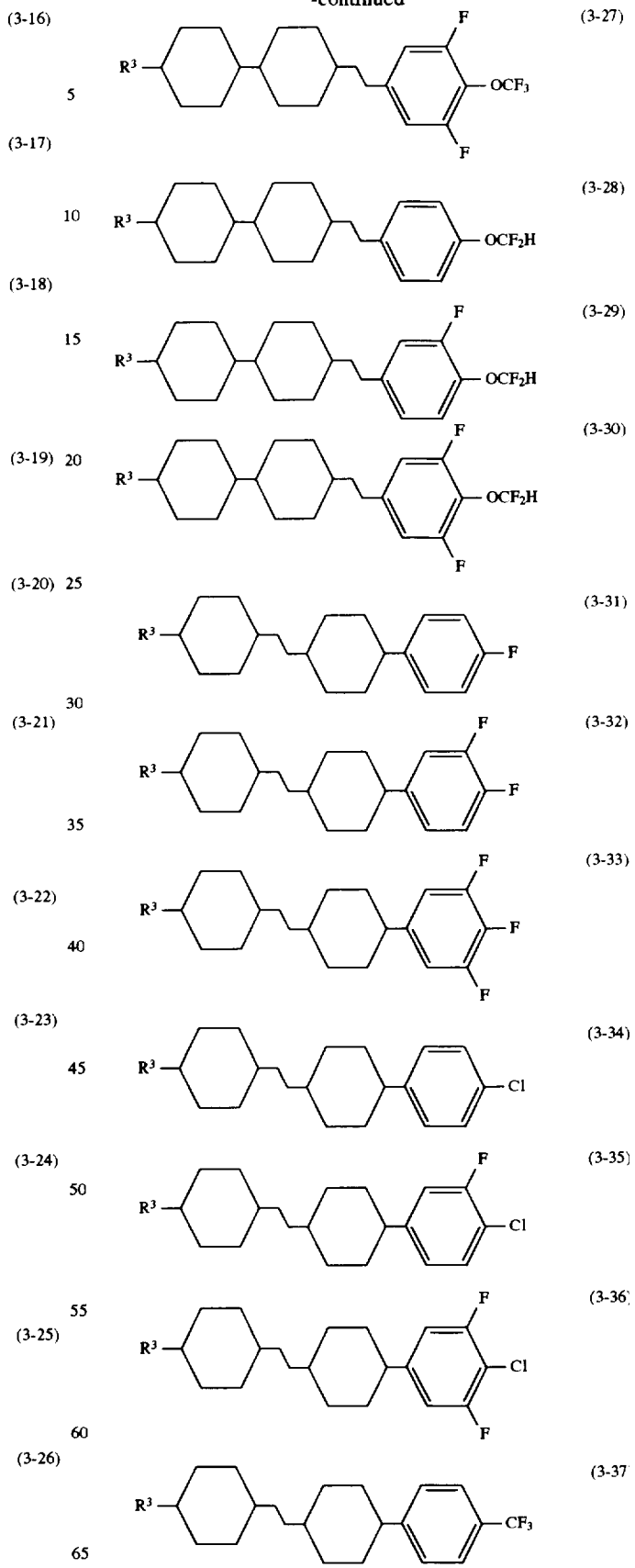

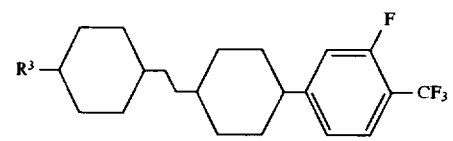 (3-38)
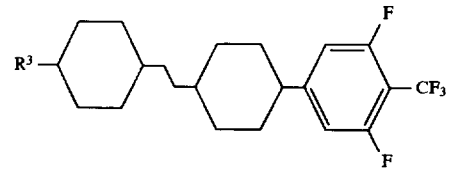 (3-39)
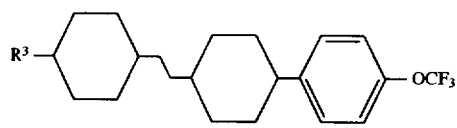 (3-40)
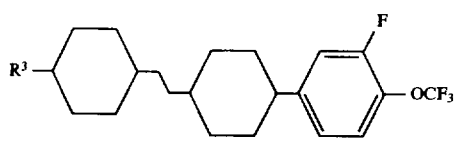 (3-41)
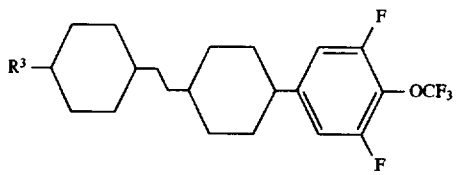 (3-42)
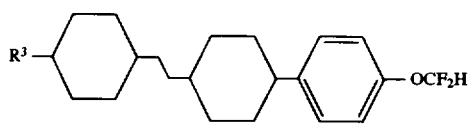 (3-43)
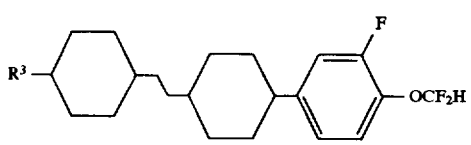 (3-44)
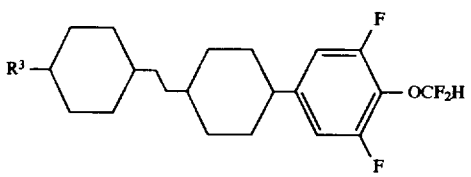 (3-45)
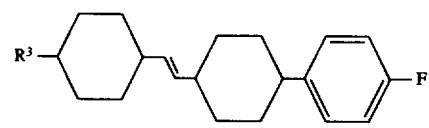 (3-46)
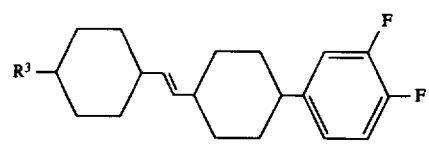 (3-47)
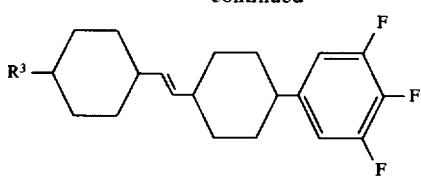 (3-48)
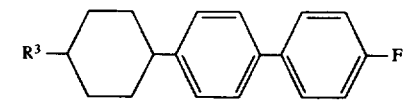 (4-1)
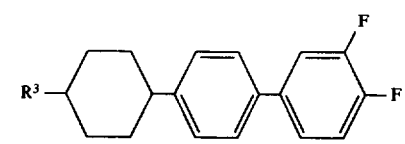 (4-2)
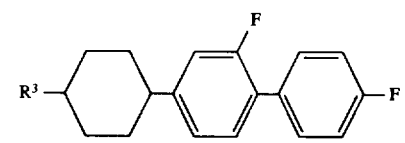 (4-3)
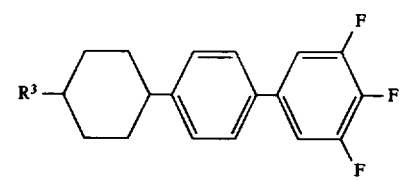 (4-4)
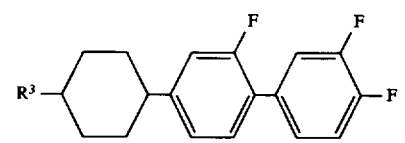 (4-5)
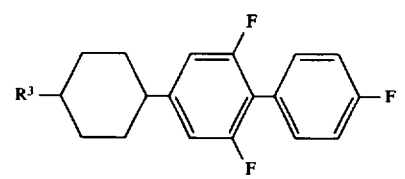 (4-6)
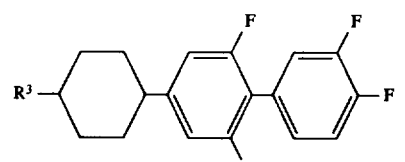 (4-7)
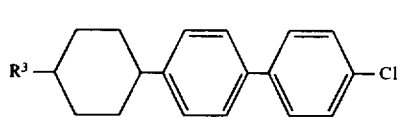 (4-8)
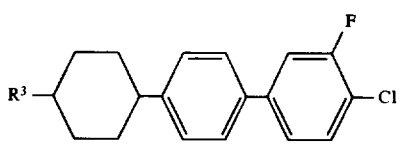 (4-9)

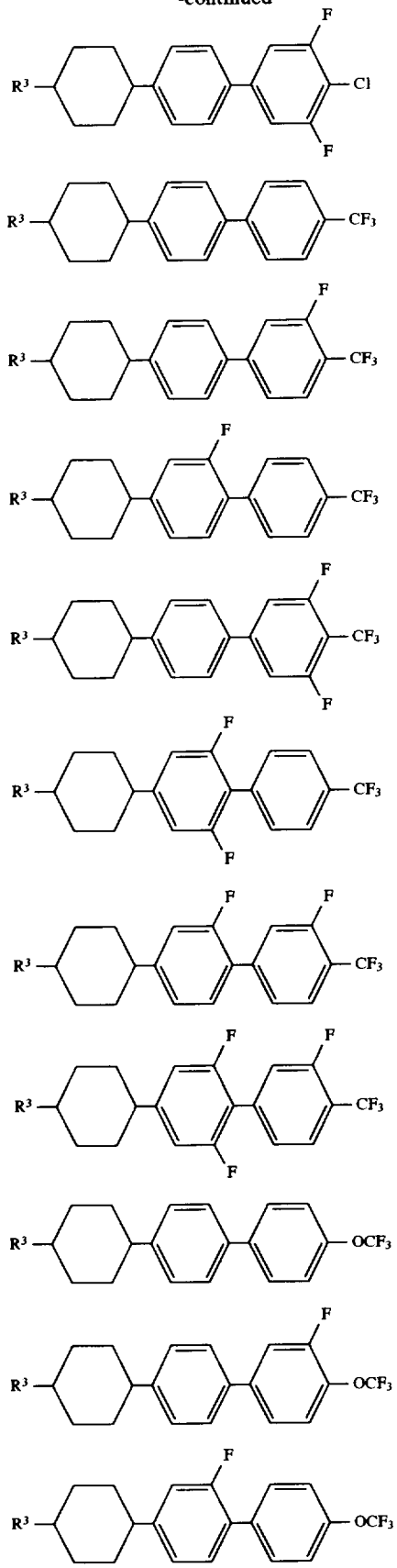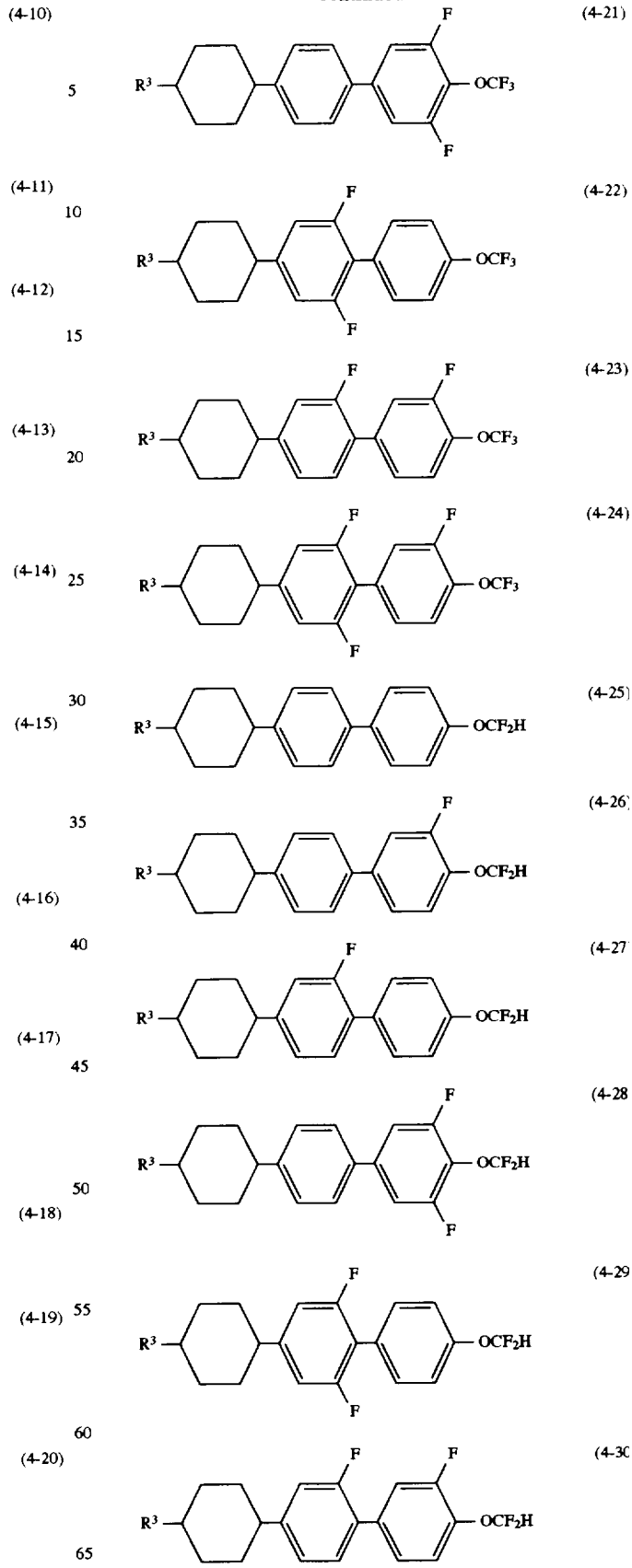

(4-31) (4-32) (4-33) (4-34) (4-35) (4-36) (4-37) (4-38) (4-39) (4-40) (4-41) (4-42) (4-43) (4-44) (4-45) (4-46) (4-47) (4-48) (4-49) (4-50) (4-51)

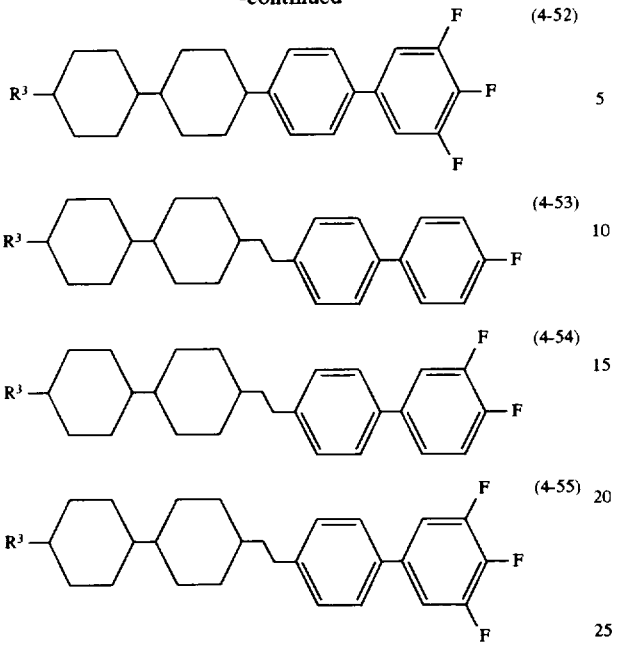

The compounds expressed by these formulas (2) to (4) have a positive dielectric anisotropy value and superior heat stability and chemical stability. These compounds are used within a range of 1 to 99% by weight based upon the total weight of the liquid crystal composition, preferably within a range of 10 to 97% by weight, more preferably within a range of 40 to 95% by weight.

Among the above second B component, as preferable examples of compounds expressed by the formulas (5), (6) and (7), compounds respectively expressed by the formulas (5-1) to (5-24), (6-1) to (6-3) and (7-1) to (7-17) can be listed.

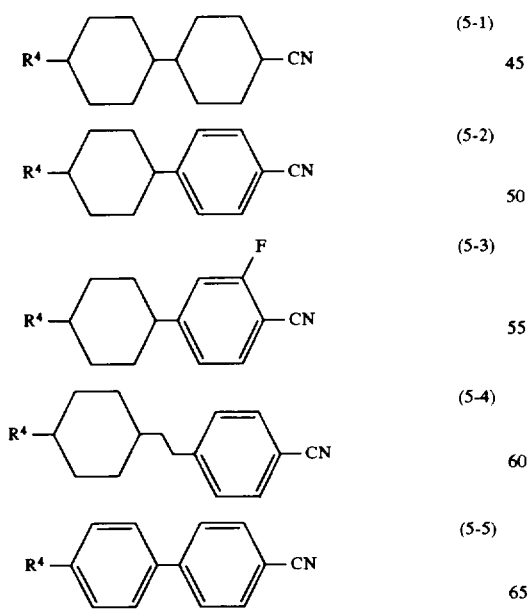

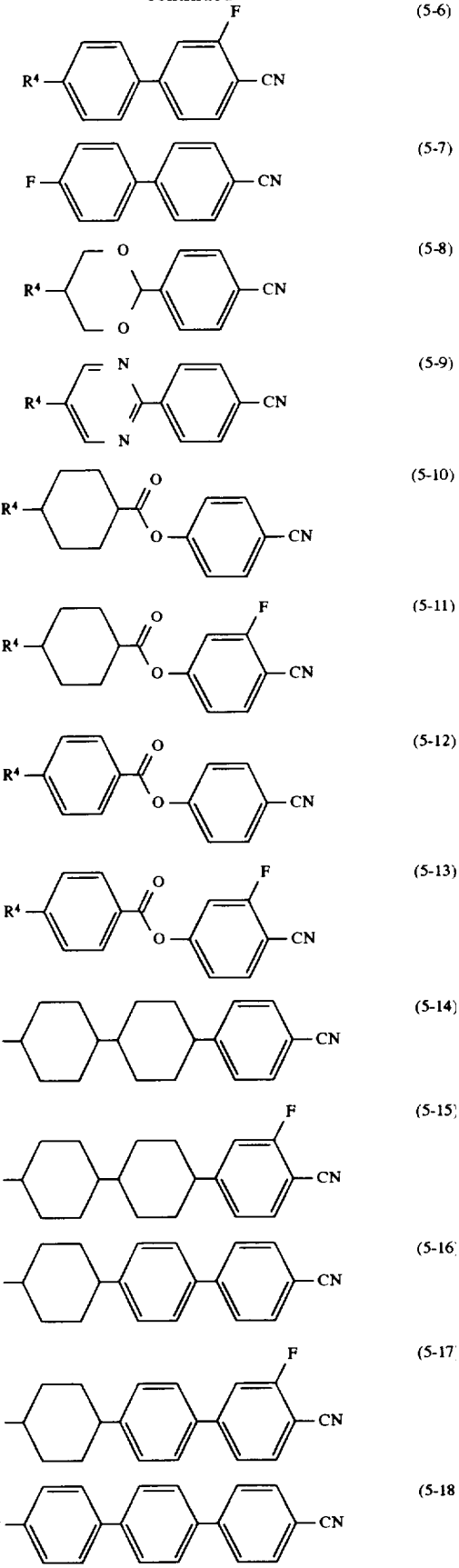

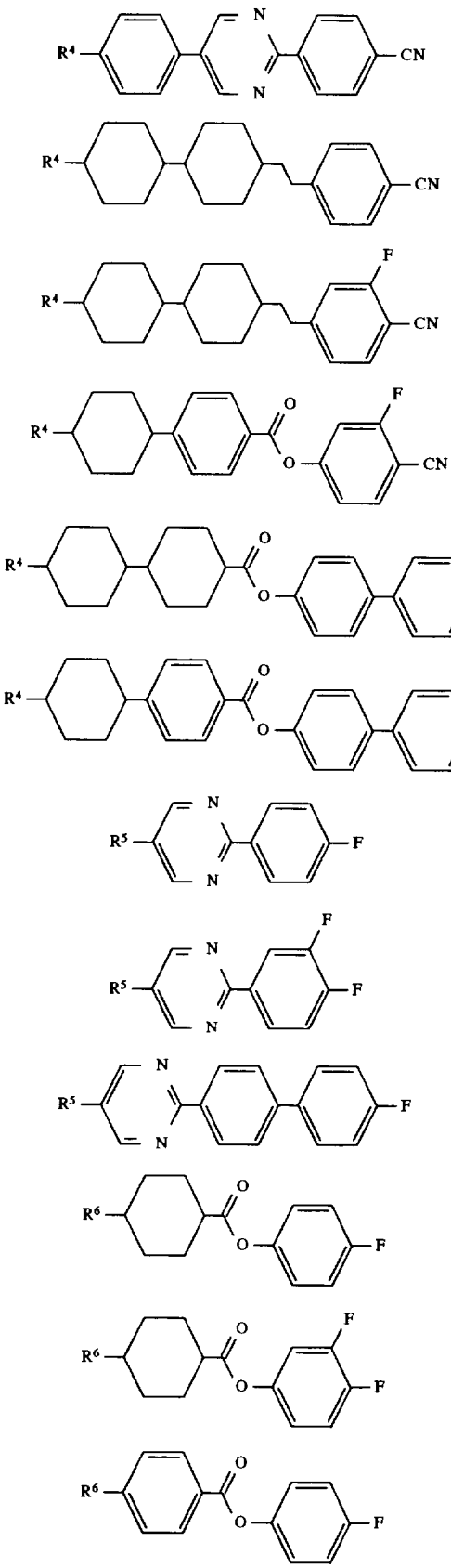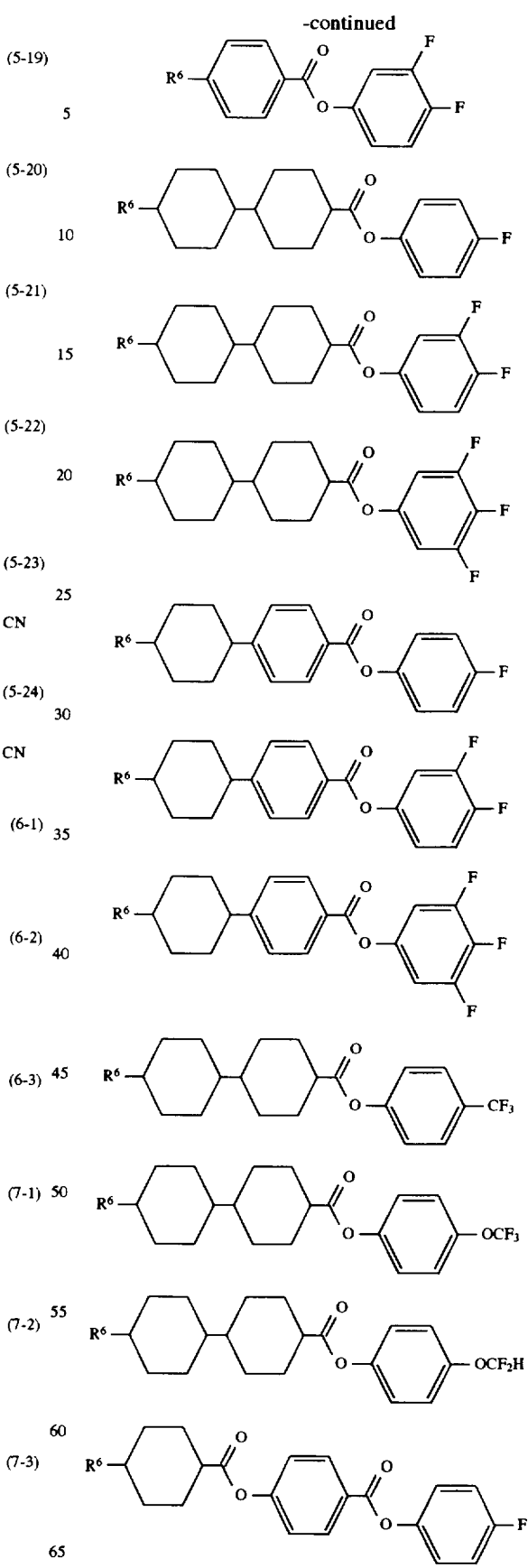

-continued

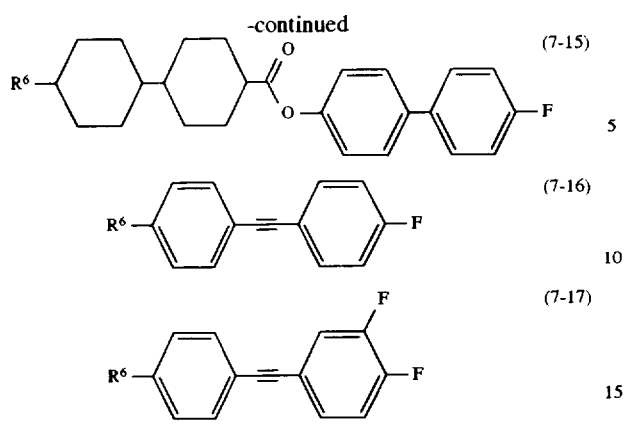

The compounds expressed by these formulas (5) to (7) have a large positive dielectric anisotropy value and may be used as components of liquid crystal compositions, particularly for reducing the threshold voltage. Further, they may be used for adjusting the viscosity and the optical anisotropy value and for broadening the liquid crystal temperature range, and further for improving the steepness.

Further, among the second B component, as preferable examples of compounds expressed by the formulas (8) and (9), compounds respectively expressed by the formulas (8-1) to (8-8) and the formulas (9-1) to (9-16) can be mentioned.

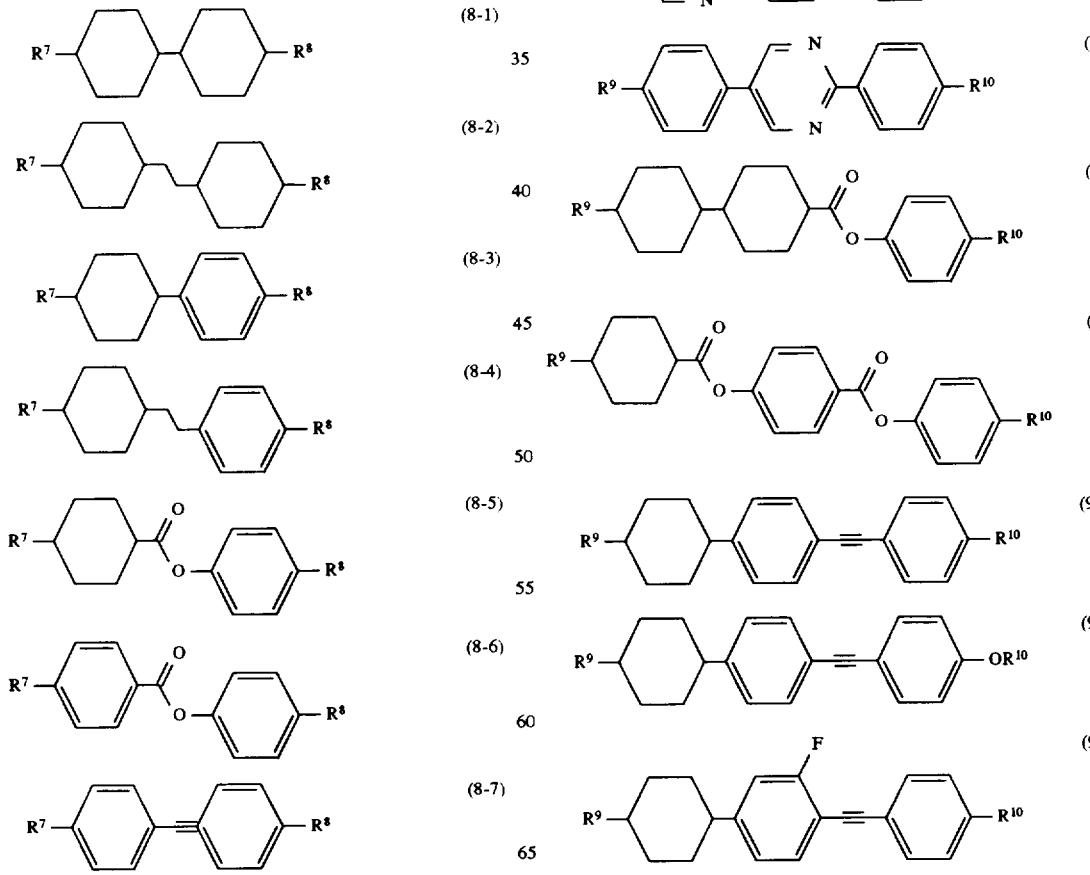

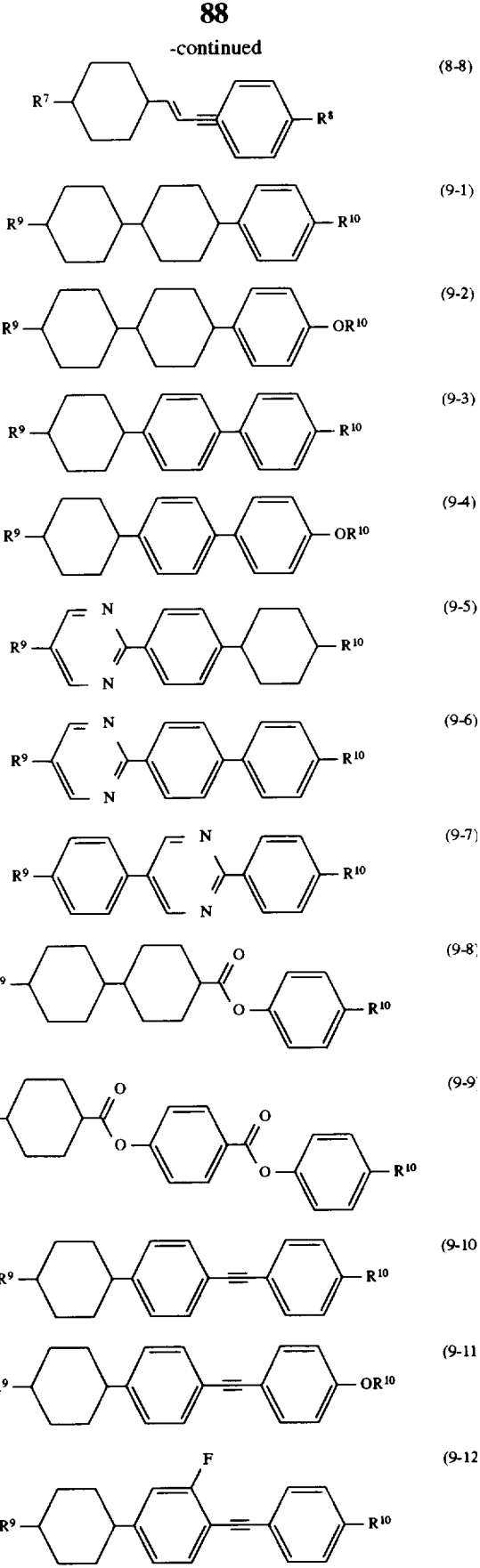

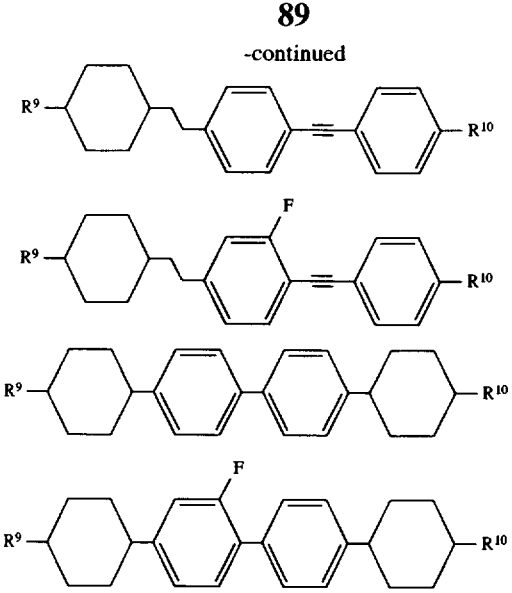

(9-13)
(9-14)
(9-15)
(9-16)

The liquid crystal composition used according to the present invention can be prepared according to a process which is conventional by itself. In general, a process of dissolving various components with each other at a high temperature has been employed. Further, the liquid crystal composition of the present invention may be improved by suitable additives corresponding to the objective use applications and optimized.

Such additives have been well known by persons of ordinary skill and described in details in literatures, etc. For example, in order to induce the helical structure of liquid crystals, thereby adjusting necessary twist angle and preventing reverse twist, a chiral dopant is usually added, or a dichroic pigment such as those of mellocyanne group, styryl group, azo group, azomethine group, azoxy group, quinophthallon group, anthraquinone group, tetrazine group, etc. is added and used as a liquid crystal composition for guest-host (GH) mode. Further, the liquid crystal composition is used as liquid crystal composition for polymer-dispersion type, liquid crystal display element (PDLCD) represented by NCAP prepared by microcapsulating nematic liquid crystals or polymer network liquid crystal display element (PNLCD) wherein three-dimentional, knitted form high molecules are prepared in liquid crystals. Further, the liquid crystal composition can be used for birefringence control (ECB) mode and for dynamic scattering mode.

As the nematic liquid crystal containing the compound of the present invention, the following composition examples (composition examples 1 to 15) can be listed:

COMPOSITION EXAMPLE 1

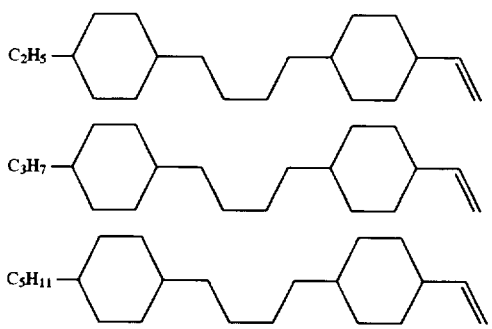

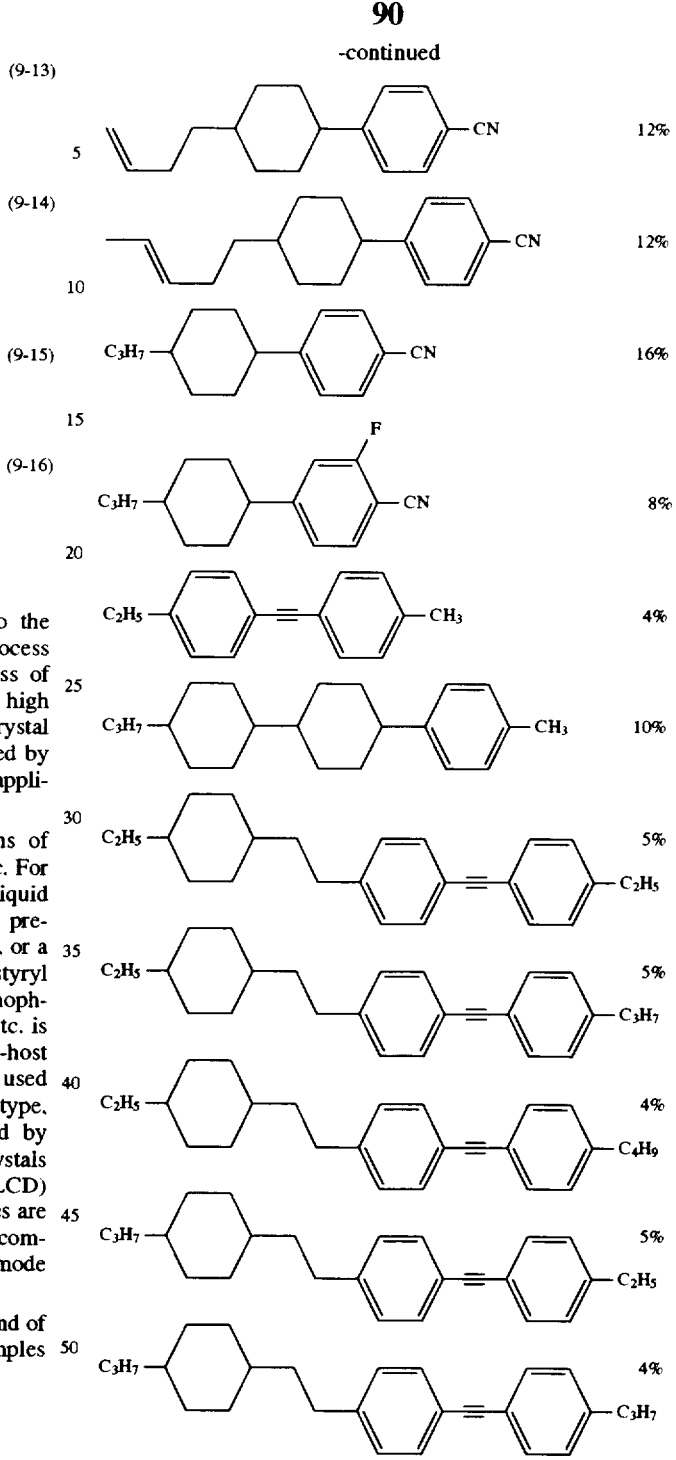

COMPOSITION EXAMPLE 2

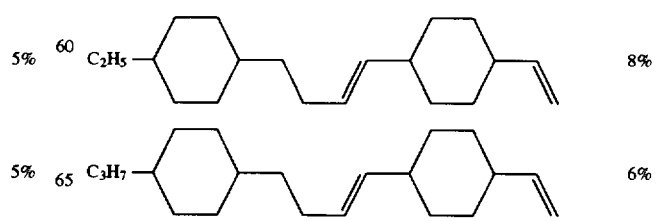

91
-continued
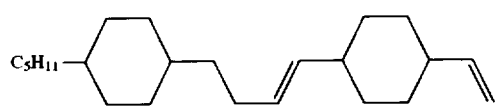 6%
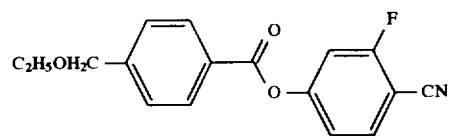 8%
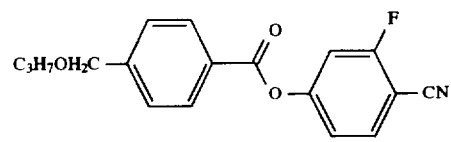 10%
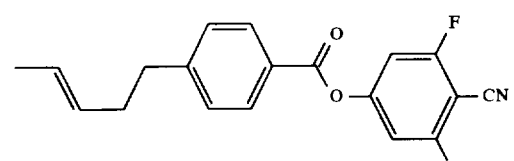 13%
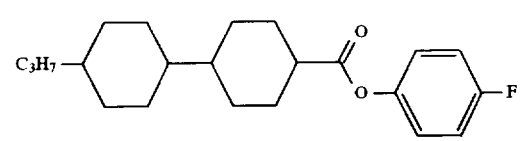 5%
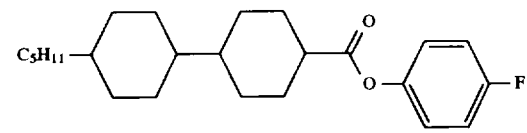 6%
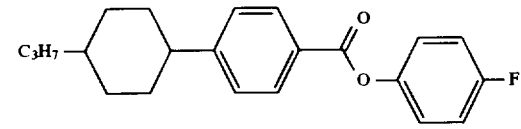 5%
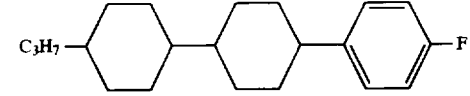 3%
 8%
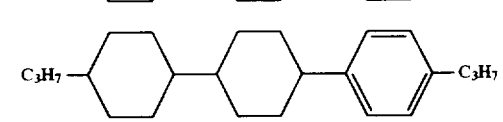 4%
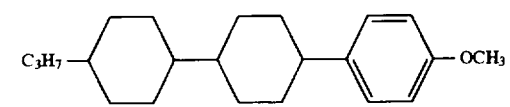 6%
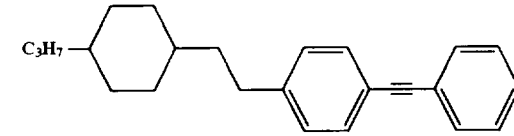 5%
92
-continued
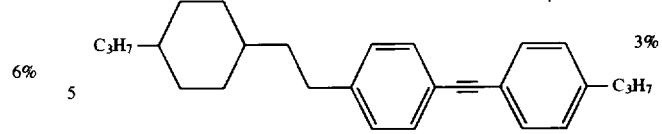 3%
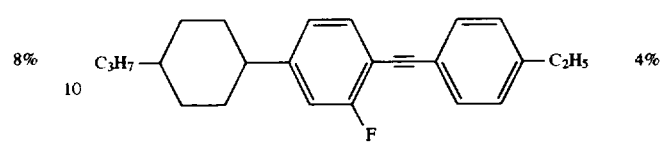 4%
COMPOSITION EXAMPLE 3
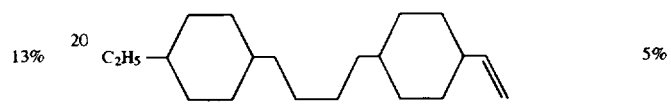 5%
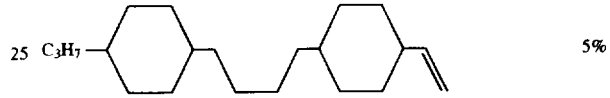 5%
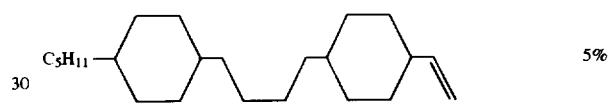 5%
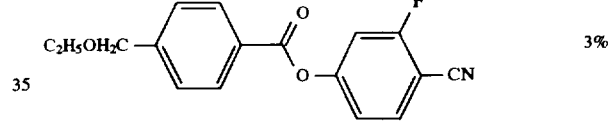 3%
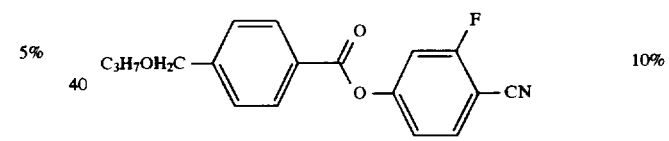 10%
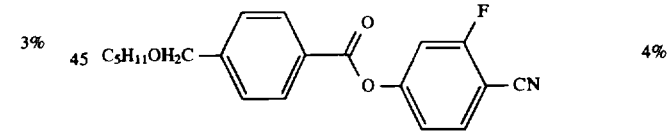 4%
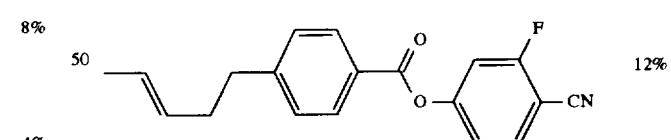 12%
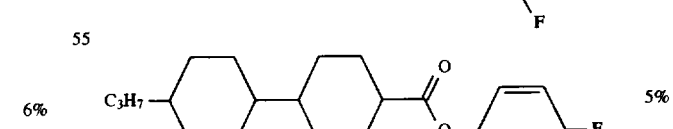 5%
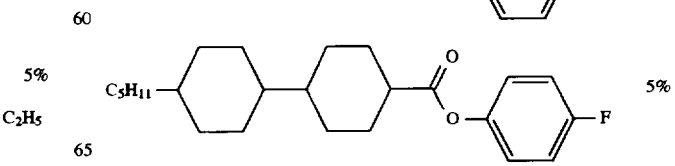 5%

-continued
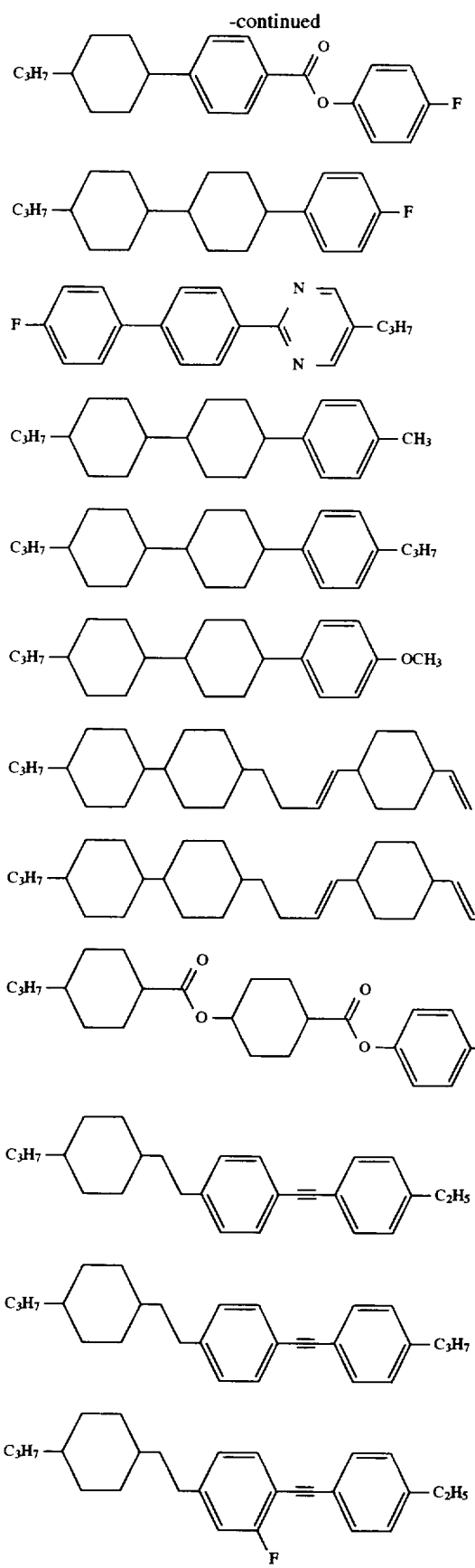
COMPOSITION EXAMPLE 4
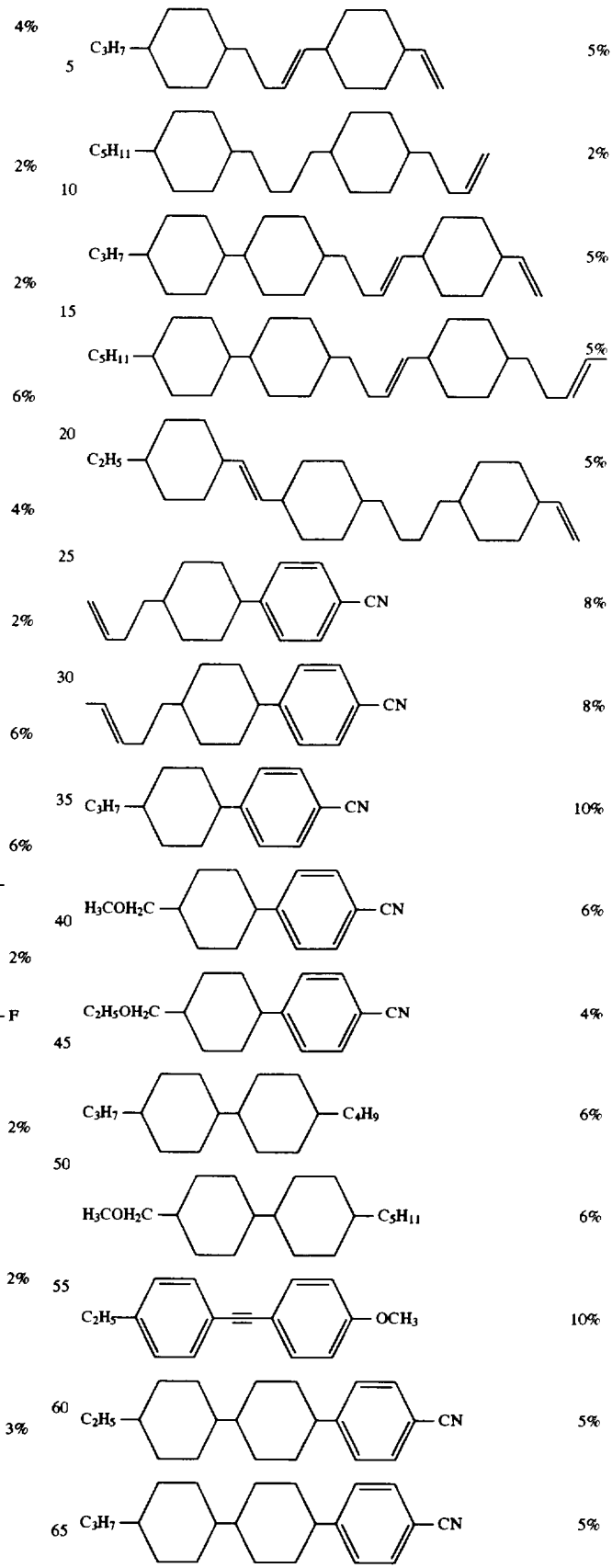

-continued
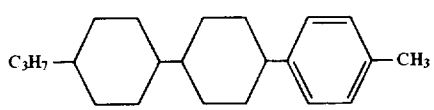 5%
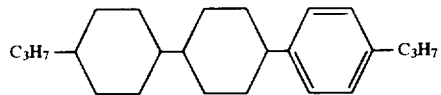 5%
COMPOSITION EXAMPLE 5
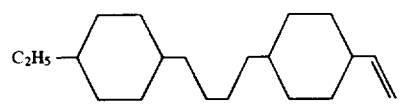 3%
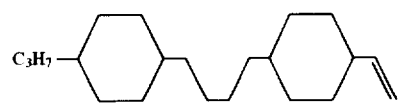 4%
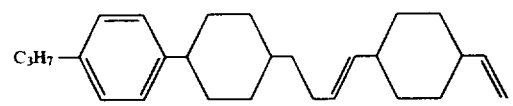 5%
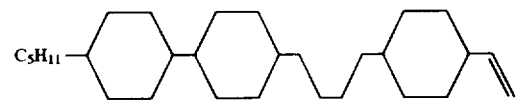 4%
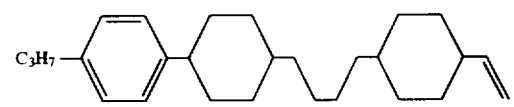 3%
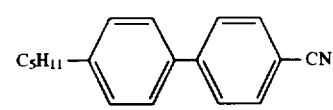 5%
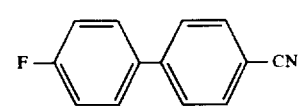 2%
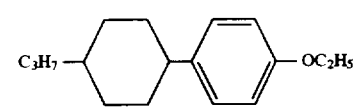 10%
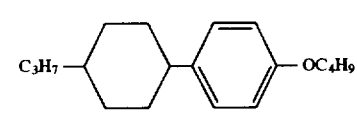 10%
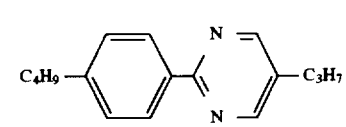 6%
-continued
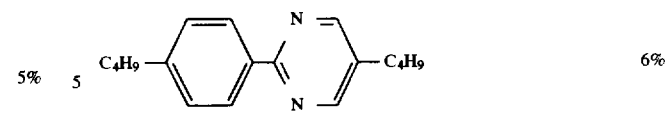 6%
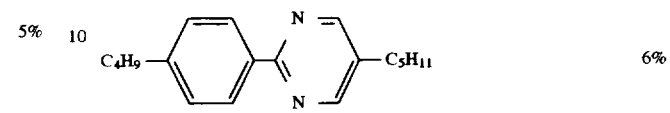 6%
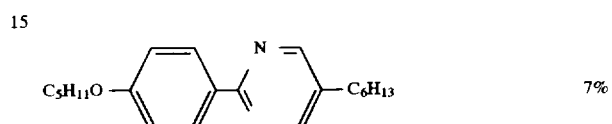 7%
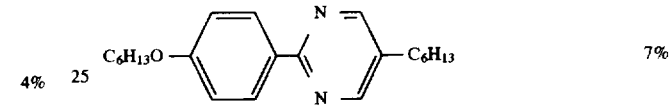 7%
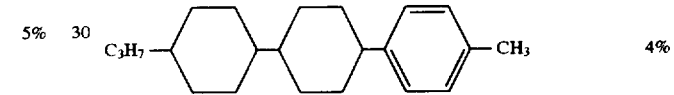 4%
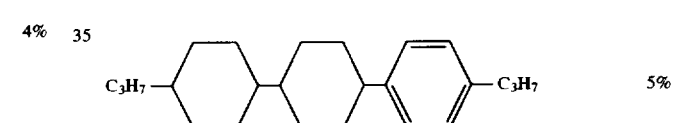 5%
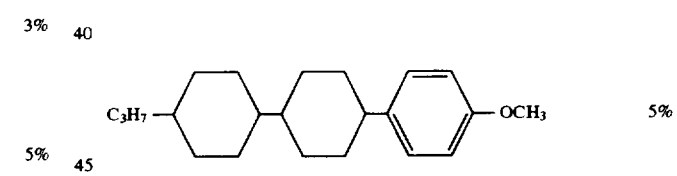 5%
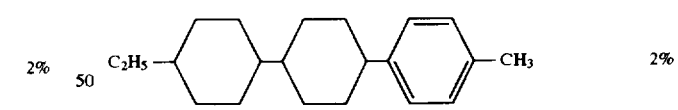 2%
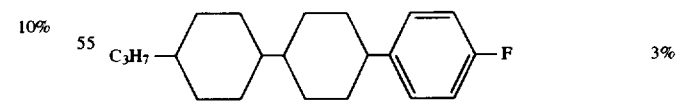 3%
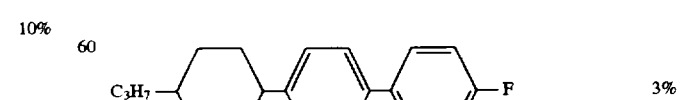 3%

COMPOSITION EXAMPLE 6
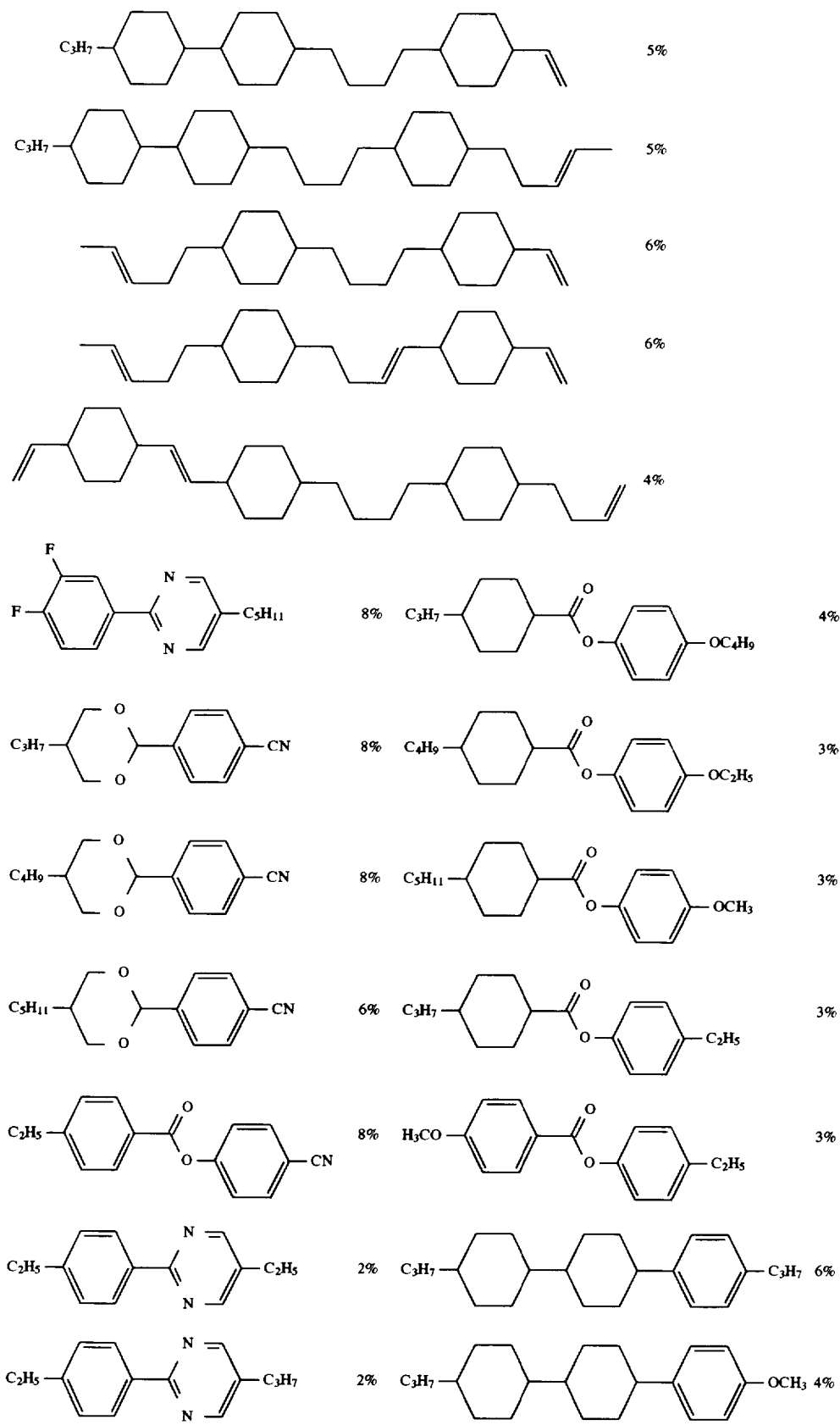

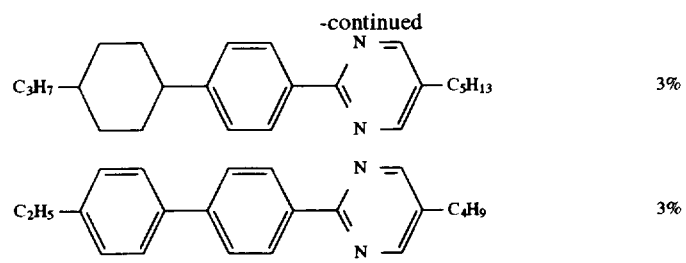
COMPOSITION EXAMPLE 7
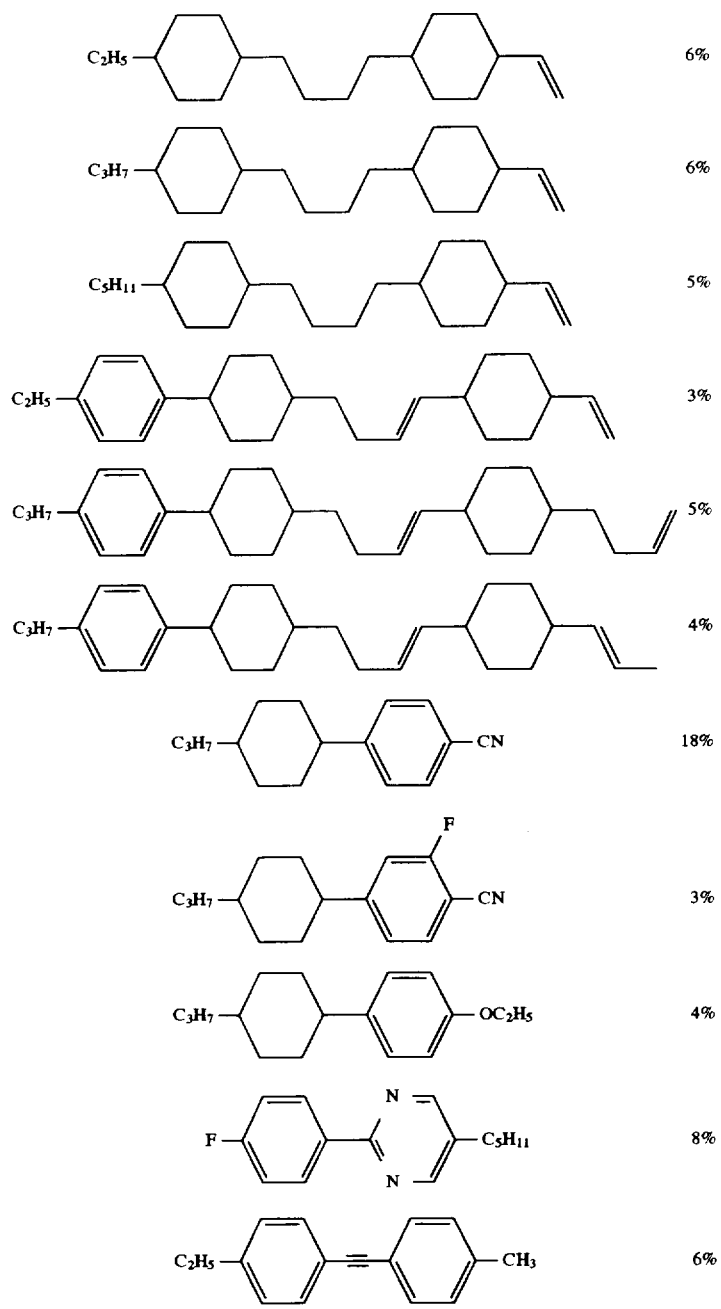

-continued
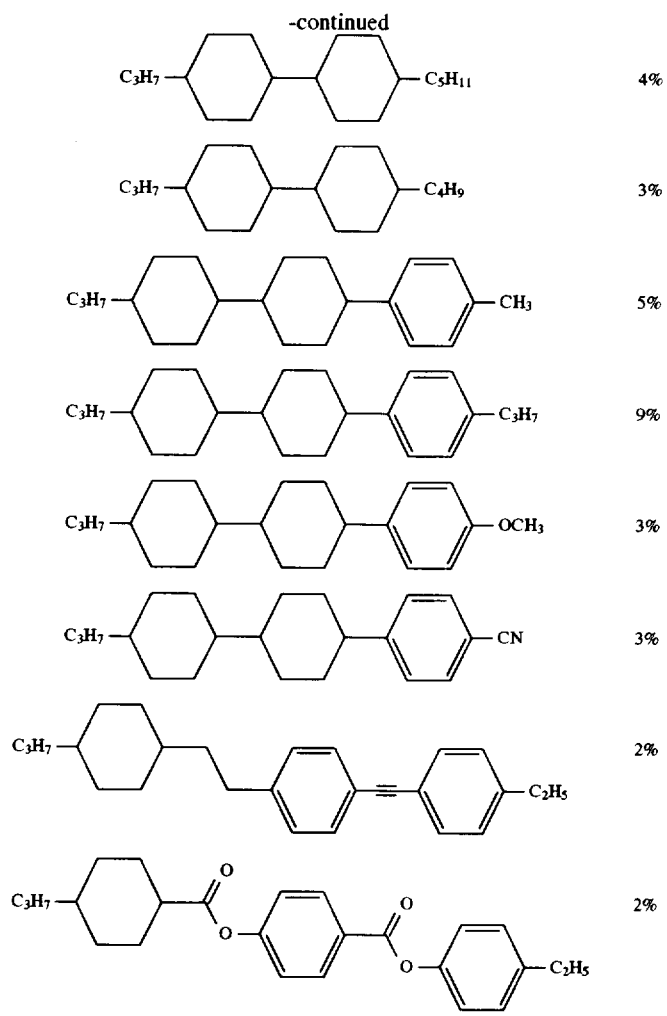
COMPOSITION EXAMPLE 8
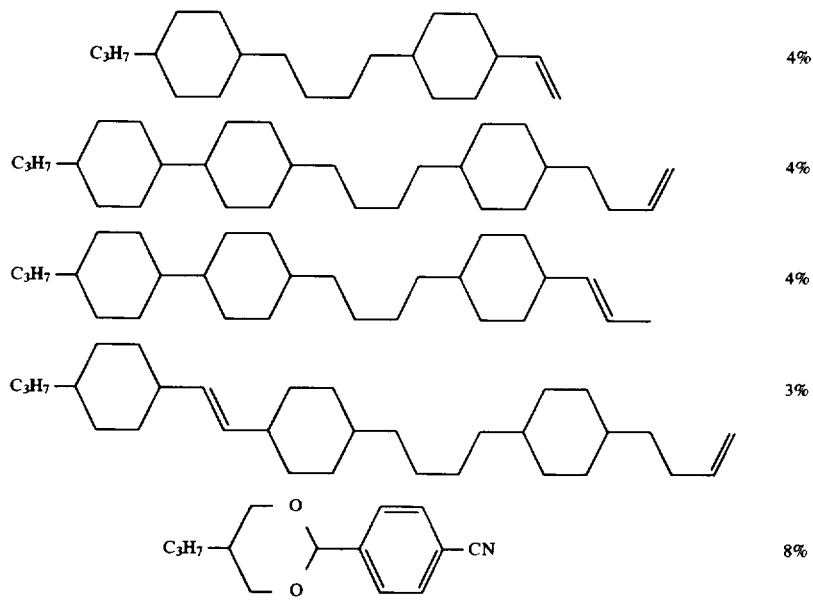

-continued
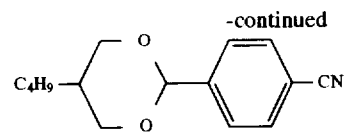 12%
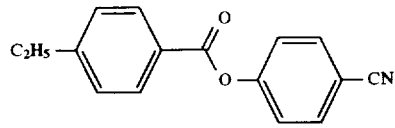 10%
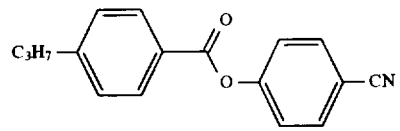 4%
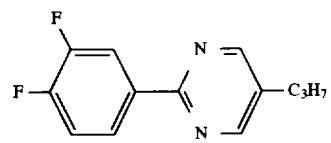 5%
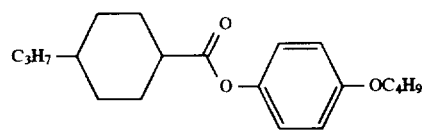 15%
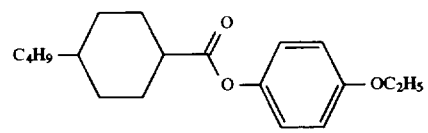 12%
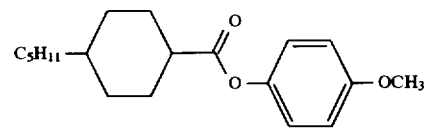 12%
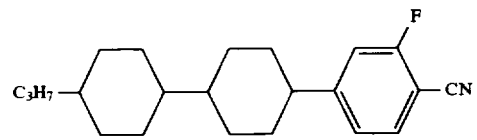 2%
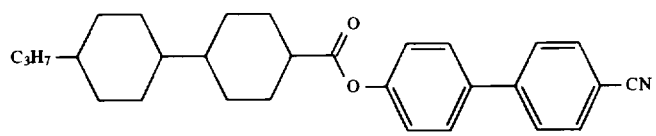 3%
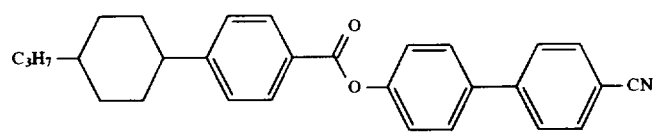 2%
COMPOSITION EXAMPLE 9
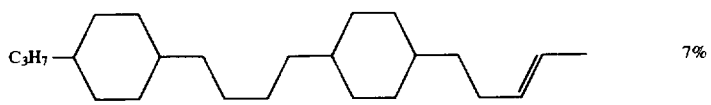 7%

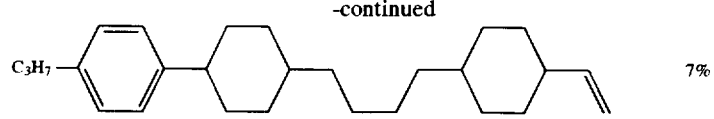 7%
 7%
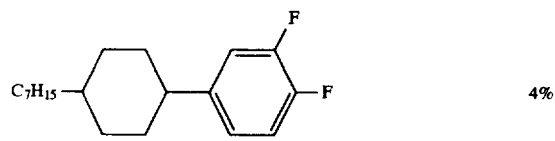 4%
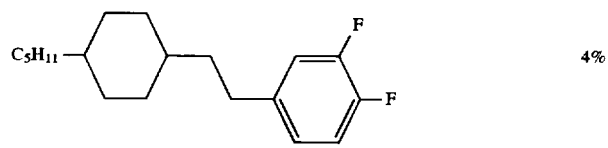 4%
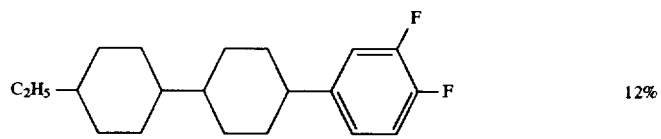 12%
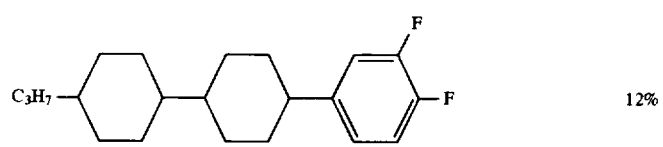 12%
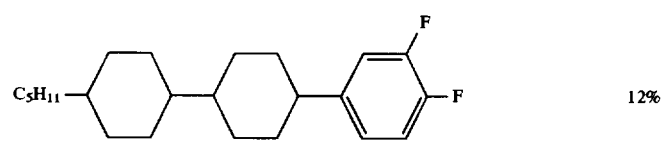 12%
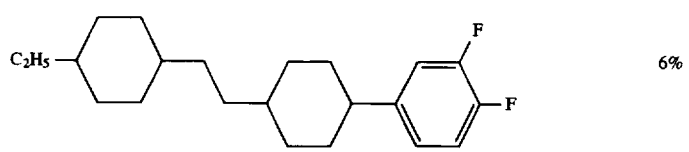 6%
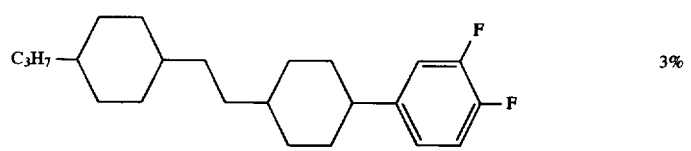 3%
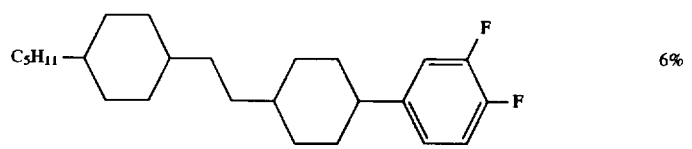 6%
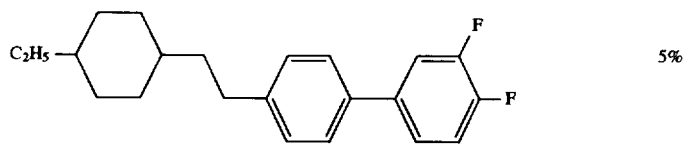 5%

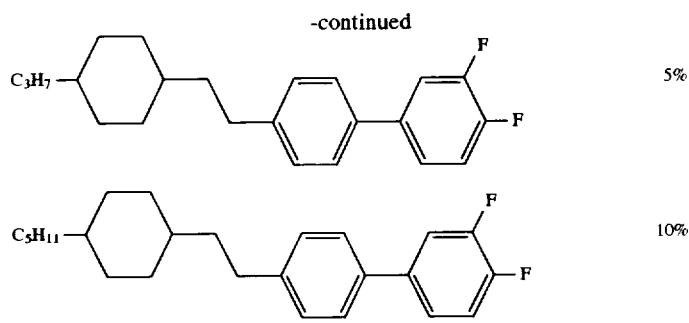
COMPOSITION EXAMPLE 10
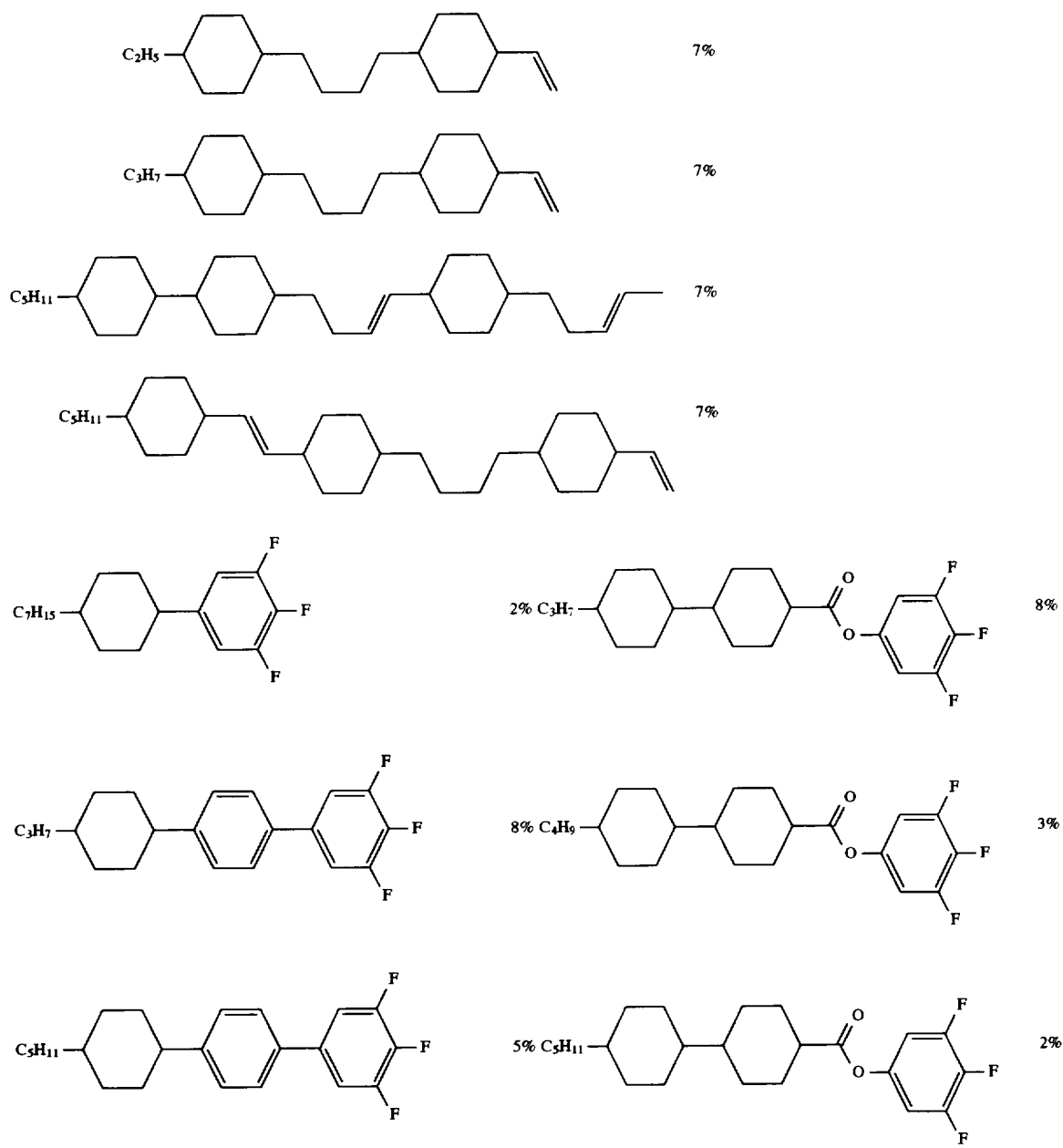

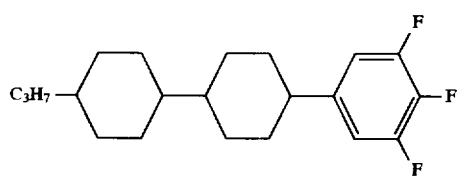
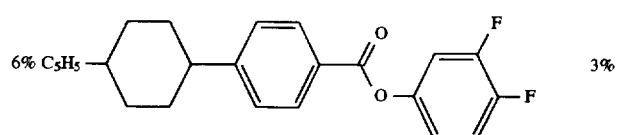 3%
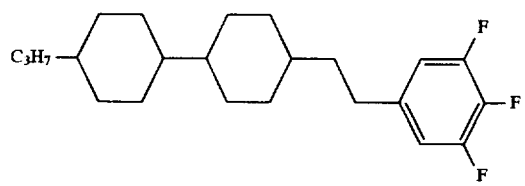
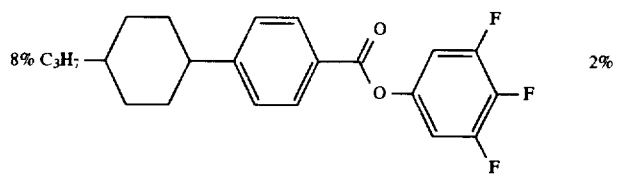 2%
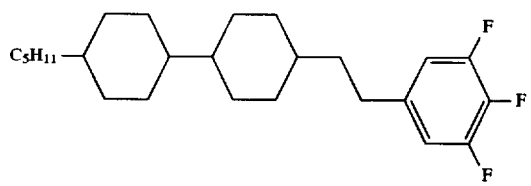
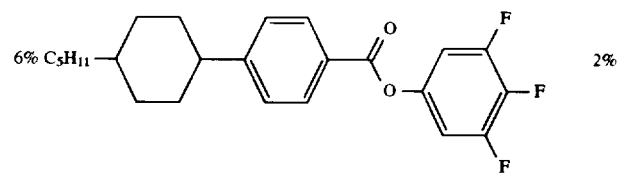 2%
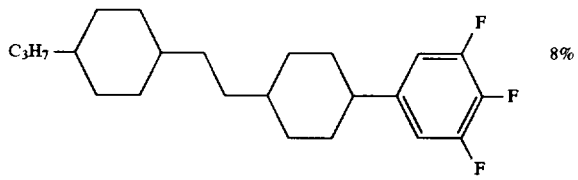 8%
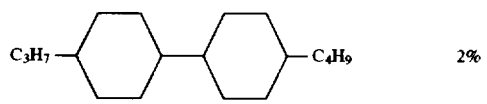 2%
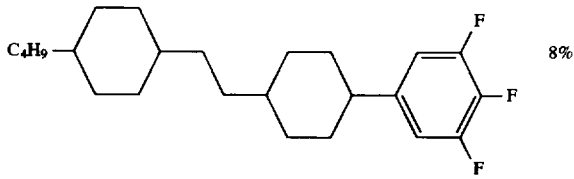 8%
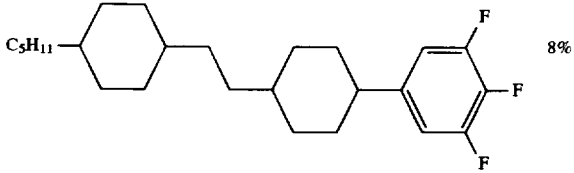 8%
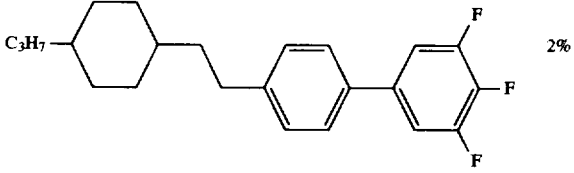 2%
COMPOSITION EXAMPLE 11
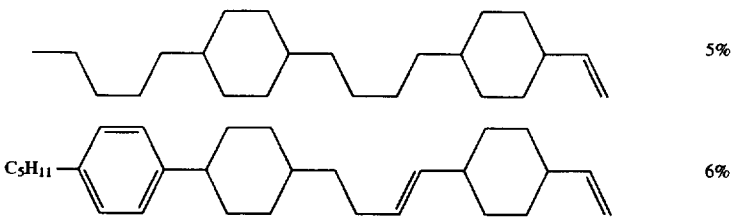

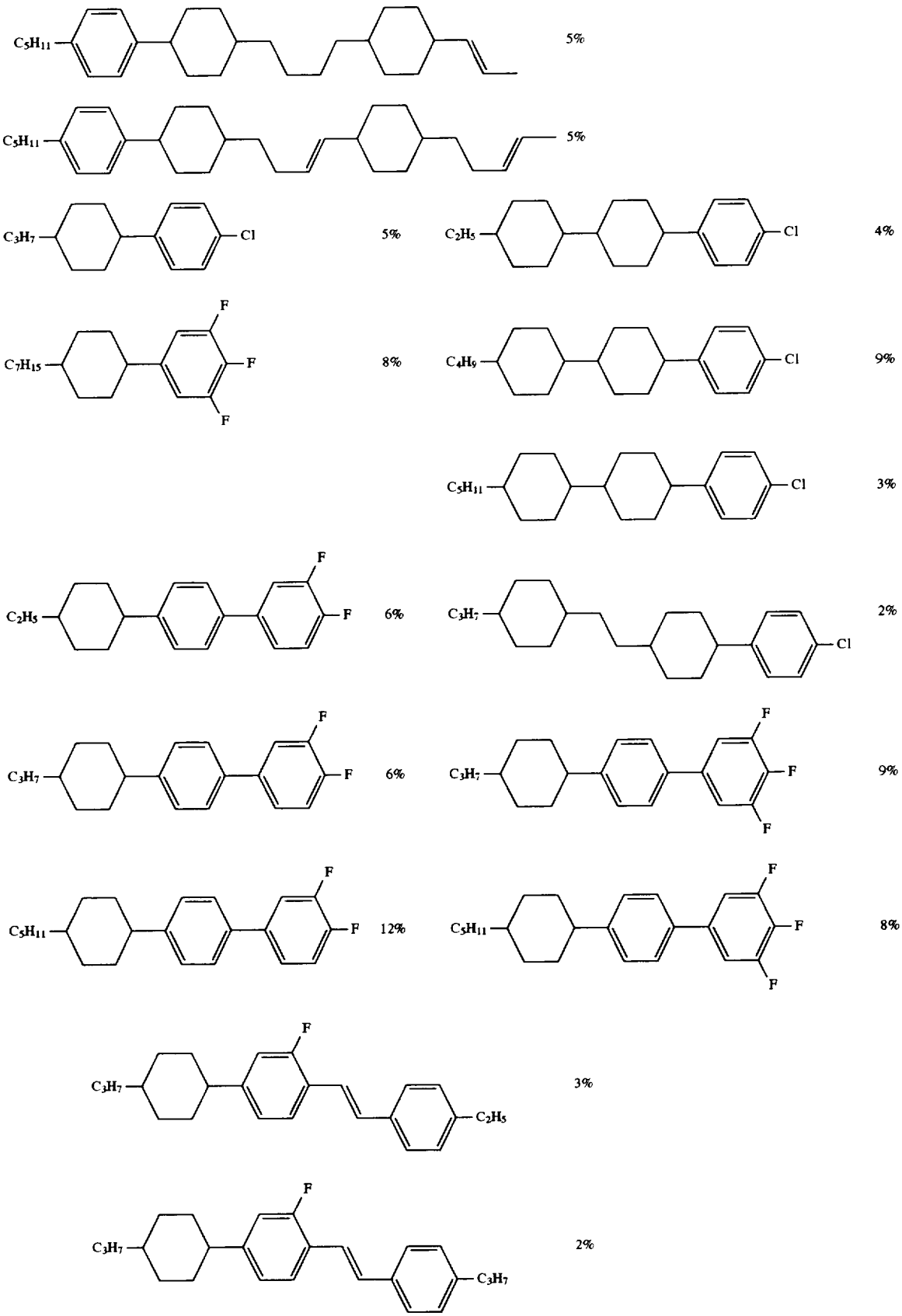

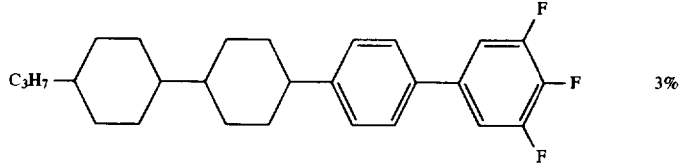
3%
COMPOSITION EXAMPLE 12
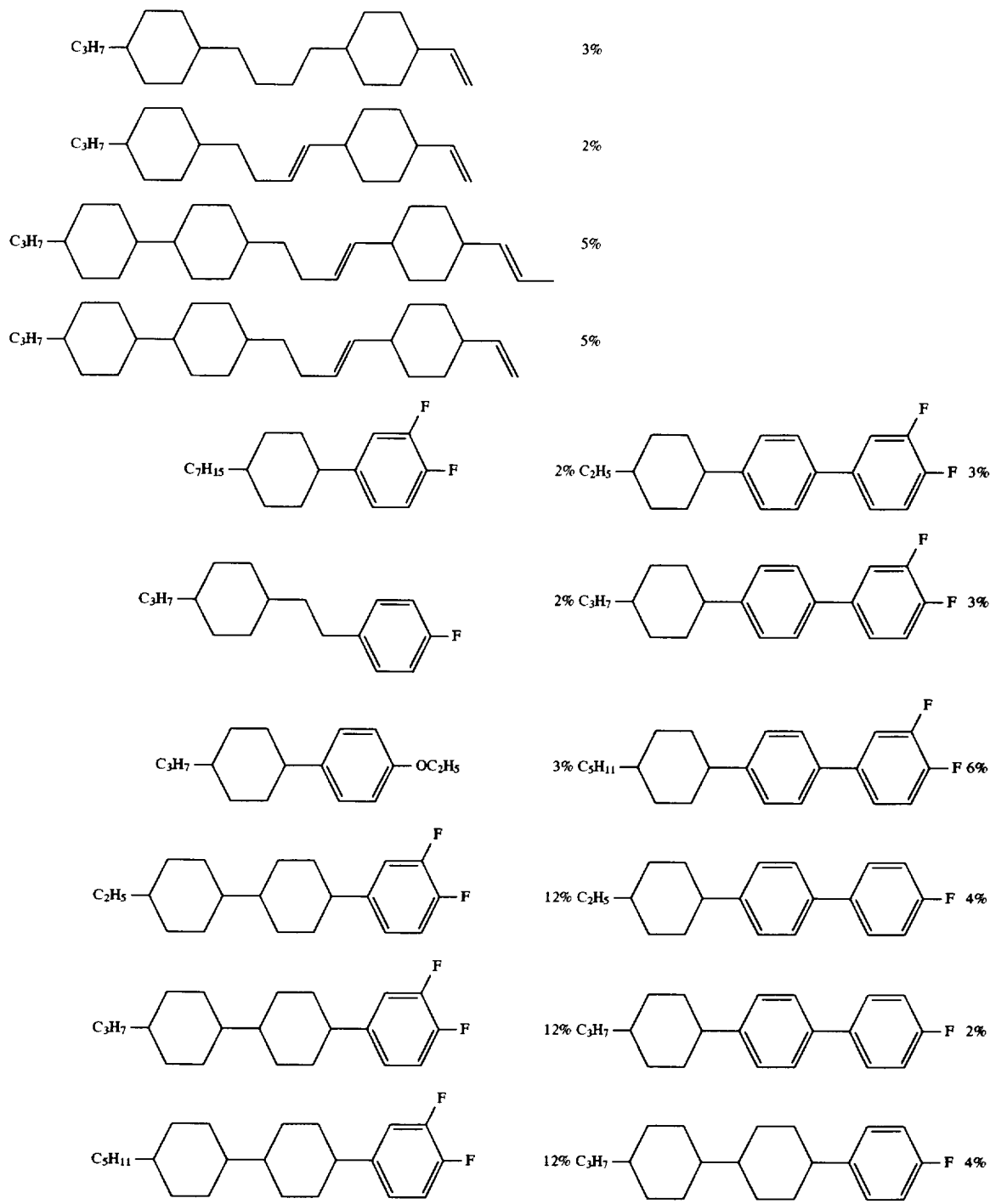

115
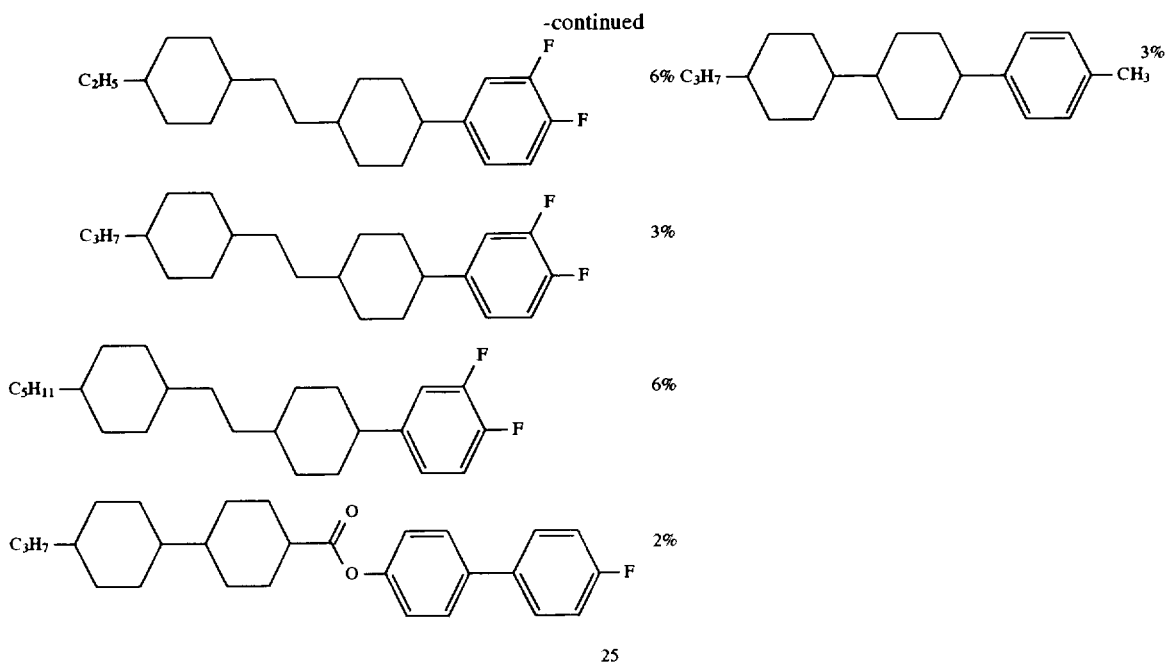
116
COMPOSITION EXAMPLE 13
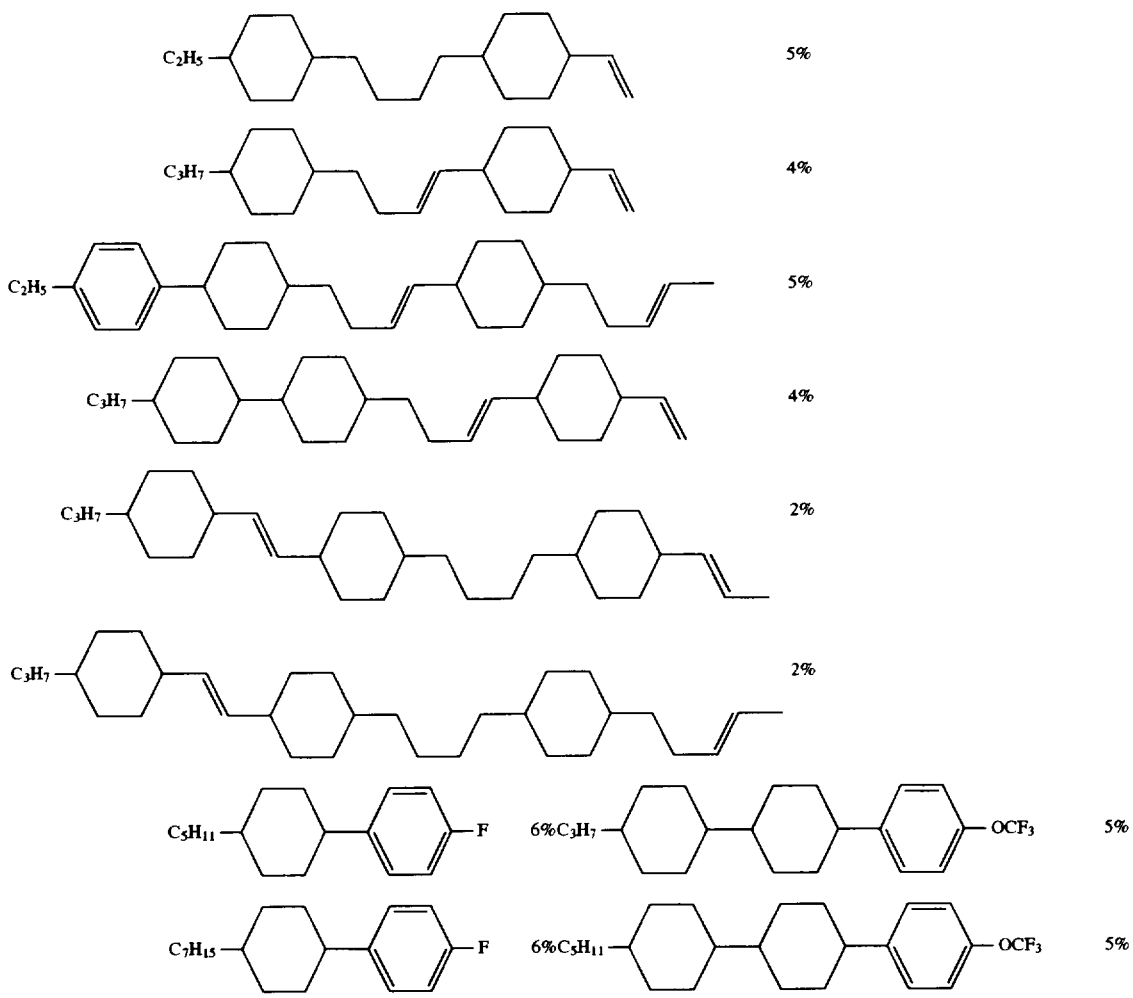

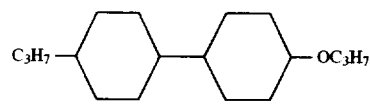
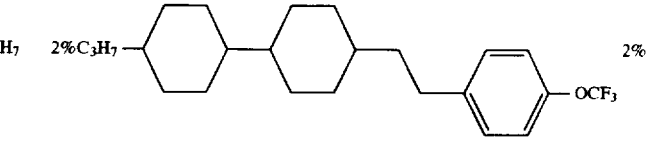 2%
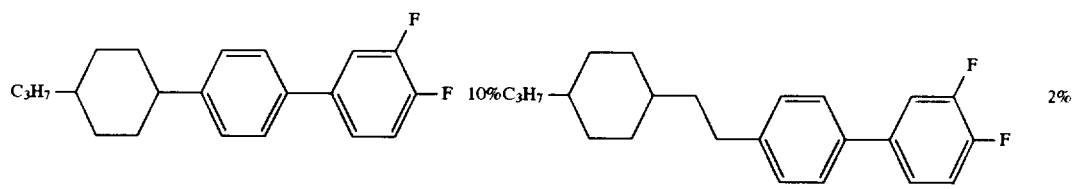 2%
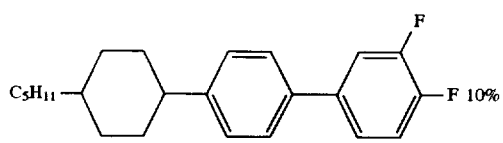 10%
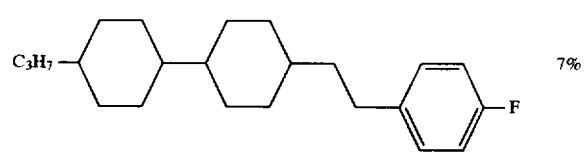 7%
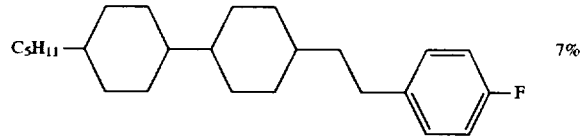 7%
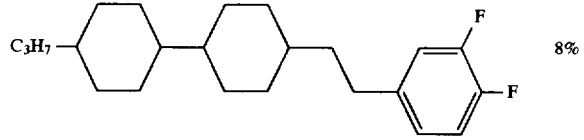 8%
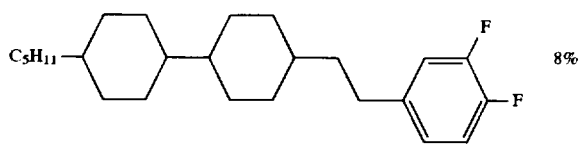 8%
COMPOSITION EXAMPLE 14
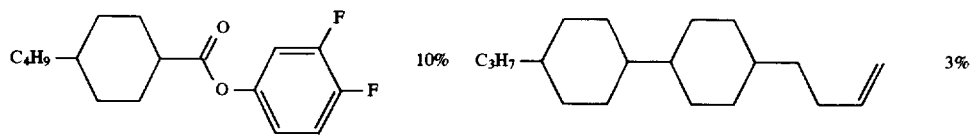
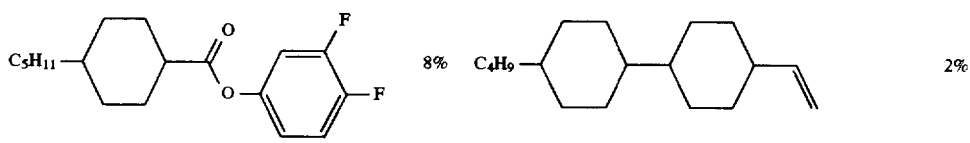
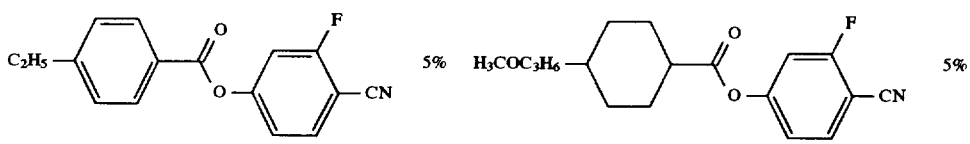

-continued
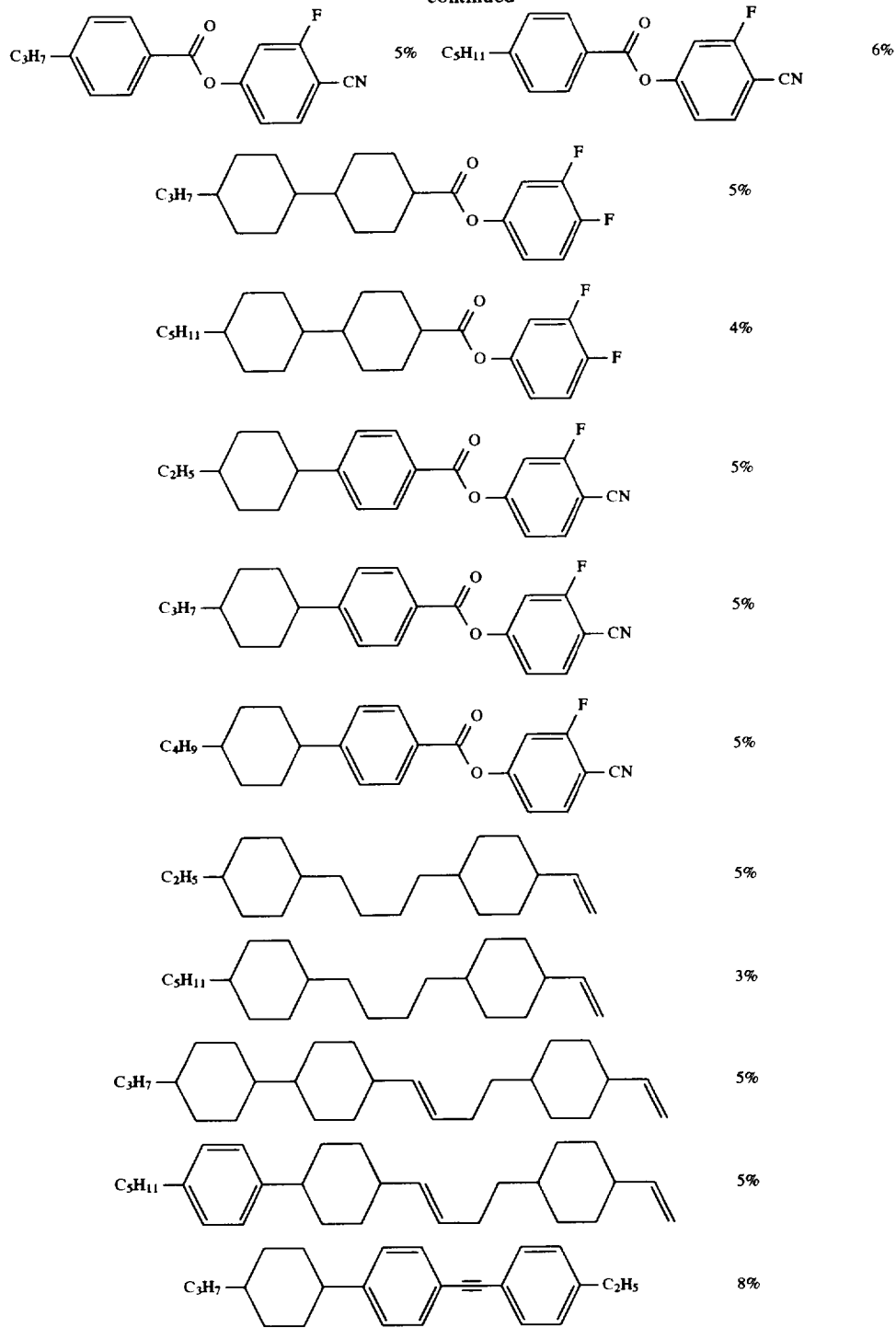
COMPOSITION EXAMPLES 15
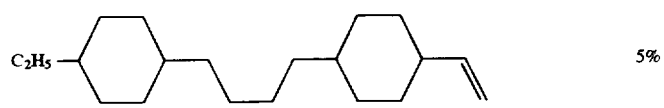

-continued
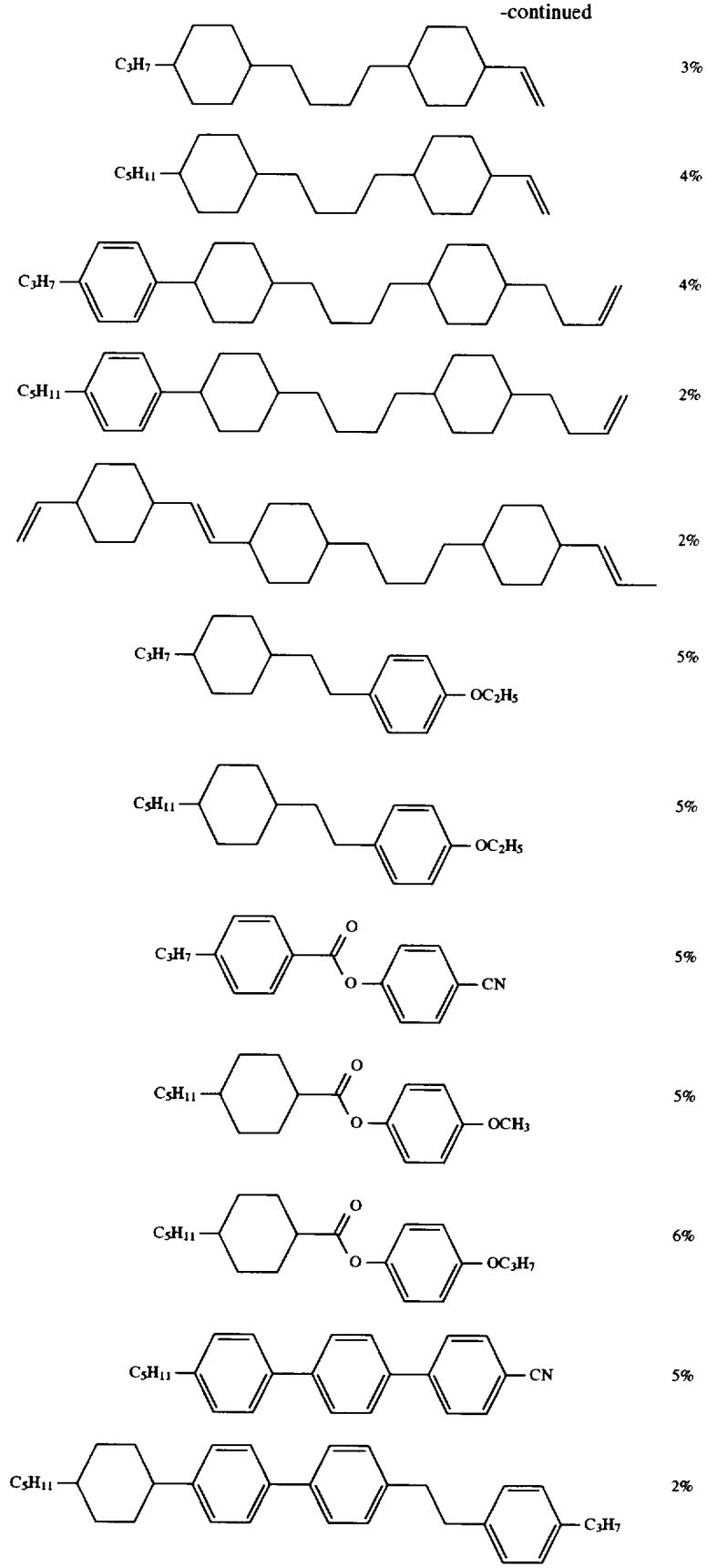
3%
4%
4%
2%
2%
5%
5%
5%
5%
6%
5%
2%

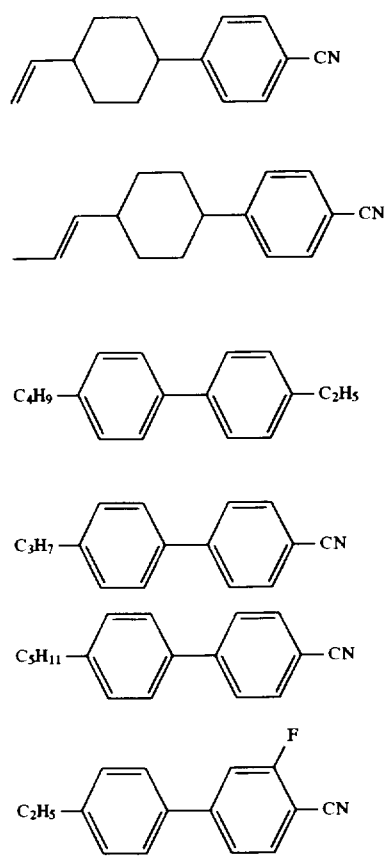

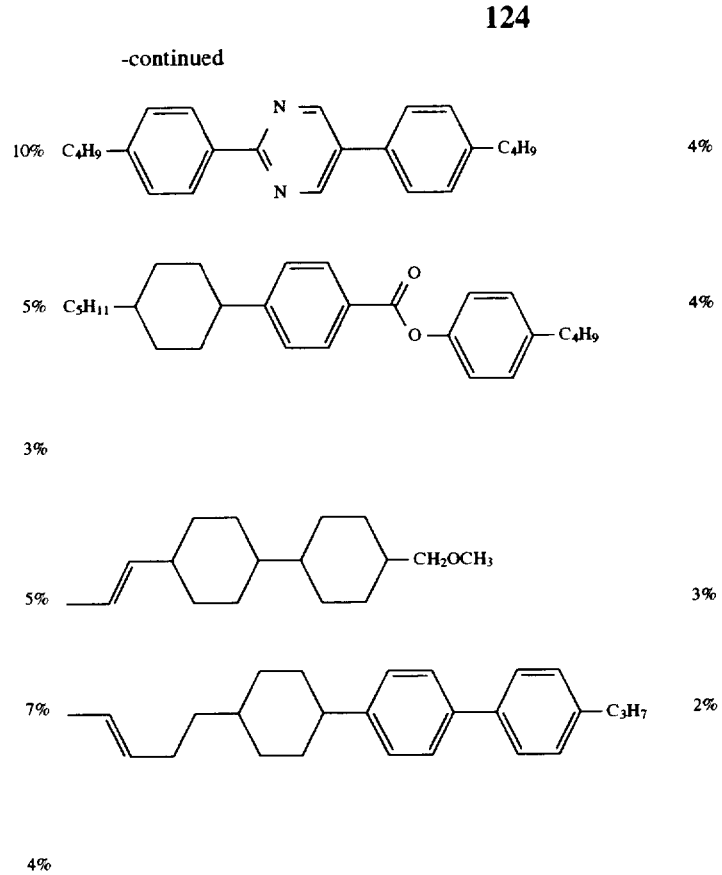

The preparation process of the compound of the present invention will be explained.

Compound expressed by the formula (1-a), mentioned as a preferable compound:

According to a process described in Organic Reaction Vol. 14, Chapter 3, a base such as a sodium alkoxide or an alkyllithium is reacted with a Wittig reagent (11) prepared from a halogenated alkyl, in tetrahydrofuran (hereinafter abbreviated to THF), to prepare a ylide, followed by reacting it with an aldehyde derivative (10). The thus formed E,Z-olefin mixture (12) is reacted with benzenesulfinic acid or p-toluenesulfinic acid according to the process described in Japanese patent publication No. Hei 4-30382, to carry out isomerization, thereby separating E-substance, and resulting in (1-a). Alternatively, E,Z-olefin mixture (2) is reacted with m-chloroperbenzoic acid according to the process described in Japanese patent publication No. Hei 6-62462, to obtain an oxirane derivative (13), followed by reacting dibromotriphenylphosphorane, to prepare a dibromo substance (14), recrystallizing the dibromo substance (14) to purify only erythro substance, and reducing it with metal zinc powder, to prepare (1-a).

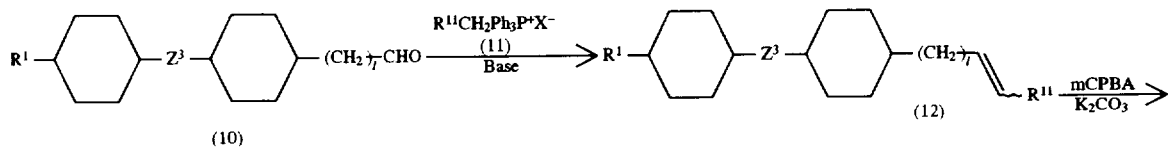

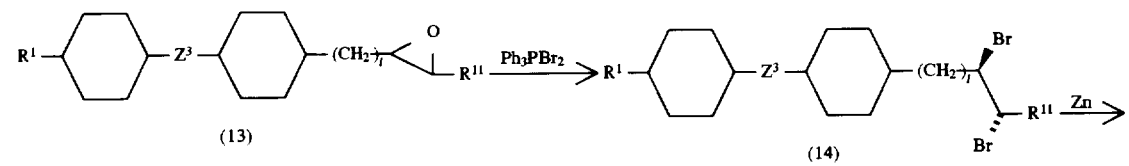

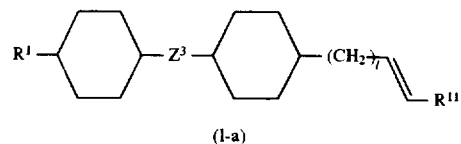

(I-a)

In the above equations, $R^1$ represents a linear or branched alkyl group of 1 to 15 carbon atoms. $R^{11}$ represents hydrogen atom or a linear or branched group of 1 to 15 carbon atoms. $Z^3$ represents —$(CH_2)_4$—, —CH=CH—$(CH_2)_2$—, —$CH_2$—CH=CH—$CH_2$— or —$(CH_2)_2$—CH=CH—, and l represents an integer of 0 to 6.

The aldehyde derivative (10) used as a raw material in the above process can be prepared according to the following process:

A product of $Z^3$=—$(CH_2)_4$—:

A base such as a sodium alkoxide or an alkyllithium is reacted with methoxymethyltriphenylphosphonium chloride in THF to prepare an ylide, followed by reacting a cyclohexanone derivative (15) described in Japanese patent application laid-open No. Hei 5-310605, therewith, to prepare a compound (16), and reacting a mineral acid such as hydrochloric acid, sulfuric acid, etc. or an organic acid such as formic acid, acetic acid, p-toluenesulfonic acid, etc. with the compound (16), to prepare an aldehyde derivative of l=0 (10-1).

Further, a base such as a sodium alkoxide or an alkyllithium is reacted with ethyl diethylphosphinoacetate to prepare an ylide, followed by reacting a cyclohexanone derivative (15) therewith to prepare a compound (17), hydrogenating the compound (17) in the presence of Pd-C catalyst to obtain a compound (18), and reducing it with diisobutylaluminium hydride, to prepare an aldehyde derivative of l=1 (10-2).

Further, a base such as sodium alkoxide, an alkyllithium, etc. is reacted with |2-(1,3-dioxolan-2-yl)-ethyl| triphenylphosphonium bromide to prepare an ylide, and then a cyclohexanone derivative (15) is reacted therewith to prepare a compound (19). This compound (19) is hydrogenated in the presence of Pd-C catalyst to obtain a compound (20), followed by reacting a mineral acid such as hydrochloric acid, sulfuric acid, etc. or an organic acid such as formic acid, acetic acid, p-toluenesulfonic acid, etc. to prepare an aldehyde derivative of l=2 (10-3).

Aldehyde derivatives of l=3 to 6 can be prepared by using aldehyde derivatives (10-1) to (10-3) as synthetic raw materials, and subjecting the materials to repetitions or combinations of the above three kinds of carbon number-increasing reaction process.

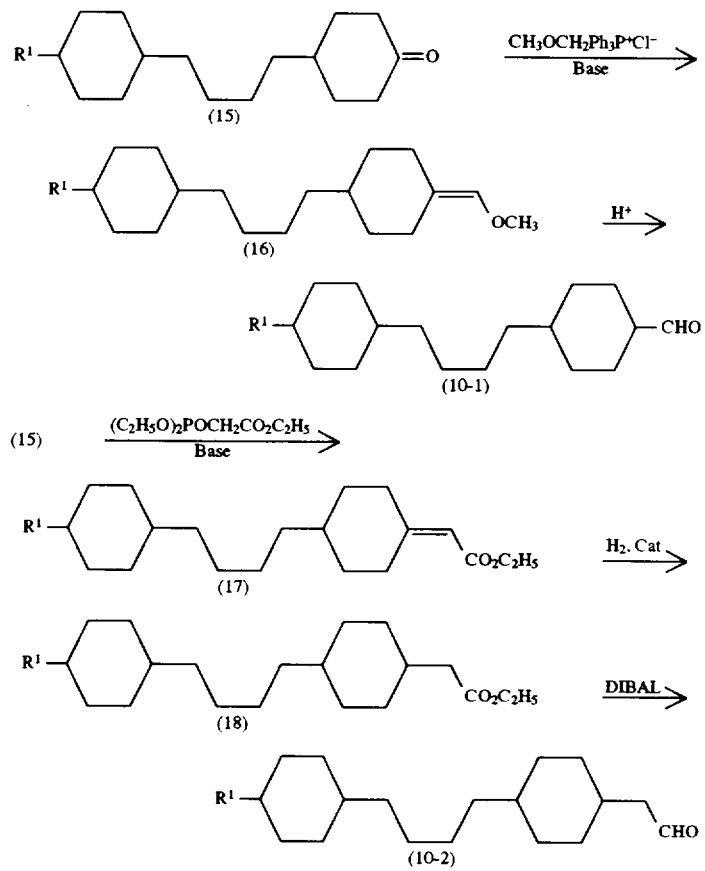

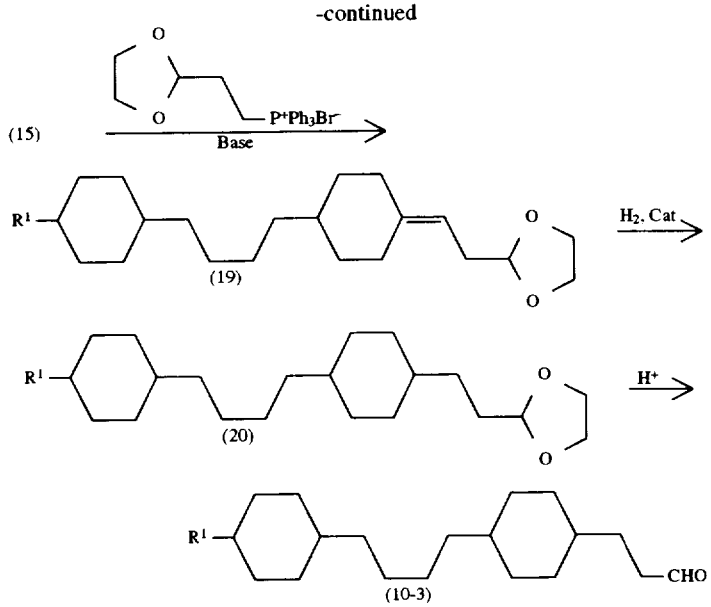

In these equations, R¹ is as defined above.

A product of $Z^3$=—$(CH_2)_2$—CH=CH—:

A base such as a sodium alkoxide, an alkyllithium, etc. is reacted with a Wittig reagent (23) prepared according to the synthesis process described in Japanese patent application laid-open No. Hei 6-40968, to prepare an ylide, followed by reacting therewith 4-formylcyclohexanone (22) prepared from 1,4-cyclohexanedione monoethyleneketal (21) according to the synthesis process described in Japanese patent publication No. Hei 4-30382, to prepare a butenylcyclohexanone derivative (24). This derivative (24) is isomerized according to the process described in the above Japanese patent publication No. Hei 4-30382 or in Japanese patent publication No. Hei 6-62482, and E-butenyl derivative is separated. The E-butenyl derivative is subjected to a carbon-number increasing reaction process same as that having lead the above cyclohexanone derivative (15) to the aldehyde derivative (10-1), to prepare an aldehyde derivative (10-4)

A product of $Z^3$=—$CH_2$—CH=CH—$CH_2$—:

A base such as a sodium alkoxide, an alkyllithium, etc. is reacted with ethyl diethylphosphinoacetate to prepare an ylide, followed by reacting therewith, 1,4-cyclohexanedione monoethylene ketal (21), to prepare a compound (25), hydrogenating this compound (25) in the presence of Pd-C catalyst, successively reducing it with hydrogenated diisopropylaluminum, to prepare a compound (26). This compound (26) is reacted with an ylide prepared by reacting a base such as a sodium alkoxide, an alkyllithium, etc. with a Wittig reagent (27) prepared according to the synthetic process described in Japanese patent application laid-open No. Hei 6-40968, to prepare a compound (28). This compound (28) is reacted with a mineral acid such as hydrochloric acid, sulfuric acid, etc., or an organic acid such as formic acid, acetic acid, p-toluenesulfonic acid, etc., to prepare a butenylcyclohexanone derivative (29), and then subjecting it to a carbon number-increasing process same as that having led from the above cyclohexanone derivative (15) to the aldehyde derivative (10-1), to prepare an aldehyde derivative (10-5).

A product of $Z^3$=—CH=CH—$(CH_2)_2$—:

A base such as sodium alkoxide, an alkyllithium, etc. is reacted with [2—(1,3-dioxolan-2-yl)ethyl] triphenylphosphonium bromide, to prepare an ylide, followed by reacting therewith, 1,4-cyclohexanedione monoethylene ketal (21), to prepare a compound (30). The compound (30) is hydrogenated in the presence of Pd-C catalyst, successively reacting with the resulting substance, a mineral acid such as hydrochloric acid, sulfuric acid, etc. or an organic acid such as formic acid, acetic acid, p-toluenesulfonic acid, etc., to prepare a cyclohexanone derivative (31). This cylohexanone derivative (31) is reacted with an ylide prepared by reacting a base such as a sodium alkoxide, an alkyllithium, etc. with a Wittig reagent (32) prepared according to a synthetic process described in Japanese patent application laid-open No. Hei 6-40968, to prepare a compound (33), isomerizing it according to the process described in the above Japanese patent publication No. Hei 4-30382 or Japanese patent publication No. Hei 6-62462, to prepare a E-butenyl derivative. A compound (33) consisting only of the E-butenyl derivative is subjected to a carbon number-increasing reaction process same as that having led the above cyclohexanone derivative (15) to the aldehyde derivative (10-1), to prepare an aldehyde derivative (10-6).

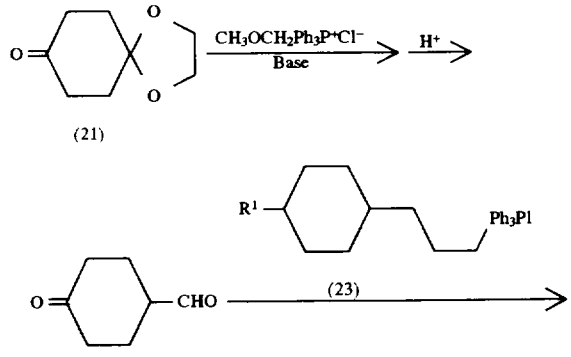

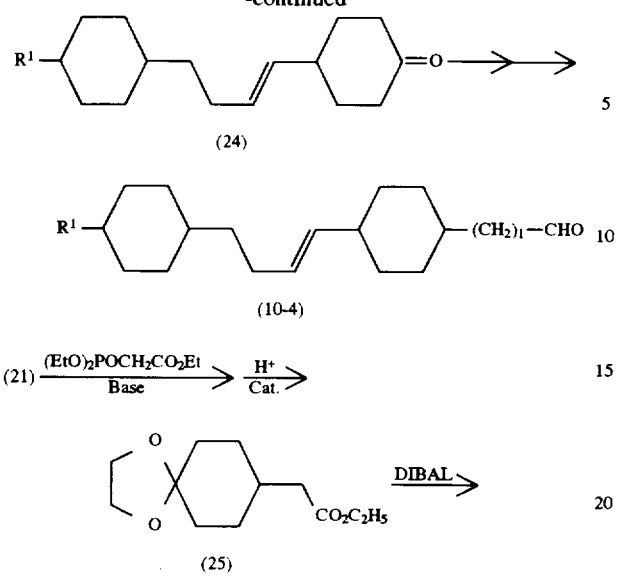

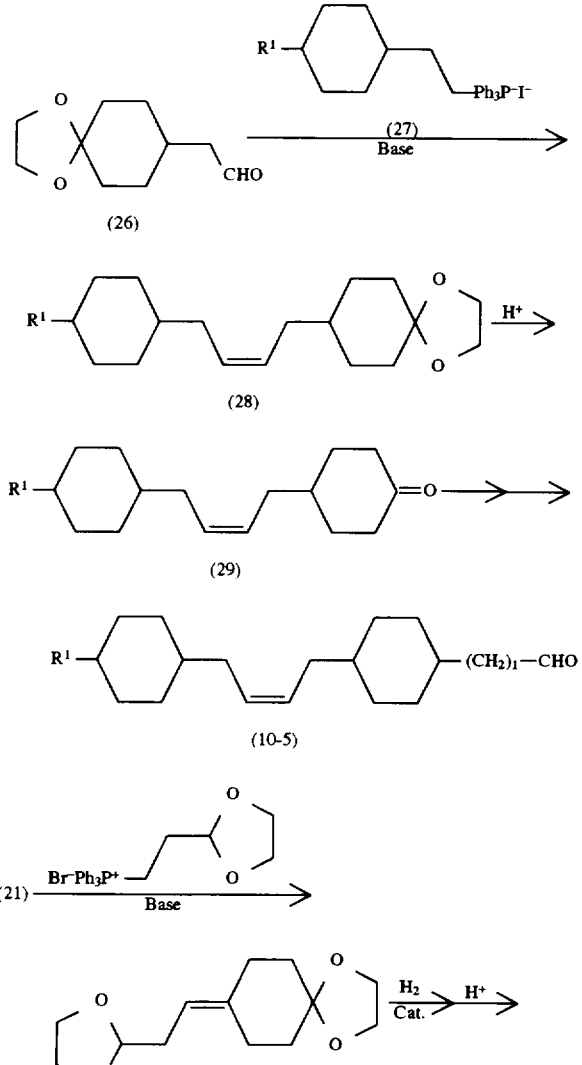

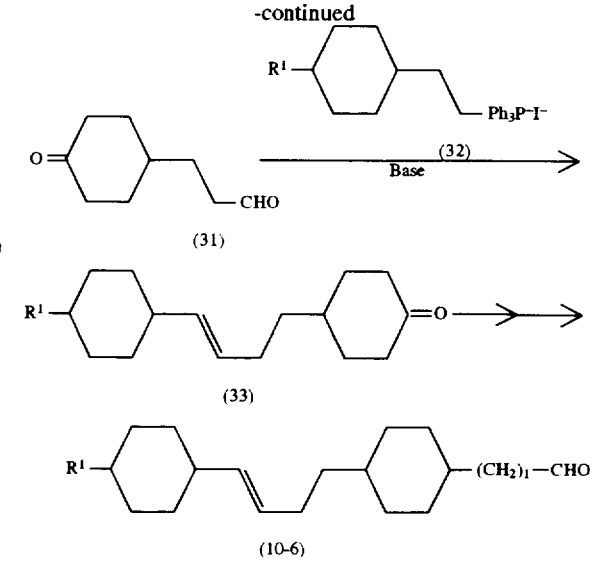

In these equations, $R^1$ and l are as defined above.

In the compound expressed by the formula (1-a) the compound (1-a-a) wherein $R^1$ is an alkenyl compound can be prepared according to the following process:

4-Methoxycyclohexanecarboxylic acid (34) is reduced with lithium aluminum hydride up to an alcohol substance, followed by brominating it with carbon tetrabromide-triphenylphosphine or hydrogen bromide acid according to a known process such as that of P. J. Kocienski et al (J. Org. Chem. 42, 353 (1977)), to prepare a bromide (35). The bromide (35) is reacted wit h triphenylphosphine according to a process described in Organic Reaction, Vol. 14, Chapter 3, to prepare a Wittig reagent (36), then reacting therewith a base such as a sodium alkoxide, an alkyllithium, etc., to prepare an ylide. This ylide is reacted with a compound (31a) to prepare a compound (37). This (37) is subjected to a carbon atom-increasing reaction process as that having led the above cyclohexane derivative (15) to the aldehyde derivative (10-1), and then an isomerization process same as that in the case of preparation of the compound (1-a), to prepare a compound (38). The compound (38) is reacted with boron tribromide in dichloromethane to effect demethylation, treating the resulting substance with a suitable oxydizing agent such as sodium hypochloride, etc. to obtain a compound (39), and subjecting the compound (39) to a carbon number-increasing reaction same as that having led the above cyclohexanone derivative (15) to the aldehyde derivative (10-1), to obtain a compound (40), and further subjecting the compound (40) to the same synthetic process as that in the case of preparation of the compound (1-a), to obtain a compound (1-a-a).

Compounds of $Z^3=$—$(CH_2)_2$—$CH=CH$— or —$CH_2$—$CH=CH$—$CH_2$—, too, can be prepared by suitably selecting the starting substance in the above reaction.

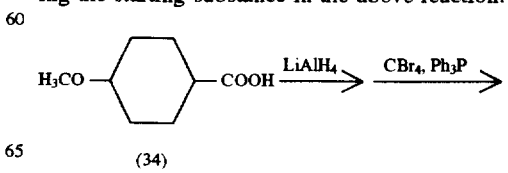

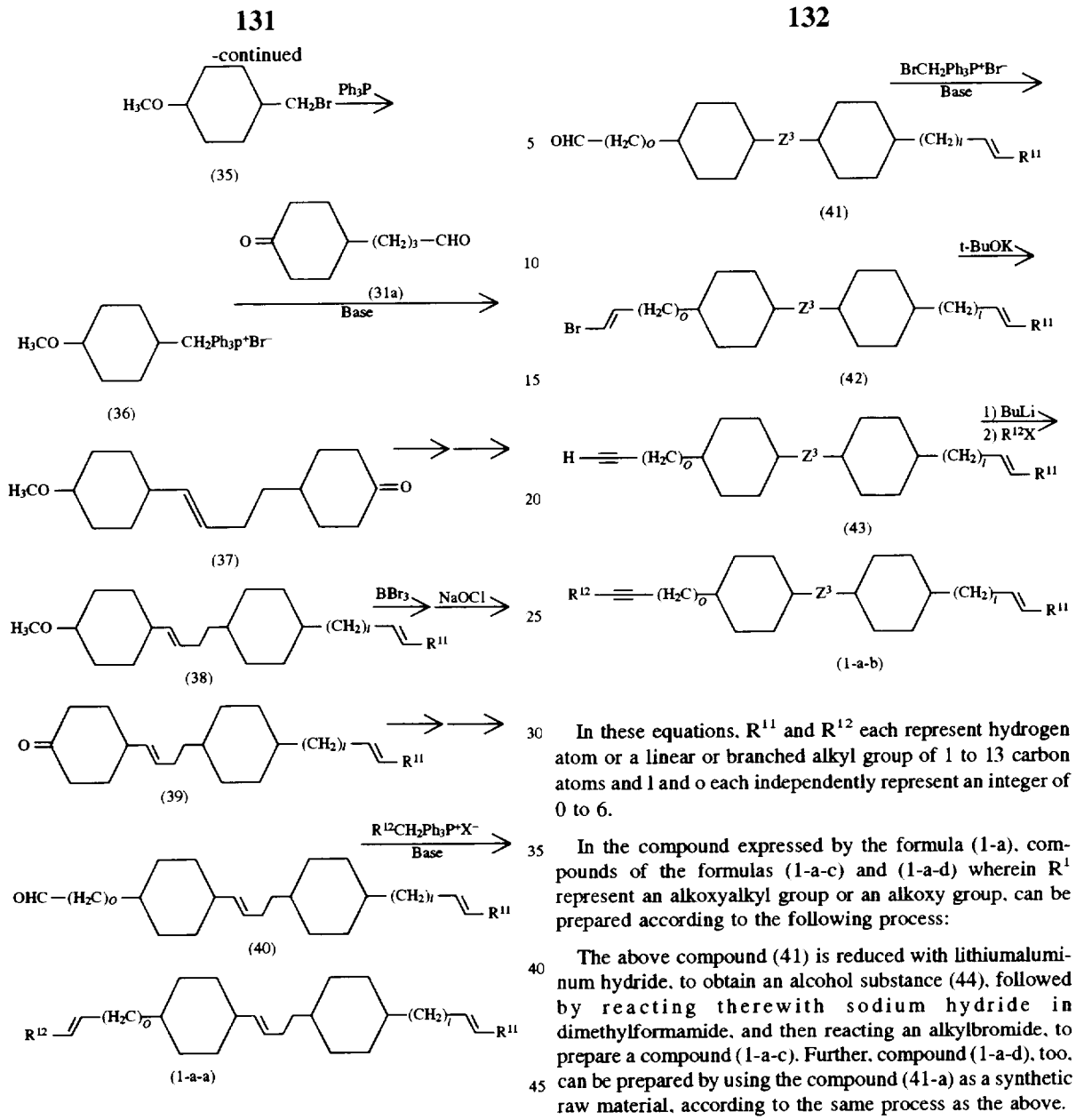

In the above equations, $R^{11}$ and $R^{12}$ each represent hydrogen atom or a linear or branched alkyl group of 1 to 13 carbon atoms, and l and o each independently represent an integer of 0 to 6.

In the compound expressed by the formula (1-a), a compound of the formula (1-a-b) wherein $R^1$ represents an alkynyl group can be prepared according to the following process:

Bromomethyltriphenylphosphine bromide and an ylide prepared from a suitable base are reacted with a compound (41) prepared by the same process as that in the case of the above compound (40), according to the process described in Japanese patent publication No. Hei 4-30382, to obtain a compound (42), followed by reacting therewith potassium-t-butoxide, to prepare a compound (43). The compound (43) is treated with n-butyllithium and reacted with an alkyl bromide, to prepare the compound (1-a-b).

In these equations, $R^{11}$ and $R^{12}$ each represent hydrogen atom or a linear or branched alkyl group of 1 to 13 carbon atoms and l and o each independently represent an integer of 0 to 6.

In the compound expressed by the formula (1-a), compounds of the formulas (1-a-c) and (1-a-d) wherein $R^1$ represent an alkoxyalkyl group or an alkoxy group, can be prepared according to the following process:

The above compound (41) is reduced with lithiumaluminum hydride, to obtain an alcohol substance (44), followed by reacting therewith sodium hydride in dimethylformamide, and then reacting an alkylbromide, to prepare a compound (1-a-c). Further, compound (1-a-d), too, can be prepared by using the compound (41-a) as a synthetic raw material, according to the same process as the above.

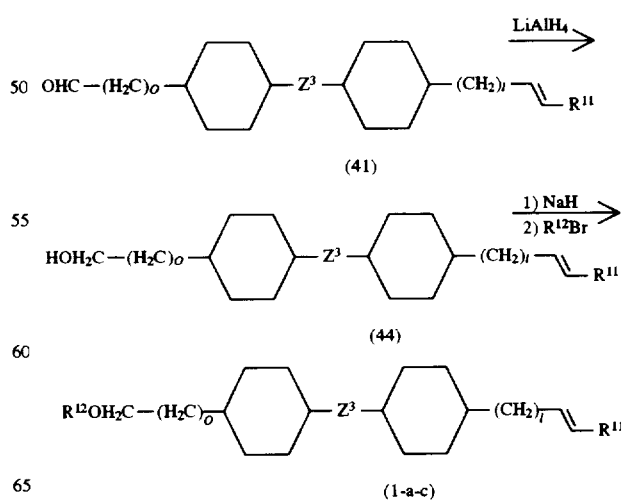

133

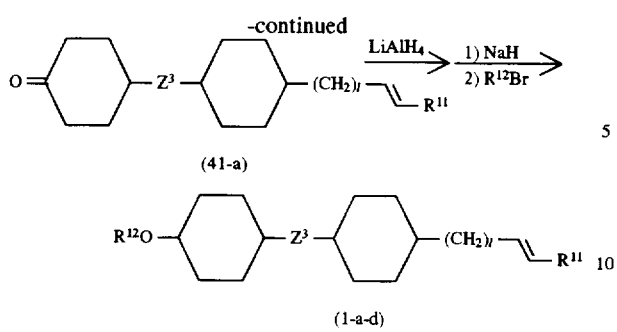

(41-a)

(1-a-d)

In these equations, $R^{11}$ and $R^{12}$ each represent hydrogen atom or a linear or branched alkyl group of 1 to 13 carbon atoms and l and o each independently represent an integer of 0 to 6.

The compounds expressed by the formula (1-b), mentioned as preferable compounds, can be prepared according to the following process:

A cyclohexanone derivative (45) is subjected to the same process as that having led the above compound (21) to the compound (24), the compound (29) and the compound (33), to prepare a compound (46) and subjecting the compound (46) to a carbon atom-increasing reaction process same as that having led the above cyclohexanone derivative to the aldehyde derivative (10-1), to prepare an aldehyde derivative (47). Next, the aldehyde derivative (47) is subjected to a Wittig reaction with an alkyltriphenyl-phosphine halide, in the same manner as in the case of preparation of the compound (1-a), to obtain the compound (1-b).

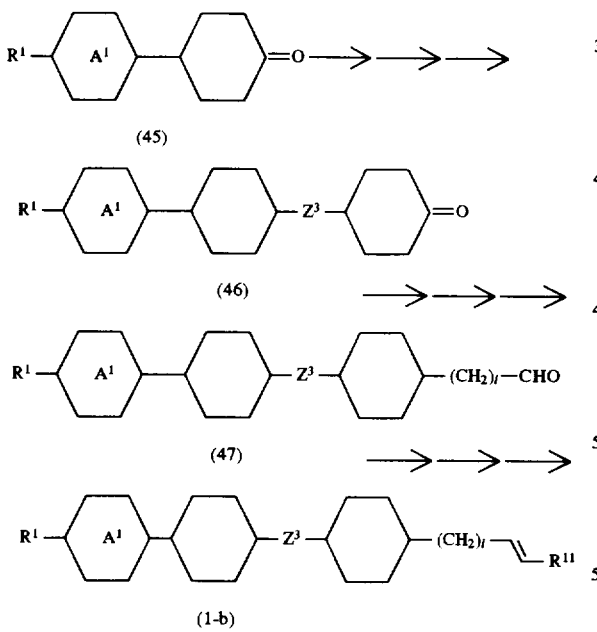

In these equations, $R^1$, ring $A^1$ and $Z^3$ are as defined above; $R^{11}$ represents hydrogen atom or a linear or branched alkyl group of 1 to 13 carbon atoms; and l and o each independently represent an integer of 0 to 6.

Compound wherein ring $A^1$ is 1,3-dioxane-2,5-diyl:

Using p-toluenesulfonic acid or a non-hydroxyl ion-exchange resin such as Amberlist, etc. as catalyst, the aldehyde derivative (22) is reacted with a diol derivative

134

(48), or an aldehyde derivative (49) is reacted with a diol derivative (50), to prepare compounds (45-a) or (45-b).

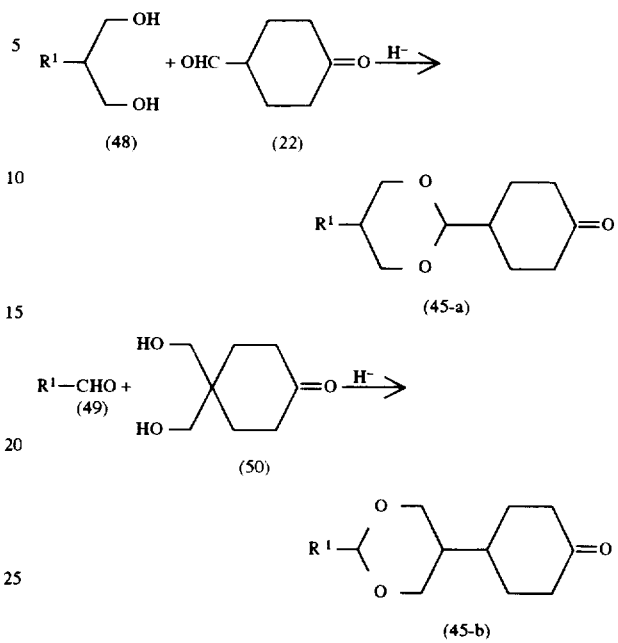

In these equations, $R^1$ is as defined above.

The compound of the formula (1c), mentioned as preferable compound, is prepared according to the following process:

A Grignard reagent is prepared from an alkylbromobenzene (51) according to a conventional process, followed by reacting an acid chloride derivative (52) with the reagent using iron (III) acetyl acetonate as a catalyst, to prepare a compound (53). This compound (53) is reduced with lithiumaluminum hydride using anhydrous aluminum chloride as catalyst in THF to obtain a compound (54), subjecting it to demethylation with boron tribromide in dichloromethane and then treating with an oxydant such as sodium hypochlorite, to prepare a compound (55). Further, when (55) is hydrogenated in the presence of a Pt group or Rh group catalyst, a compound (56) is prepared. Further, a compound (1-c) is prepared using the compound (55) and the compound (56) as a raw materials, in the same process as that having led the cyclohexanone derivative (45) to the compound (1-b).

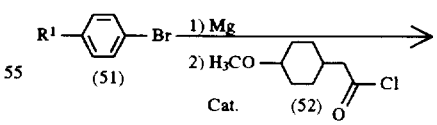

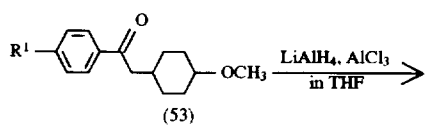

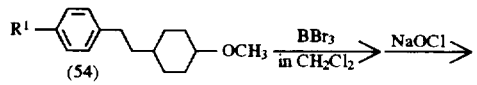

-continued

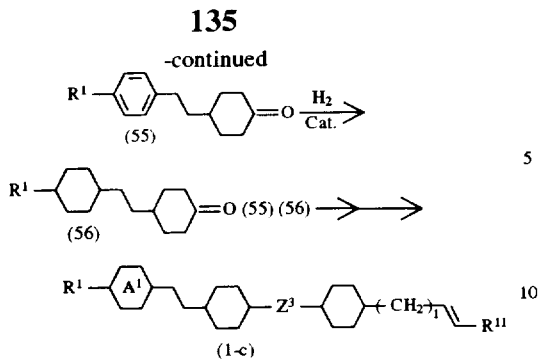

In these formulas, $R^1$, $R^{11}$, ring $A^1$, $Z^3$ and l are as defined above.

Compounds of the formula (1-d) mentioned as preferable compounds can be prepared according to the following process:

A base such as a sodium alkoxide, an alkyllithium, etc. is reacted with a Wittig reagent expressed by the formula (57), to prepare an ylide, followed by reacting an aldehyde derivative (22) with the ylide, to prepare an E,Z-olefin mixture (58). This mixture (58) is isomerized according to a process described in the above Japanese patent publication No. Hei 4-30382 or Japanese patent publication No. Hei 6-62462, extracting only a E-ethenyl derivative, followed by subjecting it to the same process as that having prepared the compound (1-b) from the above cyclohexanone derivative (45), to prepare a compound (1-d).

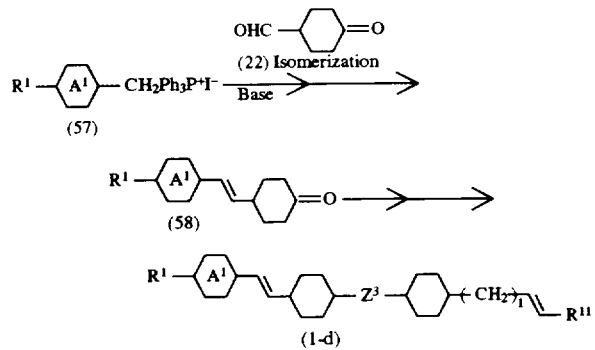

In these equations, $R^1$, $R^{12}$, ring $A^1$, $Z^3$ and l are as defined above.

Compounds of the formula (1-e) shown as preferable compounds can be prepared according to the following process:

Bromomethyltriphenylphosphine bromide and an ylide prepared from a suitable base are reacted with a compound (59) prepared in the same manner as in the case of the above compound (41) according to the process described in Japanese patent publication No. Hei 4-30382, to derive a compound (60), followed by reacting therewith potassium-t-butoxide, to prepare a compound (61). This compound (61) is treated with n-butyllithium, followed by reacting a compound (62) therewith, to obtain a compound (1-e).

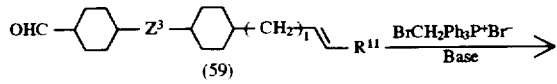

-continued

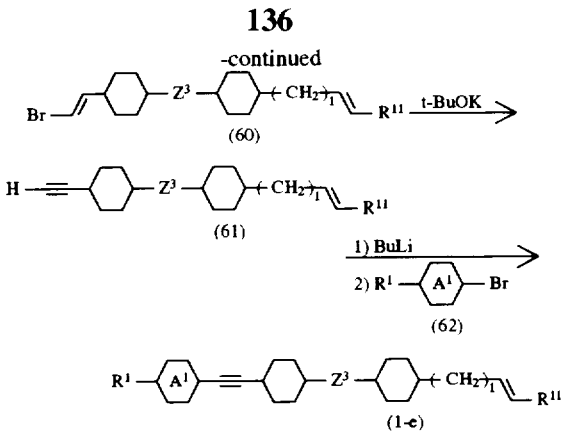

In these formulas, $R^1$, $R^{11}$, ring $A^1$, $Z^3$ and l are defined as above.

Compounds of the formulas (1-f) to (1-n) shown as preferable compounds can be prepared by selecting suitable starting substances and according to the reactions shown in the case of preparations of the compounds of the formulas (1-a) to (1-e) or combinations of known reactions to the above reactions. Further, other compounds not described above, but included in the formula (1) can be alike prepared by selecting suitable starting substances and according to combinations of the above reactions and known reactions.

Effectiveness of the Invention

The compound of the present invention has a very low viscosity and a high elastic constant ratio. Further, the compound has a very good miscibility with many other liquid crystalline compounds, namely with existing liquid crystal compounds such as those of ester group, Schiff's base group, biphenyl group, phenylcyclohexane group, bicyclohexane group, heterocyclic group, fluorine group, etc., and particularly has a superior miscibility therewith at low temperature. Further, when the compound of the present invention is added as a component of liquid crystal compositions, it is possible to suppress lowering of mesomorphic range of nematic liquid crystal phase and at the same time, notably lower only the viscosity.

EXAMPLE

The process for producing the compound of the present invention and examples of its use will be described in more details by way of Examples, but the present invention should not be construed to be limited thereto. In addition, in the respective examples, Cr, N, S and Iso, respectively represent crystal, nematic phase, smectic phase and isotropic liquid. The units of the phase transition temperatures all refer to °C.

EXAMPLE 1

Preparation of 1-ethenyl-4-(4-(trans-4-pentylcyclohexyl) butyl)cyclohexane (Compound No. 5) (in the formula (1), m=n=i=0, $R^1=C_5H_{11}$, $Z^3=-(CH_2)_4-$ and $R^2$=ethenyl group)

In a 1 l three-necked flask equipped with a stirrer, a thermometer and a nitrogen gas-introducing tube, methoxymethyltriphenylphosphonium chloride (29.1 g, 84.8 mmol) was dissolved in THF (200 ml) in a nitrogen gas atmosphere, followed by cooling the resulting solution down to −30° C. or lower with an acetone-dry ice refrigerant carrier, adding potassium-t-butoxide (9.9 g, 89.0 mmol)

stirring the mixture for 2 hours, while keeping −30° C. or lower, dropwise adding a solution of (4-(trans-4-pentylcyclohexyl)butyl)cyclohexanone (20 g, 65.2 mmol) described in Japanese patent application laid-open No. Hei 5-310605, dissolved in THF (50 ml), for 20 minutes, keeping the same temperature, thereafter raising the temperature up to room temperature over one hour, further agitating the mixture at room temperature for 4 hours, adding water (200 ml) to complete the reaction, twice extracting with toluene (150 ml), three times washing the toluene layer with water (100 ml), drying over anhydrous magnesium sulfate, distilling off the solvent under reduced pressure for concentration, and purifying the concentrated residue according to silica gel chromatography using toluene as a developing solvent, to obtain yellow-brown crystal (19.8 g).

In a 500 ml, eggplant type flask equipped with a cooling tube, the yellow-brown crystals (19.8 g) obtained according to the above process were dissolved in toluene (100 ml), followed by adding 99% formic acid (16.5 g, 355.8 mmol), heating the mixture under reflux for 2 hours, cooling the reaction solution down to room temperature, adding water (100 ml), separating the organic layer, further extracting the aqueous layer with toluene (100 ml), combining the organic layers, washing the organic layers twice with water (100 ml), once with a saturated aqueous solution of sodium hydrogen carbonate (50 ml) and twice with water (100 ml), drying over anhydrous $MgSO_4$, distilling off the solvent under reduced pressure, and concentrating, to obtain yellow-brown crystals (18.1 g). This compound is (4-(trans-4-pentylcyclohexyl)butyl)cyclohexylcarbaldehyde.

The measurement results of $^1$H-NMR intensely supported the structure of this compound.

δppm 2.86 (3H, s, $OCH_3$), 5.73, (1H, bs)

In a 500 ml, three-necked flask equipped with a stirrer, a thermometer and a nitrogen gas-introducing tube, methyltriphenylphosphonium chloride (29.6 g, 73.2 mol) was dissolved in THF (200 ml) in a nitrogen gas atmosphere, followed by cooling the resulting solution down to −30° C. or lower by means of a refrigerant carrier, adding potassium-t-butoxide (8.6 g, 76.9 mmol), stirring the mixture for 2 hours, while keeping −30° C., dropwise adding a solution obtained by dissolving (4-(trans-4-pentylcyclohexyl)butyl) cyclohexylcarbaldehyde (18.1 g, 56.3 mmol) in THF (50 ml), for 20 minutes while keeping the same temperature, elevating the temperature up to room temperature over one hour, further agitating the mixture at room temperature for 4 hours, adding water (200 ml) to the reaction solution to complete the reaction, twice extracting the solution with toluene (150 ml), three times washing the toluene layer with water (100 ml), drying it over anhydrous magnesium sulfate, distilling off the solvent under reduced pressure for concentration, purifying the concentrated residue according to silica gel chromatography using heptane as a developing solvent, to obtain colorless crystals (15.9 g), and recrystallizing the resulting crystals for purification, to obtain 1-ethenyl-4-(4-(trans-4-pentylcyclohexyl)butyl) cyclohexane (7.2 g). -S 53.3-54.1 Iso- The measurement results of $^1$H-NMR and GC-MS intensely the structure of the present compound.

$^1$H-NMR: δppm 4.79–5.05 (2H, m) 5.78 (1H, m)
GC-MS: $M^+$318

Using (4-(trans-4-alkylcyclohexyl)butyl)cyclohexanone having a different alkyl group chain in place of (4-(trans-4-pentylcyclohexyl)butyl)cyclohexanone used in the above preparation process, the following compounds having the respective numbers shown below can be prepared according to the above preparation process:

1-ethenyl-4-(4-trans-4-methylcyclohexyl)butyl)-cyclohexane (No. 1)

1-ethenyl-4-(4-(trans-4-ethylcyclohexyl)butyl)-cyclohexane (No. 2) Cr 34.2–35.0 Iso 1-ethenyl-4-(4-(trans-4-propylcyclohexyl)butyl)-cyclohexane (No. 3) SB 44.5–45.1 Iso 1-ethenyl-4-(4-(trans-4-butylcyclohexyl)butyl)-cyclohexane (No. 4)

1-ethenyl-4-(4-(trans-4-hexylcyclohexyl)butyl)-cyclohexane 1-ethenyl-4-(4-(trans-4-heptylcyclohexyl)butyl)-cyclohexane (No. 6)

1-ethenyl-4-(4-(trans-4-octylcyclohexyl)butyl)-cyclohexane 1-ethenyl-4-(4-(trans-4-nonylcyclohexyl)butyl)-cyclohexane 1-ethenyl-4-(4-(trans-4-decylcyclohexyl)butyl)-cyclohexane Further, the following compounds can be prepared according to the above preparation process:

(E)-1-propenyl-4-(4-(trans-4-ethylcyclohexyl)butyl)-cyclohexane (No. 8)

(E)-1-propenyl-4-(4-(trans-4-propylcyclohexyl)butyl)-cyclohexane (No. 9)

(E)-1-propenyl-4-(4-(trans-4-butylcyclohexyl)butyl)-cyclohexane (E)-1-propenyl-4-(4-(trans-4-pentylcyclohexyl)butyl)-cyclohexane (No. 10)

(E)-1-butenyl-4-(4-(trans-4-ethylcyclohexyl)butyl)-cyclohexane (No. 13)

(E)-1-butenyl-4-(4-(trans-4-propylcyclohexyl)butyl)-cyclohexane (No. 14)

(E)-1-butenyl-4-(4-(trans-4-butylcyclohexyl)butyl)-cyclohexane (E)-1-butenyl-4-(4-(trans-4-pentylcyclohexyl)butyl)-cyclohexane (No. 15)

3-Butenyl-4-(4-(trans-4-ethylcyclohexyl)butyl)-cyclohexane (No. 23)

3-Butenyl-4-(4-(trans-4-propylcyclohexyl)butyl)-cyclohexane (No. 24)

3-Butenyl-4-(4-(trans-4-butylcyclohexyl)butyl)-cyclohexane

3-Butenyl-4-(4-(trans-4-pentylcyclohexyl)butyl)-cyclohexane (No. 25)

(E)-1-pentenyl-4-(4-(trans-4-ethylcyclohexyl)butyl)-cyclohexane (No. 18)

(E)-1-pentenyl-4-(4-(trans-4-propylcyclohexyl)butyl)-cyclohexane (No. 19)

(E)-1-pentenyl-4-(4-(trans-4-butylcyclohexyl)butyl)-cyclohexane (E)-1-pentenyl-4-(4-(trans-4-pentylcyclohexyl)butyl)-cyclohexane (No. 20)

(E)-3-pentenyl-4-(4-(trans-4-ethylcyclohexyl)butyl)-cyclohexane (No. 28)

(E)-3-pentenyl-4-(4-(trans-4-propylcyclohexyl)butyl)-cyclohexane (No. 29)

(E)-3-pentenyl-4-(4-(trans-4-butylcyclohexyl)butyl)-cyclohexane (E)-3-pentenyl-4-(4-(trans-4-pentylcyclohexyl)butyl)-cyclohexane (No. 30)

EXAMPLE 2

Preparation of 1-ethenyl-4-(4-trans-4-((E)-3-pentenyl)-cyclohexyl)butyl)cyclohexane (compound No. 127)

(a compound of the formula (1) wherein m=n=i=0; R¹= (E)-3-pentenyl group; Z³=—(CH₂)₄—; and R²=ether group)

In a 1 l three-necked flask equipped with a stirrer, a thermometer and a nitrogen gas-introducing tube, 1,3-dioxolane-2-yl)ethyltriphenylphosphonium chloride (165.9 g, 0.42 mol) was suspended in THF (500 ml), followed by cooling the suspension down to −30° C. with an acetone-dry ice refrigerant carrier, adding potassium-t-butoxide (48.7 g, 0.43 mol), agitating the mixture for 2 hours, while keeping the temperature at −30° C. or lower, dropwise adding a solution of 1,4-cyclohexanedione monoethylene ketal (50.0 g, 0.32 mol) dissolved in THF (150 ml) over 40 minutes, while keeping it at the same temperature, elevating the temperature up to room temperature, further agitating the mixture at room temperature for 4 hours, adding water (300 ml) to the reaction solution, to complete the reaction, three times extracting the mixture with toluene (300 ml), three times washing the toluene layer with water (300 ml), drying it over anhydrous magnesium sulfate, distilling off the solvent under reduced pressure for concentration, and purifying the concentration residue according to silica gel column chromatography using a mixed solvent of toluene/ethyl acetate =2:1 as a developing solvent, to obtain yellow-brown crystals (71.5 g).

In a 1 l, three-necked flask equipped with a stirrer, the yellow-brown crystals (71.5 g) obtained according to the above process were dissolved in a mixed solvent of toluene/ethanol (250 ml), followed by adding 5%-Pd-C catalyst (5.7 g), carrying out catalytic hydrogenation reduction at room temperature, under a hydrogen pressure of 5 to 10 Kg/cm² for 5 hours, distilling off the solvent from the reaction solution having separated the catalyst, for concentration, dissolving the concentrated residue in toluene (300 ml) in a 500 ml eggplant type flask equipped with a cooling tube, adding 99% formic acid (82.8 g, 1.78 mol), heating the mixture under reflux for 2 hours, cooling the reaction solution down to room temperature, adding water (300 ml), separating the organic layer, further extracting the aqueous layer with toluene (300 ml), combining the extract with the organic layer, washing the organic layer successively twice with water (300 ml), once with a saturated aqueous solution of sodium bicarbonate (100 ml) and twice with water (300 ml), drying over anhydrous magnesium sulfate, distilling off the solvent under reduced pressure, for concentration, to obtain yellow-brown crystals (41.2 g). The crystals refer to 4-(2-formylethane-1-yl)cyclohexanone.

In a 1 l, three-necked flask equipped with a stirrer, a thermometer and a nitrogen gas-introducing tube, (4-methoxycyclohexyl)methyltriphenylphosphine iodide (175.6 g, 0.34 mol) was suspended in THF (500 ml) in a nitrogen gas atmosphere, followed by cooling the suspension down to −30° C. or lower by means of acetone-dry ice refrigerant carrier, adding potassium-t-butoxide (40.1 g, 0.36 mol), and agitating the mixture for 2 hours, while keeping the temperature at −30° C. or lower. A solution of 4-(2-formylethane-1-yl)cyclohexanone (41.2 g, 0.27 mol) obtained according to the above process, dissolved in THF (150 ml), was dropwise added over 40 minutes, while keeping the same temperature, followed by elevating the temperature up to room temperature over one hour, further agitating the mixture at room temperature for 4 hours, adding water (300 ml) to the reaction solution to complete the reaction, three times extracting with toluene (300 ml), three times washing the toluene layer with water (300 ml), drying the layer over anhydrous magnesium sulfate, distilling off the solvent under reduced pressure, for concentration, and purifying the concentrated residue according to silica gel chromatography using a mixed solvent of toluene/ethyl acetate (2:1) as a developing solvent, to obtain yellow-brown crystals (65.0 g). The crystals refer to (4-(trans-4-methoxycyclohexyl)-(E,Z)-3-butenyl)cyclohexanone.

In a 1 l, three-necked flask equipped with a stirrer, (4-(trans-4-methoxycyclohexyl)-(E,Z)-3-butenyl)cyclohexanone (65.0 g) obtained according to the above process was dissolved in a mixed solvent of toluene/ethanol (1:1) (250 ml), followed by adding 5%-Pd-C catalyst (5.4 g), carrying out catalytic hydrogen-reduction under a hydrogen pressure of 5 to 10 Kg/cm² at room temperature for 4 hours, filtering off the catalyst, distilling off the solvent from the resulting reaction solution under reducing pressure, for concentration, purifying the concentrated residue according to silica gel chromatography using a mixed solvent of toluene-ethyl acetate (4:1) as a developing solvent, and further recrystallizing the resulting substance with heptane, to obtain colorless crystals (55.5 g). The crystals refer to (4-(trans-4-methoxycyclohexyl)-butyl)cyclohexanone.

In a 1 l, three-necked flask equipped with a stirrer, a thermometer and a nitrogen gas-introducing tube, |1,3-dioxolan-2-yl)ethyl|triphenylphosphonium chloride (117.7 g, 0.30 mol) was suspended in THF (500 ml) in nitrogen gas atmosphere, followed by cooling the resulting suspension down to −30° C. or lower with an acetone-dry ice cooling solvent, adding potassium-t-butoxide (40.1 g, 0.36 mol), agitating the mixture for 2 hours, while keeping the temperature at −30° C. or lower, dropwise adding a solution of (4-(trans-4-methoxycyclohexyl)butyl)cyclohexanone (55.5 g, 0.21 mol) obtained according to the above process, dissolved in THF (150 ml), over 40 minutes, while keeping the temperature at the same temperature, elevating the temperature up to room temperature over one hour, further agitating the mixture at room temperature for 4 hours, adding water (300 ml) to the reaction solution, to complete the reaction, three times extracting the solution with toluene (300 ml), three times washing the toluene layer with water (300 ml), drying over anhydrous magnesium sulfate, and distilling off the solvent under reduced pressure, for concentration. In a 1 l, three-necked flask equipped with a stirrer, the concentrated residue was dissolved in a mixed solvent of toluene/ethanol (1/1) (250 ml), followed by adding 5%-Pd-C catalyst (4.5 g), carrying out catalytic hydrogen-reduction at room temperature under a hydrogen pressure of 5 to 10 Kg/cm² for 5 hours, filtering off the catalyst, and distilling off the solvent from the reaction solution under reduced pressure, for concentration. In a 500 ml, eggplant type flask equipped with a cooling tube, the concentrated residue (66.9 g) was dissolved in toluene (300 ml), followed by adding 99% formic acid (53.0 g, 1.14 mol), heating the mixture under reflux for 2 hours, cooling the reaction solution down to room temperature, adding water (300 ml), to separate the organic layer, further extracting the aqueous layer with toluene (300 ml), combining the extract with the organic layer, washing the organic layer successively twice with water (300 ml), once with an aqueous solution of sodium bicarbonate (100 ml) and twice with water (300 ml), drying the layer over anhydrous magnesium sulfate, and distilling off the solvent under reduced pressure, for concentration, to obtain yellow-brown crystals (55.1 g). The crystals refer to (4-(trans-4-methoxycyclohexyl)butyl) cyclohexylpropylaldehyde.

In a 500 ml, three-necked flask equipped with a stirrer, a thermometer and a nitrogen gas-introducing tube, ethyltriphenylphosphine bromide (86.4 g, 0.23 mol) was dissolved in THF (400 ml) in a nitrogen gas atmosphere, followed by cooling the solution down to −30°C. or lower with an acetone-dry ice refrigerant carrier, adding potassium-t-butoxide (27.5 g. 0.25 mol), agitating the mixture for 2 hours, while keeping the temperature at −30° C. or lower, dropwise adding a solution of (4-(trans-4-methoxycyclohexyl)butyl)cyclohexylpropylaldehyde dissolved in THF (200 ml) over 30 minutes, while keeping the temperature at the same temperature, elevating the temperature up to room temperature over one hour, further agitating the mixture at room temperature for 4 hours, adding water (200 ml) to the reaction solution, to complete the reaction, twice extracting the solution with toluene (200 ml), three times washing the toluene layer with water (200 ml), drying it over anhydrous magnesium sulfate, distilling off the solvent under reduced pressure, for concentration, and purifying the concentrated residue according to silica gel chromatography using toluene as a developing solvent, to obtain yellow-brown crystals (48.7 g). The crystals refer to trans-(E.Z)-3-pentenyl)-4-(4-(trans-4-methoxycyclohexyl)-butyl) cyclohexane.

This compound was subjected to the following isomerization process. In a 1 l. eggplant type flask, equipped with a cooling tube, trans-((E.Z)-3-pentenyl)-4-(4-(trans-4-methoxycyclohexyl)butyl)cyclohexane (48.7 g. 0.15 mol) was dissolved in a mixed solvent of toluene/ ethanol (1:1) (200 ml), followed by adding sodium benzenesulfinate (37.4 g. 0.23 mol) and 6N-hydrochloric acid (33 ml), heating the mixture under reflux for 10 hours, cooling the mixture down to room temperature, adding water (200 ml), to complete the reaction, twice extracting the reaction solution with toluene (200 ml), washing the toluene layer successively twice with water (200 ml), once with an aqueous solution of sodium bicarbonate (150 ml) and twice with water (200 ml), drying the layer over anhydrous magnesium sulfate, distilling off the solvent under reduced pressure, for concentration, purifying the concentrated residue according to silica gel chromatography using toluene as a developing solvent, and recrystallizing with heptane to obtain colorless crystals (34.0 g). The crystals refer to trans-((E)-3-pentenyl)-4-(4-(trans-4-methoxycyclohexyl)butyl)cyclo hexane.

In a 500 ml, three-necked flask equipped with a stirrer, a thermometer and a nitrogen gas-introducing tube, dichloromethane was cooled down −50° C. or lower, with an acetone-dry ice refrigerant carrier, in nitrogen gas atmosphere, followed by adding boron trifluoride (45.2 g. 0.18 mol), dropwise adding a solution of trans-((E)-3-pentenyl)-4-(4-(trans-4-methoxycyclohexyl)-butyl) cyclohexane (34.0 g. 0.11 mol), dissolved in dichloromethane (100 ml), over one hour, while keeping it at −50° C. or lower, gradually elevating the temperature up to room temperature over 2 hours, agitating the solution for 8 hours at room temperature, pouring the reaction solution into an ice water (500 ml), twice extracting the solution with diethyl ether (300 ml), four times washing the extracted layer with water (250 ml), drying it over anhydrous magnesium sulfate, distilling off the solvent, for concentration.

In a 500 ml. three-necked flask equipped with a stirrer, a thermometer and a nitrogen gas-introducing tube, the resulting concentrated residue (26.3 g) was dissolved in dichloromethane (200 ml) in a nitrogen gas atmosphere, followed by adding glacial acetic acid (12.4 g. 0.21 mol), keeping the inside temperature at 10° to 15° C., while cooling in a water bath, dropwise adding 12% aqueous solution of hypochlorous acid (69.3 g) over 50 minutes, further agitating the mixture at room temperature for 3 hours, adding water(150 ml)to the reaction solution, to complete the reaction, separating dichloromethane layer from the reaction solution, washing it successively twice with water (200 ml), once with a saturated aqueous solution of sodium bicaronate (150 ml) and twice with water (200 ml), drying over anhydrous magnesium sulfate, distilling off the solvent under reduced pressure, for concentration, purifying the concentrated residue according to silica gel chromatography using toluene as a developing solvent, and recrystallizing from heptane, to obtain colorless crystals (23.5 g).

The crystals refer to 4-(4-(trans-4-((E)-3-pentenyl)-cyclohexyl)butyl)cyclohexanone.

In a 1 l. three-necked flask equipped with a stirrer, a thermometer and a nitrogen gas-introducing tube, methoxymethyltriphenylphosphonium chloride (34.4 g. 100.5 mmol) was dissolved in THF (200 ml) in a nitrogen gas atmosphere, followed by cooling the solution down to −30° C. or lower with an aceton-dry ice refrigerant carrier, adding potassium-t-butoxide (11.8 g. 105.5 mmol), agitating the mixture for 2 hours, while keeping the temperature at −30° C. or lower, dropwise adding a solution of 4-(4-(trans-4-((E)-3-pentenyl)cyclohexyl)butyl)cyclohexanone (23.5 g. 77.3 mmol) dissolved in THF (70 ml) over 20 minutes, while keeping the temperature at the same temperature, elevating the temperature up to room temperature over one hour, further agitating the mixture at room temperature for 4 hours, adding water (200 ml) to the reaction solution, to complete the reaction, twice extracting the reaction solution with toluene (150 ml), three times washing the toluene layer with water (100 ml), further drying it over anhydrous magnesium sulfate, distilling off the solvent under reduced pressure, for concentration, and purifying the concentrated residue according to silica gel chromatography using toluene as a developing solvent, to obtain yellow-brown crystals (23.0 g).

In a 500 ml. eggplant type flask equipped with a cooling tube, the yellow-brown crystals (23.0 g) obtained according to the above process, were dissolved in toluene (100 ml), followed by adding 99% formic acid (19.8 g. 43.0 mmol), heating the mixture under reflux for 2 hours, cooling the reaction solution down to room temperature, adding water (100 ml), separating the organic layer, further extracting the aqueous layer with toluene (100 ml), combining the extract with the above organic layer, washing the organic layer successively twice with water (100 ml), once with a saturated aqueous solution of sodium bicarbonate (50 ml) and twice with water (100 ml), drying the layer over anhydrous magnesium sulfate, distilling off the solvent under reduced pressure and concentrating, to obtain yellow-brown crystals (22.1 g). The crystals refer to 4-(4-(trans-4-((E)-3-pentenyl) cyclohexyl)butyl)-cyclohexanecarbaldehyde.

In a 500 ml. three-necked flask equipped with a stirrer, a thermometer and a nitrogen gas-introducing tube, methyltriphenylphosphonium iodide (36.6 g. 90.44 mmol) was dissolved in THF (200 ml) in a nitrogen gas atmosphere, followed by cooling the solution down to −30° C. or lower by means of an acetone-dry ice refrigerant carrier, adding potassium-t-butoxide (10.7 g. 94.9 mmol), agitating the mixture for 2 hours, while keeping the temperature of −30° C. or lower, dropwise adding a solution of 4-(4-(trans-4-((E)-3-pentenyl)cyclohexyl)butyl)cyclohexane-carbaldehyde (22.1 g. 69.6 mmol) dissolved in THF (70 ml) over 20 minutes, while keeping the same temperature, elevating the temperature up to room temperature over one hour, agitating the mixture at room temperature for 4 hours, adding water (200 ml) to the reaction solution, to complete the reaction, twice extracting the solution with toluene (150 ml), washing the toluene layer three times with water (100 ml), drying the layer over anhydrous magnesium sulfate, distilling off the solvent under reduced pressure, and purifying the concentrated residue according to silica gel chromatography using heptane as a developing solvent, to obtain colorless crystals (18.7 g). The crystals were recrystallized from heptane, for purification, to obtain the captioned compound, 1-ethenyl-4-(4-(trans-4-((E)-3-pentenyl)cyclohexyl)butyl) cyclohexane (6.5 g).

The measurement results of $^1$H-NMR and GC-MS intensely supported the structure of this compound.

GC-MS: M$^+$316

By variously selecting the starting substance or the reaction reagent, the following compounds can be prepared according to the above preparation process:

(E)-1-propenyl-4-(4-trans-4-((E)-3-pentenyl)cyclohexyl) butyl)cyclohexane (No. 132)

2-propenyl-4-(4-(trans-4-((E)-3-pentenyl)chclohexyl)-butyl)cyclohexane (E)-1-butenyl-4-(4-(trans-4-((E)-3-pentenyl)cyclohexyl) butyl)cyclohexane (No. 136)

(Z)-2-butenyl-4-(4-(trans-4-((E)-3-pentenyl)cyclohexyl) butyl)cyclohexane 3-butenyl-4-(4-(trans-4-((E)-3-pentenyl)cyclohexyl)-butyl)cyclohexane (No. 141)

(E)-1-pentenyl-4-(4-(trans-4-((E)-3-pentenyl)cyclohexyl) butyl)cyclohexane (No. 139)

(Z)-2-pentenyl-4-(4-(trans-4-((E)-3-pentenyl)cyclohexyl) butyl)cyclohexane (E)-3-pentenyl-4-(4-(trans-4-((E)-3-pentenyl)cyclohexyl) butyl)cyclohexane (No. 142)

1-ethenyl-4-(4-(trans-4-(1-ethenyl)cyclohexyl)-butylcyclohexane (No. 122)

(E)-1-propenyl-4-(4-(trans-4-((E)-1-propenyl) cyclohexyl)butyl)cyclohexane (No. 128)

2-propenyl-4-(4-(trans-4-(2-propenyl)cyclohexyl)-butyl) cyclohexane (E)-1-butenyl-4-(4-(trans-4-((E)-1-butenyl)cyclohexyl) butyl)cyclohexane (No. 133)

(Z)-2-butenyl-4-(4-(trans-4-((Z)-2-butenyl)cyclohexyl) butyl)cyclohexane (E)-2-butenyl-4-(4-(trans-4-((Z)-2-butenyl)cyclohexyl) butyl)cyclohexane (E)-2-butenyl-4-(4-(trans-4-((E)-2-butenyl)cyclohexyl) butyl)cyclohexane 3-butenyl-4-(4-(trans-4-(3-butenyl)cyclohexyl)butyl)-cyclohexane (No. 140)

(E)-1-pentenyl-4-(4-(trans-4-((E)-1-pentenyl)cyclohexyl) butyl)cyclohexane (No. 137)

(Z)-2-pentenyl-4-(4-(trans-4-((Z)-2-pentenyl)cyclohexyl) butyl)cyclohexane (E)-2-pentenyl-4-(4-(trans-4-((Z)-2-pentenyl)cyclohexyl) butyl)cyclohexane (E)-2-pentenyl-4-(4-(trans-4-((E)-2-pentenyl)cyclohexyl) butyl)cyclohexane

EXAMPLE 3

Preparation of trans-(1-ethenyl)-4-((E)-4-(trans-4-propylcyclohexyl)-1-butenyl)cyclohexane (Compound No.94)

wherein, in the formula (1), m=n=i=0; R$^1$=n-propyl group; Z$^3$=—(CH$_2$)$_2$—CH═CH—; and R$^2$=ethenyl group.

In a 1 l. three-necked flask equipped with a stirrer, a thermometer and a nitrogen gas-introducing tube, a mixture of (trans-4-propylcyclohexyl)-3-bromopropane (50 g, 0.20 mol), triphenylphosphine (69.1 g, 0.26 mol) and xylene (30 ml) was heated with stirring for 60 hours, while keeping the inside temperature at 130° C., followed by suspending the reaction mixture in THF (300 ml), cooling the suspension down to −30° C. or lower, with an acetone-dry ice refrigerant carrier, adding potassium-t-butoxide (23.8 g, 0.21 mol), agitating the mixture for 2 hours, while keeping the temperature at −30° C. or lower, dropwise adding a solution of 4-formylcyclohexanone (33.1 g, 0.26 mol) dissolved in THF (150 ml), over 40 minutes, while keeping the same temperature, elevating the temperature up to room temperature over one hour, further agitating the mixture at room temperature for 4 hours, adding water (300 ml) to the reaction solution, to complete the reaction, three times extracting the solution with toluene (300 ml), three times washing the toluene layer with water (300 ml), drying over anhydrous magnesium sulfate, distilling off the solvent under reduced pressure, for concentration, and purifying the concentrated residue according to silica gel chromatography using toluene as a developing solvent, to obtain yellow-brown crystals (36.2 g).

In a 1 l. eggplant type flask equipped with a cooling tube, the reaction mixture (36.2 g) obtained according to the above process was dissolved in a mixed solvent of toluene/ethanol (1:1) (200 ml), followed by adding sodium benzenesulfinate (32.3 g) and 6N-hydrochloric acid (32.8 ml), heating the mixture under reflux for 10 hours, cooling it down to room temperature, adding water (200 ml), to complete the reaction, extracting the reaction solution twice with toluene (250 ml), washing the toluene layer successively twice with water (200 ml), once with a saturated aqueous solution of sodium bicarbonate (150 ml) and further, twice with water (200 ml), drying over anhydrous magnesium sulfate, distilling off the solvent under reduced pressure, for concentration, purifying the concentrated residue according to silica gel chromatography using toluene as a developing solvent, and recrystallizing it from heptane, to obtain colorless crystals (16.3 g). The crystals refer to 4-((E)-4-(trans-4-propylcyclohexyl)-1-butenyl) cyclohexanone.

In a 1 l. three-necked flask equipped with a stirrer, a thermometer and a nitrogen gas-introducing tube, methoxymethyltriphenylphosphonium chloride (26.3 g, 76.7 mmol) was dissolved in THF (150 ml), followed by cooling the solution down to −30° C. or lower, with an acetone-dry ice refrigerant carrier, adding potassium-t-butoxide (9.0 g, 80.5 mmol), agitating the mixture for 2 hours, while keeping the temperature at −30° C. or lower, dropwise adding a solution of 4-((E)-4-(trans-4-propyl-cyclohexyl)-1-butenyl cyclohexanone (16.3 g, 59.0 mmol) dissolved in THF (70 ml) over 20 minutes, while keeping the same temperature elevating the temperature up to room temperature over one hour, further agitating the solution at room temperature for 4 hours, adding water (200 ml) to the reaction solution, to complete the reaction, extracting it twice with toluene (150 ml), washing the toluene layer three times with water (100 ml), drying it over anhydrous magnesium sulfate, distilling off the solvent under reduced pressure, for concentration and purifying the concentrated residue according to silica gel chromatography using toluene as a developing solvent to obtain yellow-brown crystals (15.3 g).

In a 500 ml. eggplant type flask equipped with a cooling tube, the yellow-brown crystals (15.3 g) obtained according to the above process were dissolved in toluene (100 ml) followed by adding 99% formic acid (12.2 g, 263.0 mmol) heating the mixture under reflux for 2 hours, cooling th reaction solution down to room temperature, adding water (100 ml), separating an organic layer, further extracting the aqueous solution with toluene (100 ml), combining the extract with the organic layer, washing the resulting organic layer successively twice with water (100 ml), once with a saturated aqueous solution of sodium bicarbonate (50 ml) and twice with water (100 ml), drying the organic layer over anhydrous magnesium sulfate, distilling off the solvent under reduced pressure, for concentration, to obtain yellow-brown crystals (13.9 g). The crystals refer to 4-((E)-4-(trans-4-propylcyclohexyl)-1-butenyl)cyclohexanecarbaldehyde.

In a 500 ml, three-necked flask equipped with a stirrer, a thermometer and a nitrogen gas-introducing tube, methyltriphenylphosphonium iodide (25.1 g, 62.1 mmol) was dissolved in THF (150 ml), followed by cooling the solution down to −30° C. or lower, with an acetone-dry ice refrigerant carrier, adding potassium-butoxide (7.3 g, 65.2 mmol), agitating the mixture for 2 hours, while keeping the temperature at −30° C. or lower, dropwise adding a solution of 4-((E)-4-(trans-4-propylcyclohexyl)-1-butenyl)-cyclohexanecarbaldehyde (13.9 g, 47.8 mmol) dissolved in THF (50 ml), over 20 minutes, keeping the same temperature, elevating the temperature up to room temperature over one hour, further agitating the mixture at room temperature for 4 hours, adding water (200 ml) to the reaction solution, to complete the reaction, extracting the solution twice with toluene (150 ml), washing the toluene layer three times with water (100 ml), drying over anhydrous magnesium sulfate, distilling off the solvent under reduced pressure, for concentration, purifying the concentrated residue according to silica gel chromatography using heptane as a developing solvent to obtain colorless crystals (12.3 g), and recrystallizing the crystals from heptane, for purification, to obtain the captioned compound, trans-(1-ethenyl)-4-((E)-4-(trans-4-propylcyclohexyl)-1-butenyl) cyclohexane (3.7 g).

The measurement results of $^1$H-NMR and GC-MS intensely supported the structure of the present compound.
GC-MS: M$^+$288

When (trans-4-propylcyclohexyl)-3-bromopropane used in the above preparation process is replaced by (trans-4-alkylcyclohexyl)-3-bromopropane having a different chain length of alkyl group and the latter is processed according to the above preparation process, the following compounds can be prepared:

trans-(1-ethenyl)-4-((E)-4-(trans-4-methylcyclohexyl)-1-butenyl)cyclohexane (No. 92)

trans-(1-ethenyl)-4-((E)-4-(trans-4-ethylcyclohexyl)-1-butenyl)cyclohexane trans-(1-ethenyl)-4-((E)-4-(trans-4-butylcyclohexyl)-1-butenyl)cyclohexane trans-(1-ethenyl)-4-((E)-4-(trans-4-pentylcyclohexyl)-1-butenyl)cyclohexane (No. 95)

trans-(1-ethenyl)-4-((E)-4-(trans-4-hexylcyclohexyl)-1-butenyl)cyclohexane trans-(1-ethenyl)-4-((E)-4-(trans-4-heptylcyclohexyl)-1-butenyl)cyclohexane (No. 96)

trans-(1-ethenyl)-4-((E)-4-(trans-4-octylcyclohexyl)-1-butenyl)cyclohexane trans-(1-ethenyl)-4-((E)-4-(trans-4-nonylcyclohexyl)-1-butenyl)cyclohexane trans-(1-ethenyl)-4-((E)-4-(trans-4-decylcyclohexyl)-1-butenyl)cyclohexane When the starting substance or the reaction reagent are variously selected, the following compounds can be prepared according to the above preparation process:

trans-((E)-1-propenyl)-4-((E)-4-(trans-4-ethylcyclohexyl)-1-butenyl)cyclohexane (No. 98)

trans-((E)-1-butenyl)-4-((E)-4-(trans-4-ethylcyclohexyl)-1-butenyl)cyclohexane (No. 103)

trans-((E)-1-pentenyl)-4-((E)-4-trans-4-ethylcyclohexyl)-1-butenyl)cyclohexane (No. 108)

trans-(3-butenyl)-4-((E)-4-trans-4-ethylcyclohexyl)-1-butenyl)cyclohexane (No. 113)

trans-((E)-3-pentenyl)-4-((E)-4-(trans-4-ethylcyclohexyl)-1-butenyl)cyclohexane (No. 118)

trans-((E)-1-propenyl)-4-((E)-4-(trans-4-propylcyclohexyl)-1-butenyl)cyclohexane (No. 99)

trans-((E)-1-butenyl)-4-((E)-4-(trans-4-propylcyclohexyl)-1-butenyl)cyclohexane (No. 104)

trans-((E)-1-pentenyl)-4-((E)-4-(trans-4-propylcyclohexyl)-1-butenyl)cyclohexane (No. 109)

trans-(3-butenyl)-4-((E)-4-(trans-4-propylcyclohexyl)-1-butenyl)cyclohexane (No. 114)

trans-((E)-3-pentenyl)-4-((E)-4-(trans-4-propylcyclohexyl)-1-butenyl)cyclohexane (No. 119)

trans-((E)-1-propenyl)-4-((E)-4-(trans-4-pentylcyclohexyl)-1-butenyl)cyclohexane (No. 100)

trans-((E)-1-butenyl)-4-((E)-4-(trans-4-pentylcyclohexyl)-1-butenyl)cyclohexane (No. 105)

trans-((E)-1-pentenyl)-4-((E)-4-(trans-4-pentylcyclohexyl)-1-butenyl)cuclohexane (No. 110)

trans-(3-butenyl)-4-((E)-4-(trans-4-pentylcyclohexyl)-1-butenyl)cyclohexane (No. 115)

trans-((E)-3-pentenyl)-4-((E)-4-(trans-4-pentylcyclohexyl)-1-butenyl)cyclohexane (No. 120)

trans-((E)-1-propenyl)-4-((E)-4-(trans-4-ethylcyclohexyl)-3-butenyl)cyclohexane (No. 38)

trans-((E)-1-butenyl)-4-((E)-4-(trans-4-ethylcyclohexyl)-3-butenyl)cyclohexane (No. 43)

trans-((E)-1-pentenyl)-4-((E)-4-trans-4-ethylcyclohexyl)-3-butenyl)cyclohexane (No. 48)

trans-(3-butenyl)-4-((E)-4-(trans-4-ethylcyclohexyl)-3-butenyl)cyclohexane (No. 53)

trans-((E)-3-pentenyl)-4-((E)-4-(trans-4-ethylcyclohexyl)-3-butenyl)cyclohexane (No. 58)

trans-((E)-1-propenyl)-4-((E)-4-(trans-4-propylcyclohexyl)-3-butenyl)cyclohexane (No. 39)

trans-((E)-1-butenyl)-4-((E)-4-(trans-4-propylcyclohexyl)-3-butenyl)cyclohexane (No. 44)

trans-((E)-1-pentenyl)-4-((E)-4-(trans-4-propylcyclohexyl)-3-butenyl)cyclohexane (No. 49)

trans-(3-butenyl)-4-((E)-4-(trans-4-propylcyclohexyl)-3-butenyl)cyclohexane (No. 54)

trans-((E)-3-pentenyl)-4-((E)-4-(trans-4-propylcyclohexyl)-3-butenyl)cyclohexane (No. 59)

trans-((E)-1-propenyl)-4-((E)-4-(trans-4-pentylcyclohexyl)-3-butenyl)cyclohexane (No. 40)

trans-((E)-1-butenyl)-4-((E)-4-(trans-4-pentylcyclohexyl)-3-butenyl)cyclohexane (No. 45)

trans-((E)-1-pentenyl)-4-((E)-4-(trans-4-pentylcyclohexyl)-3-butenyl)cyclohexane (No. 50)

trans-(3-butenyl)-4-((E)-4-(trans-4-pentylcyclohexyl)-3-butenyl)cyclohexane (No. 55)

trans-((E)-3-pentenyl)-4-((E)-4-trans-4-pentylcyclohexyl)-3-butenyl)cyclohexane (No. 60)

trans-((E)-1-propenyl)-4-((Z)-4-(trans-4-ethylcyclohexyl)-2-butenyl)cyclohexane (No. 68)

trans-((E)-1-butenyl)-4-((Z)-4-(trans-4-ethylcyclohexyl)-2-butenyl)cyclohexane (No. 73)

trans-((E)-1-pentenyl)-4-((Z)-4-(trans-4-ethylcyclohexyl)-2-butenyl)cyclohexane (No. 78)

trans-(3-butenyl)-4-((Z)-4-(trans-4-ethylcyclohexyl)-2-butenyl)cyclohexane (No. 83)

trans-((E)-3-pentenyl)-4-((Z)-4-(trans-4-ethylcyclohexyl)-2-butenyl)cyclohexane (No. 88)

trans-((E)-1-propenyl)-4-((Z)-4-(trans-4-propylcyclohexyl)-2-butenyl)cyclohexane (No. 69)

trans-((E)-1-butenyl)-4-((Z)-4-(trans-4-propylcyclohexyl)-2-butenyl)cyclohexane (No. 74)

trans-((E)-1-pentenyl)-4-((Z)-4-(trans-4-propylcyclohexyl)-2-butenyl)cyclohexane (No. 79)

trans-(3-butenyl)-4-((Z)-4-(trans-4-propylcyclohexyl)-2-butenyl)cyclohexane (No. 84)

trans-((E)-3-pentenyl)-4-((Z)-4-(trans-4-propylcyclohexyl)-2-butenyl)cyclohexane (No. 89)

trans-((E)-1-propenyl)-4-((Z)-4-(trans-4-pentylcyclohexyl)-2-butenyl)cyclohexane (No. 70)

trans-((E)-1-butenyl)-4-((Z)-4-(trans-4-pentylcyclohexyl)-2-butenyl)cyclohexane (No. 75)

trans-((E)-1-pentenyl)-4-((Z)-4-trans-4-pentylcyclohexyl)-2-butenyl)cyclohexane (No. 80)

trans-(3-butenyl)-4-((Z)-4-(trans-4-pentylcyclohexyl)-2-butenyl)cyclohexane (No. 85)

trans-((E)-3-pentenyl)-4-((Z)-4-(trans-4-pentylcyclohexyl)-2-butenyl)cyclohexane (No. 90)

EXAMPLE 4

Preparation of trans-1-ethenyl-4-((E)-4-(trans-4-ethenylcyclohexyl)-1-butenyl)cyclohexane (compound No. 143)

(wherein, in the formula (1), m=n=i=0; $R^1$=ethenyl group; $Z^3$=—CH=CH—$(CH_2)_2$— and $R^2$=ethenyl group)

In a 1 l. three-necked flask equipped with a stirrer, a thermometer and a nitrogen gas-introducing tube, methoxymethyltriphenylphosphonium chloride (59.1 g, 172.0 mmol) was dissolved in THF (200 ml), followed by cooling the solution down to −30° C. or lower with an acetone-dry ice refrigerant carrier, adding potassium-t-butoxide (20.3 g, 181.0 mmol), agitating the mixture for 2 hours, while keeping the temperature at −30° C. or lower, dropwise adding a solution of methoxymethyltriphenylphosphonium chloride (59.1 g, 172.0 mmol) dissolved in THF (200 ml) in a nitrogen gas atmosphere, cooling the solution down to −30° C. or lower, with an acetone dry ice refrigerant carrier, adding potassium-t-butoxide (20.3 g, 181.0 mmol), agitating the mixture for 2 hours, while keeping the temperature at −30° C. or lower, dropwise adding a solution of 4-((E)-4-(trans-4-methoxycyclohexyl)-3-butenyl)cyclohexanone (35.0 g, 133.0 mol) prepared according to the process described in Example 2, dissolved in THF (100 ml), over 40 minutes, while keeping the temperature at the same temperature, elevating the temperature up to room temperature over one hour, agitating the mixture at room temperature for 4 hours, adding water (200 ml) to the reaction solution, to complete the reaction, extracting the reaction solution twice with toluene (200 ml), washing the toluene layer twice with water, drying over anhydrous magnesium sulfate, distilling off the solvent under reduced pressure, for concentration, and purifying the concentrated residue according to silica gel chromatography using toluene as a developing solvent, to obtain yellow-brown crystals (33.1 g).

In a 500 ml eggplant type flask equipped with a cooling tube, the yellow-brown crystals (33.1 g) obtained according to the above process, were dissolved in toluene (100 ml), followed by adding 99% formic acid (27.2 g, 590.0 mmol), heating the mixture under reflux for 2 hours, cooling the reaction solution down to room temperature, adding water (100 ml), separating the resulting organic layer, extracting the aqueous layer with toluene (200 ml), combining the organic layers, washing the organic layer twice with water (150 ml), once with a saturated aqueous solution of sodium bicarbonate (100 ml), further twice with water (150 ml), drying over anhydrous magnesium sulfate, and distilling off the solvent under reduced pressure, for concentration, to obtain yellow-brown crystals (29.5 g). The crystals refer to 4-((E)-4-(trans-4-methoxycyclohexyl)-3-butenyl) cyclohexanecarbaldehyde.

In a 500 ml, three-necked flask equipped with a stirrer, a thermometer and a nitrogen gas introducing tube, methyltriphenylphosphonium iodide (53.7 g, 138.0 mmol) was dissolved in THF (250 ml), followed by cooling the solution down to −30° C. or lower by means of an acetone-dry ice refrigerant carrier, adding potassium-t-butoxide (16.3 g, 145.0 mmol), agitating the mixture for 2 hours, while keeping the temperature at −30° C. or lower, dropwise adding a solution of 4-((E)-4-(trans-4-methoxycyclohexyl)-3-butenyl)cyclohexanecarbaldehyde (29.5 g, 106.9 mmol) dissolved in THF (90 ml) over 30 minutes, while keeping the solution at the same temperature, elevating the temperature to room temperature over 1 hour, further agitating the solution at room temperature for 4 hours, adding water (200 ml) to the reaction solution, to complete the reaction, twice extracting the solution with toluene (150 ml), three times washing the toluene layer with water (100 ml), drying over anhydrous magnesium sulfate, distilling off the solvent under reduced pressure, for concentration, purifying the concentrated residue according to silica gel chromatography using heptane as a developing solvent, to obtain colorless crystals (24.9 g), and recrystallizing the crystals from heptane, to obtain colorless crystals (15.4 g). The crystals refer to 1-ethenyl-4-((E)-4-(trans-4-methoxycyclohexyl)-3-butenyl)cyclohexane.

In a 500 ml, three-necked flask equipped with a stirrer, a thermometer and a nitrogen gas-introducing tube, dichloromethane (250 ml) was cooled down to −50° C. or lower with an acetone-dry ice refrigerant carrier in a nitrogen gas atmosphere, followed by adding boron trifluoride (20.9 g, 83.9 mmol), further dropwise adding a solution of 1-ethenyl-4-((E)-(trans-4-methoxycyclohexyl)-3-butenyl)cyclohexane (15.4 g, 55.9 mmol) dissolved in dichloromethane (100 ml) over one hour, while keeping the temperature at −50° C. or lower, gradually elevating the temperature up to room temperature over 2 hours, further agitating the mixture at room temperature for 8 hours, pouring the reaction solution into ice water (500 ml), twice extracting it with diethyl ether (300 ml), four times washing the extracted layer with water (250 ml), drying it over anhydrous magnesium sulfate, and distilling off the solvent, for concentration.

In a 500 ml, three-necked flask equipped with a stirrer, a thermometer and a nitrogen gas-introducing tube, the extracted residue (11.1 g) was dissolved in dichloromethane (200 ml) in a nitrogen gas atmosphere, followed by adding glacial acetic acid (6.1 g, 101.9 mmol), cooling the mixture in a water bath, dropwise adding a 12% aqueous solution of hypochlorous acid (34.3 g, 55.2 mmol) ovhr 30 minutes, while keeping the inside temperature at 10° to 15° C., further agitating the mixture at room temperature for 3 hours, adding water (150 ml) to the reaction solution, to complete the reaction, separating the resulting dichloromethane layer from the reaction solution, washing it successively twice with water (200 ml), once with a saturated aqueous solution of sodium bicarbonate (150 ml) and twice with water (200 ml), drying over anhydrous magnesium sulfate, distilling off the solvent under reduced pressure, for concentration, purifying the concentrated residue according to silica gel chromatography using toluene as a developing solvent, and recrystallizing from heptane, to obtain colorless crystals (8.0 g). The crystals refer to 4-((E)-4-(trans-4-ethenylcyclohexyl)-1-butenyl)cyclohexanone.

In a 1 l, three-necked flask, equipped with a stirrer, a thermometer and a nitrogen gas-introducing tube, methoxymethyltriphenylphosphonium chloride (13.7 g, 40.0 mmol) was dissolved in THF (100 ml) in a nitrogen gas atmosphere, followed by cooling the solution down to −30° C. or lower, with an acetone-dry ice refrigerant carrier, adding potassium-t-butoxide (4.7 g, 42.1 mmol), agitating the mixture for 2 hours, while keeping the temperature at −30° C. or lower, dropwise adding a solution of 4-((E)-4-(trans-4-ethenylcyclohexyl)-1-butenyl)cyclohexanone (8.0 g, 30.8 mmol) dissolved in THF (30 ml) over 20 minutes, while keeping the same temperature, elevating the temperature up to room temperature over one hour, further agitating at room temperature for 4 hours, adding water (200 ml) to the reaction solution, to complete the reaction, extracting 3 times with toluene (150 ml), washing the resulting toluene layer three times with water (100 ml), drying over anhydrous magnesium sulfate, distilling off the solvent under reduced pressure, for concentration, and purifying the concentrated residue according to silica gel chromatography using toluene as a developing solvent, to obtain yellow-brown crystals (7.5 g).

In a 300 ml, eggplant type flask equipped with a cooling tube, the yellow-brown crystals (7.5 g) obtained according to the above process were dissolved in toluene (50 ml), followed by adding 99% formic acid (6.3 g, 135.0 mmol), heating the mixture under reflux for 2 hours, cooling the reaction solution down to room temperature, adding water (100 ml), separating the resulting organic layer, further extracting the aqueous layer with toluene (100 ml), combining the resulting organic layer with the above one, washing the organic layer successively twice with water (100 ml), once with a saturated aqueous solution of sodium bicarbonate (50 ml) and twice with water (100 ml), drying over anhydrous magnesium sulfate, and distilling off the solvent under reduced pressure, for concentration, to obtain yellow-brown crystals (6.9 g). The crystals refer to 4-((E)-4-(trans-4-ethenylcyclohexyl)-1-butenyl) cyclohexylcarbaldehyde.

In a 500 ml, three-necked flask equipped with a stirrer, a thermometer and a nitrogen gas-introducing tube, methyltriphenylphosphonium iodide (13.4 g, 33.1 mmol) was dissolved in THF (60 ml), followed by cooling the solution down to −30° C. or lower by means of an acetone-dry ice refrigerant carrier, adding potassium-t-butoxide (3.9 g, 34.8 mmol), agitating the mixture for 2 hours, while keeping the temperature at −30° C. or lower, dropwise dropping a solution of 4-((E)-4-(trans-4-ethenylcyclohexyl)-1-butenyl) cyclohexylcarbaldehyde (6.9 g, 25.5 mmol) dissolved in THF (30 ml) over 20 minutes, while keeping the same temperature, elevating the temperature up to room temperature over one hour, further agitating the mixture at room temperature for 4 hours, adding water (200 ml) to the reaction solution, to complete the reaction, extracting the solution twice with toluene (150 ml), washing the toluene layer three times with water (100 ml), drying over anhydrous magnesium sulfate, distilling off the solvent under reduced pressure, for concentration, purifying the concentrated residue according to silica gel chromatography using heptane as a developing solvent, to obtain colorless crystals (6.2 g), and recrystallizing the crystals from heptane, to obtain the captioned compound, trans-1-ethenyl-4-((E)-4-(trans-4-ethenylcyclohexyl)-1-butenyl)cyclohexane (2.8 g).

The measurement results of $^1$H-NMR and GC-MS intensely supported the structure of the present compound. GC-MS M$^+$272

When the starting substance or the reaction reagent are variously selected, the following compounds can be prepared according to the above preparation process:

trans-1-ethenyl-4-((E)-4-(trans-4-((E)-1-propenyl)-cyclohexyl)-1-butenyl)cyclohexane (No. 144)

trans-1-ethenyl-4-((E)-4-(trans-4-((E)-1-butenyl)-cyclohexyl)-1-butenyl)cyclohexane (No. 145)

trans-1-ethenyl-4-((E)-4-(trans-4-((E)-1-pentenyl)-cyclohexyl)-1-(butenyl)cyclohexane (No. 146)

trans-1-ethenyl-4-((E)-4-(trans-4-((Z)-2-propenyl)-cyclohexyl)-1-butenyl)cyclohexane trans-1-ethenyl-4-((E)-4-(trans-4-((Z)-2-butenyl)-cyclohexyl)-1-butenyl)cyclohexane trans-1-ethenyl-4-((E)-4-(trans-4-((E)-3-butenyl)-cyclohexyl)-1-butenyl)cyclohexane (No. 147)

trans-1-ethenyl-4-((E)-4-(trans-4-((E)-3-pentenyl)-cyclohexyl)-1-butenyl)cyclohexane (No. 148)

trans-1-((E)-1-propenyl)-4-((E)-4-(trans-4-((E)-1-propenyl)cyclohexyl)-1-butenyl)cyclohexane (No. 149)

trans-1-((E)-1-propenyl)-4-((E)-4-(trans-4-((E)-1-butenyl)cyclohexyl)-1-butenyl)cyclohexane (No. 150)

trans-1-((E)-1-propenyl)-4-((E)-4-(trans-4-((E)-1-pentenyl)cyclohexyl)-1-butenyl)cyclohexane (No. 151)

trans-1-((E)-1-propenyl)-4-((E)-4-(trans-4-((Z)-2-propenyl)cyclohexyl)-1-butenyl)cyclohexane trans-1-((E)-1-propenyl)-4-((E)-4-trans-4-((Z)-2-butenyl) cyclohexyl)-1-butenyl)cyclohexane trans-1-((E)-1-propenyl)-4-((E)-4-(trans-4-((E)-3-butenyl)cyclohexyl)-1-butenyl)cyclohexane (No. 152)

trans-1-((E)-1-propenyl)-4-((E)-4-(trans-4-((E)-3-pentenyl)cyclohexyl)-1-butenyl)cyclohexane (No. 153)

trans-1-((E)-3-butenyl)-4-((E)-4-(trans-4-((E)-1-propenyl)cyclohexyl)-1-butenyl)cyclohexane trans-1-((E)-3-butenyl)-4-((E)-4-(trans-4-((E)-1-butenyl) cyclohexyl)-1-butenyl)cyclohexane trans-1-((E)-3-butenyl)-4-((E)-4-trans-4-((E)-1-pentenyl) cyclohexyl)-1-butenyl)cyclohexane trans-1-((E)-3-butenyl)-4-((E)-4-(trans-4-((Z)-2-propenyl)cyclohexyl)-1-butenyl)cyclohexane trans-1-((E)-3-butenyl)-4-((E)-4-(trans-4-((Z)-2-butenyl) cyclohexyl)-1-butenyl)cyclohexane trans-1-((E)-3-butenyl)-4-((E)-4-(trans-4-((E)-3-butenyl) cyclohexyl)-1-butenyl)cyclohexane (No. 161)

trans-1-((E)-3-butenyl)-4-((E)-4-(trans-4-((E)-3-pentenyl)cyclohexyl)-1-butenyl)cyclohexane (No. 162)

trans-1-((E)-3-pentenyl)-4-((E)-4-(trans-4-((E)-1-propenyl)cyclohexyl)-1-butenyl)cyclohexane trans-1-((E)-3-pentenyl)-4-((E)-4-(trans-4-((E)-1-butenyl)cyclohexyl)-1-butenyl)cyclohexane trans-1-((E)-3-pentenyl)-4-((E)-4-(trans-4-((E)-1-pentenyl)cyclohexyl)-1-butenyl)cyclohexane trans-1-((E)-3-pentenyl)-4-((E)-4-(trans-4-((Z)-2-propenyl)cyclohexyl)-1-butenyl)cyclohexane trans-1-((E)-3-pentenyl)-4-((E)-4-(trans-4-((Z)-2-butenyl)cyclohexyl)-1-butenyl)cyclohexane trans-1-((E)-3-pentenyl)-4-((E)-4-(trans-4-((E)-3-butenyl)cyclohexyl)-1-butenyl)cyclohexane trans-1-((E)-pentenyl)-4-((E)-4-(trans-4-((E)-3-pentenyl)cyclohexyl)-1-butenyl)cyclohexane (No. 163).

EXAMPLE 5

Preparation of trans-1-(3-butenyl)-4-(4-(trans-4-(trans-4-propylcyclohexyl)cyclohexyl)butyl) cyclohexane (compound No. 213)

(wherein, in the formula (1), m=1; n=i=0; ring $A^1$=1,4-cyclohexylene group; $Z^1$=single bond, $R^1$=propyl group; $Z^3$=—$(CH_2)_4$—; and $R^2$=3-butenyl group)

In a 1 l. three-necked flask equipped with a stirrer, a thermometer and a nitrogen gas introducing tube, |1,3-dioxolan-2-yl)ethyl|triphenylphosphonium bromide (32.0 g, 72.2 mmol) was suspended in THF (300 ml) in a nitrogen gas atmosphere, followed by cooling the suspension down to −30° C. or lower by means of an aceton-dry ice refrigerant carrier, adding potassium-t-butoxide (8.5 g, 75.8 mmol), agitating the mixture for 2 hours, while keeping the temperature at −30° C. or lower, dropwise adding a solution of 4-(4-(trans-4-(trans-4-propylcyclohexyl)cyclohexyl)-butyl) cyclohexanone (20.0 g, 55.6 mmol) dissolved in THF (50 ml) over 20 minutes, while keeping the same temperature, elevating the temperature up to room temperature over one hour, further agitating the mixture at room temperature for 4 hours, adding water (200 ml) to the reaction solution, to complete the reaction, three times extracting with toluene (150 ml), three times washing the toluene layer with water (100 ml), drying over anhydrous magnesium sulfate, distilling off the solvent under reduced pressure, for concentration, and purifying the concentrated residue according to silica gel chromatography using toluene as a developing solvent, to obtain yellow-brown crystals (20.7 g).

In a 1 l. three-necked flask equipped with a stirrer, the yellow-brown crystals (20.7 g) obtained according to the above process were dissolved in a mixed solvent of toluene/ethanol (1:1) (150 ml), followed by adding 5%-Pd-C catalyst (1.9 g), carrying out catalytic hydrogen-reduction under a hydrogen pressure of 5 to 10 Kg/cm² at room temperature for 5 hours, filtering off the catalyst, and distilling off the solvent from the resulting reaction solution under reduced pressure, for concentration. In a 300 ml eggplant type flask equipped with a cooling tube, the concentrated residue was dissolved in toluene (200 ml), followed by adding 99% formic acid (10.7 g, 23.0 mmol), heating the mixture under reflux for 2 hours, cooling the reaction solution down to room temperature, adding water (100 ml), separating the organic layer, further extracting the aqueous layer with toluene (200 ml), combining the organic layers, washing the organic layer successively twice with water (100 ml), once with a saturated aqueous solution of sodium bicarbonate (50 ml) and twice with water (100 ml), drying over anhydrous magnesium sulfate, and distilling off the solvent under reduced pressure, for concentration, to obtain yellow-brown crystals (15.2 g). The crystals refer to 4-(4-(trans-4-(trans-4-propylcyclohexyl)cyclohexyl)butyl)-cyclohexylpropan-3-al.

In a 1 l. three-necked flask equipped with a stirrer, a thermometer and a nitrogen gas-introducing tube, methyltriphenylphosphonium iodide (19.9 9, 49.1 mmol) was suspended in THF (60 ml) in nitrogen gas atmosphere, followed by cooling the suspension down to −30° C. or lower by means of an acetone-dry ice refrigerant carrier, adding potassium-t-butoxide (5.8 g, 51.6 mmol), agitating the mixture for 2 hours, while cooling the temperature down to −30° C. or lower, dropwise adding a solution of 4-(4-(trans-4-(trans-4-propylcyclohexyl)cyclohexyl)butyl) cyclohexylpropan-3-al (15.2 g, 51.6 mmol) dissolved in THF (50 ml) over 15 minutes, while keeping the same temperature, elevating the temperature up to room temperature over one hour, further agitating the solution for 4 hours at room temperature, adding water (100 ml) to the reaction solution, to complete the reaction, three times extracting the solution with toluene (100 ml), washing the toluene layer three times with water (100 ml), drying over anhydrous magnesium sulfate, distilling off the solvent under reduced pressure, for concentration, purifying the concentrated residue according to silica gel chromatography using heptane as a developing solvent, and recrystallizing from heptane, to obtain colorless crystals (5.5 g).

The crystals refer to the captioned compound, trans-1-(3-butenyl)-4-(4-(trans-4-(trans-4-propylcyclohexyl)-cyclohexyl)butyl)cyclohexane.

The measurement results intensely supported the structure of the present compound.

GC-MS: $M^+272$

When 4-(4-(trans-4-(trans-4-(trans-4-propylcyclohexyl)cyclohexyl)butyl)cyclohexanone according to the above preparation process is replaced by 4-(4-(trans-4-(trans-4-(trans-4-alkylcyclohexyl)cyclohexyl)butyl)cyclohexanones having different chain lengths of alkyl group, the following compounds can be prepared according to the above preparation process:

trans-1-(3-butenyl)-4-(4-(trans-4-(trans-4-ethylcyclohexyl)cyclohexyl)butyl)cyclohexane (No. 212)

trans-1-(3-butenyl)-4-(4-(trans-4-(trans-4-butylcyclohexyl)cyclohexyl)butyl)cyclohexane trans-1-(3-butenyl)-4-(4-(trans-4-(trans-4-pentylcyclohexyl)cyclohexyl)butyl)cyclohexane (No. 214)

trans-1-(3-butenyl)-4-(4-trans-4-(trans-4-hexylcyclohexyl)cyclohexyl)butyl)cyclohexane trans-1-(3-butenyl)-4-(4-trans-4-(trans-4-heptylcyclohexyl)cyclohexyl)butyl)cyclohexane trans-1-(3-butenyl)-4-(4-trans-4-(trans-4-octylcyclohexyl)cyclohexyl)butyl)cyclohexane trans-1-(3-butenyl)-4-(4-trans-4-(trans-4-nonylcyclohexyl)cyclohexyl)butyl)cyclohexane trans-1-(3-butenyl)-4-(4-trans-4-(trans-4-decylcyclohexyl)butyl)cyclohexane trans-1-ethenyl-4-(4-(trans-4-(trans-4-ethylcyclohexyl cyclohexyl)butyl)cyclohexane (No. 200)

trans-1-ethenyl-4-(4-(trans-4-(trans-4-propylcyclohexyl cyclohexyl) butyl) cyclohexane (No. 201)

trans-1-ethenyl-4-(4-trans-4-(trans-4-pentylcyclohexyl cyclohe;,yl)butyl)cyclohexane (No. 202)

trans-1-((E)-1-propenyl)-4-(4-(trans-4-(trans-4-ethylcyclohexyl)cyclohexyl)butyl)cyclohexane (No 203)

trans-1-((E)-1-propenyl)-4-(4-(trans-4-(trans-4-propylcyclohexyl)cyclohexyl)butyl)cyclohexane (No 204)

trans-1-((E)-1-propenyl)-4-(4-(trans-4-(trans-4-pentylcyclohexyl)cyclohexyl)butyl)cyclohexane (No 205)

trans-1-((E)-3-pentenyl)-4-(4-(trans-4-(trans-4-ethylcyclohexyl)cyclohexyl)butyl)cyclohexane (No. 215)

trans-1-((E)-3-pentenyl)-4-(4-(trans-4-(trans-4-propylcyclohexyl)cyclohexyl)butyl)cyclohexane (No. 216)

trans-1-((E)-3-pentenyl)-4-(4-(trans-4-(trans-4-pentylcyclohexyl)cyclohexyl)butyl)cyclohexane (No. 217)

EXAMPLE 6

Preparation of trans-1-ethenyl-4-((E)-4-(trans-4-(trans-4-propylcyclohexyl)cyclohexyl)-1-butenyl)-cyclohexane (compound No. 237)

(wherein, in the formula (1), m=1; n=i=0; ring $A^1$=1,4-cyclohexylene group; $Z^1$=single bond; $R^1$=n-propyl group; $Z^3$=—(CH$_2$)$_2$—CH=CH—; and $R^2$=ethenyl group)

In a 2 l, three-necked flask equipped with a stirrer, a thermometer and a nitrogen gas-introducing tube, 1-(trans-4-(trans-4-propylcyclohexyl)cyclohexyl) propyltriphenylphosphine iodide (164.6 g, 258.0 mmol) was suspended in THF (500 ml), followed by cooling the suspension down to −30° C. or lower by means of an acetone-dry ice refrigerant carrier, adding potassium-t-butoxide (30.4 g, 271.0 mmol), stirring the mixture for 2 hours, while keeping the temperature at −30° C. or lower, dropwise adding a solution of 4-formylcyclohexanone (25.0 g, 198 mmol) dissolved in THF (100 ml), over 50 minutes, while keeping the same temperature, elevating the temperature up to room temperature over one hour, further agitating the mixture for 4 hours, adding water (500 ml) to the reaction solution, to complete the reaction, extracting 3 times with toluene (300 ml), three times washing the toluene layer with water (500 ml), drying over anhydrous magnesium sulphate, distilling off the solvent under reduced pressure, for concentration, and purifying the concentrated residue, as it was, according to silica gel chromatography using toluene as a developing solvent, to obtain yellow-brown crystals (63.1 g).

In a 1 liter eggplant type flask equipped with a cooling tube, the yellow-brown color crystals (63.1 g) obtained according to the above process were dissolved in toluene/ethanol (1/1) mixed solvent, followed by adding sodium benzene sulfinate (43.3 g) and 6N hydrochloric acid (44.0 mml) and heating the mixture under reflux for 10 hours, cooling the reaction solution down to room temperature and adding water (300 ml) to complete the reaction. The reaction solution was extracted twice with toluene (300 ml), following by washing the toluene layer thereof twice with water (200 ml), once with a saturated aqueous solution of sodium hydrogen carbonate (250 ml), twice washing with water (300 ml), drying over anhydrous MgSO$_4$, distilling off the solvent under reduced pressure, and concentrating. The concentrated residue is purified according to silica gel chromatography using toluene as a developing agent, and recrystallized with heptane, to obtain colorless crystals (43.5 g). The crystals refer to 4-((E)-4-(trans-4-(trans-4-propylcyclohexyl)cyclohexyl)-1-butenyl)cyclohexanone.

In a 1 liter, three-necked flask equipped with a stirrer, a thermometer and a nitrogen gas-introducing tube, methoxymethyltriphenylphosphonium chrolide (53.9 g) (157.0 mmol) was dissolved in THF (200 ml), followed by cooling the solution down to −30° C. or lower by means of an acetone-dry ice coolant, adding potassium-t-butoxide (18.5 g)(165.0 mmol), stirring the mixture for 2 hours, while keeping the temperature at −30 ° C. or lower, dropwise adding a solution of 4-((E)-4-(trans-4-(trans-4-propylcyclohexyl)cyclohexyl)-1-butenyl)cyclohexanone (43.5 g)(121.0 mmol) dissolved in THF (150 ml), over 50 minutes, while keeping the same temperature, elevating the temperature up to room temperature over 1 hour, further stirring the mixture for 4 hours at room temperature, and adding water (300 ml) to the reacted solution, to complete the reaction, the reaction solution was extracted twice with toluene (250 ml), followed by three times washing the toluene layer with water (200 ml), drying over anhydrous magnesium sulphate, distilling off the solvent under reduced pressure, for concentration, and purifying the concentrated residue according to silica gel chromatography using toluene as a developing solvent, to obtain yellow-brown crystals (40.3 g).

In a 1 liter eggplant type flask equipped with a cooling tube, the yellow-brown color crystals (40.3 g) obtained according to the above process were dissolved in toluene (300 ml), followed by adding 99% formic acid (24.6 g, 535 mmol) and heating the mixture under reflux for 2 hours, cooling the reaction solution down to room temperature, adding water (200 ml), separating an organic layer, further extracting the the aqueous solution with toluene (300 ml), combining the extract with the organic layer, washing the resulting organic layer successively twice with water (200 ml), once with a saturated aqueous solution of sodium hydrogen carbonate (150 ml) and twice with water (200 ml), drying the organic layer over anhydrous magnesium sulfate, distilling off the solvent under reduced pressure, for concentration, to obtain yellow-brown color crystals (35.8 g)

The crystals refer to 4-((E)-4-(trans-4-(trans-4-propylcyclohexyl)cyclohexyl)-1-butenyl)cyclohexylcarbaldehyde.

In a 1 liter, three-necked equipped with a stirrer, a thermometer and a nitrogen gas-introducing tube, methyltriphenylphosphonium iodide (50.6 g)(125.0 mmol) was dissolved in THF (200 ml), followed by cooling the solution down to −30° C. or lower by means of an acetone-dry ice coolant, adding potassium-t-butoxide (14.7 g)(131.0 mmol), stirring the mixture for 2 hours, while keeping the temperature at −30° C. or lower, dropwise adding a solution of 4-((E)-4-(trans-4-(trans-4-propylcyclohexyl)cyclohexyl)-1-butenyl)cyclohexylcarbaldehyde (35.8 g)(96.3 mmol) dissolved in THF (100 ml), over 30 minutes, while keeping the same temperature, elevating the temperature up to room temperature over 1 hour, further stirring the mixture for 4 hours at room temperature, and adding water (200 ml) to the reacted solution, to complete the reaction. The solution was extracted twice with toluene (250 ml), followed by three times washing the toluene layer with water (200 ml), drying over anhydrous magnesium sulphate, distilling off the solvent under reduced pressure, for concentration, purifying the concentrated residue according to silica gel chromatography using heptane as a developing solvent, to obtain colorless crystals (31.7 g). The crystals were recrystallized from heptane, for purification, to obtain the captioned compound, trans-1-ethenyl-4-((E)-4-(trans-4-(trans-4-propylcyclohexyl)cyclohexyl)-1-butenyl)cyclohexane.

The measurement results of $^1$H-NMR and GC-MS intensely supported the structure of the present compound. GC-MS: M$^+$ 370

When 1-(trans-4-(trans-4-propylcyclohexyl)cyclohexyl) propyltriphenylphosphine iodide used in the above preparation process is replaced by 1-(trans-4-(trans-4-alkylcyclohexyl)cyclohexyl)propyltriphenylphosphine iodide having a different chain length of alkyl group and the latter is processed according to the above preparation process, the following compounds can be prepared;

trans-1-ethenyl-4-((E)-4-(trans-4-(trans-4-methylcyclohexyl)cyclohexyl)-1-butenyl)cyclohexane trans-1-ethenyl-4-((E)-4-(trans-4-(trans-4-ethylcyclohexyl)cyclohexyl)-1-butenyl)cyclohexane (No. 236)

trans-1-ethenyl-4-((E)-4-(trans-4-(trans-4-butylcyclohexyl)cyclohexyl)-1-butenyl)cyclohexane trans-1-ethenyl-4-((E)-4-(trans-4-(trans-4-pentylcyclohexyl)cyclohexyl)-1-butenyl)cyclohexane (No. 238)

trans-1-ethenyl-4-((E)-4-(trans-4-(trans-4-hexylcyclohexyl)cyclohexyl)-1-butenyl)cyclohexane trans-1-ethenyl-4-((E)-4-(trans-4-(trans-4-heptylcyclohexyl)cyclohexyl)-1-butenyl)cyclohexane trans-1-ethenyl-4-((E)-4-(trans-4-(trans-4-octylcyclohexyl)cyclohexyl)-1-butenyl)cyclohexane trans-1-ethenyl-4-((E)-4-(trans-4-(trans-4-nonylcyclohexyl)cyclohexyl)-1-butenyl)cyclohexane trans-1-ethenyl-4-((E)-4-(trans-4-(trans-4-decylcyclohexyl)cyclohexyl)-1-butenyl)cyclohexane When the starting substance or the reaction reagent are variously selected, the following compounds can be prepared according to the above preparation process:

trans-1-((E)-1-propenyl)-4-((E)-4-(trans-4-(trans-4-ethylcyclohexyl)cyclohexyl)-1-butenyl)cyclohexane (No. 239)

trans-1-((E)-1-propenyl)-4-((E)-4-(trans-4-(trans-4-propylcyclohexyl)cyclohexyl)-1-butenyl)cyclohexane (No. 240)

trans-1-((E)-1-propenyl)-4-((E)-4-(trans-4-(trans-4-pentylcyclohexyl)cyclohexyl)-1-butenyl)cyclohexane (No. 241)

trans-1-((E)-butenyl)-4-((E)-4-(trans-4-(trans-4-ethylcyclohexyl)cyclohexyl)-1-butenyl)cyclohexane (No. 242)

trans-1-((E)-1-butenyl)-4-((E)-4-(trans-4-(trans-4-propylcyclohexyl)cyclohexyl)-1-butenyl)cyclohexane (No. 243)

trans-1-((E)-1-butenyl)-4-((E)-4-(trans-4-(trans-4-pentylcyclohexyl)cyclohexyl)-1-butenyl)cyclohexane (No. 244)

trans-1-(3-butenyl)-4-((E)-4-(trans-4-(trans-4-ethylcyclohexyl)cyclohexyl)-1-butenyl)cyclohexane (No. 248)

trans-1-(3-butenyl)-4-((E)-4-(trans-4-(trans-4-propylcyclohexyl)cyclohexyl)-1-butenyl)cyclohexane (No. 249)

trans-1-(3-butenyl)-4-((E)-4-(trans-4-(trans-4-pentylcyclohexyl)cyclohexyl)-1-butenyl)cyclohexane (No. 250)

trans-1-((E)-3-pentenyl)-4-((E)-4-(trans-4-(trans-4-ethylcyclohexyl)cyclohexyl)-1-butenyl)cyclohexane (No. 251)

trans-1-((E)-3-pentenyl)-4-((E)-4-(trans-4-(trans-4-propylcyclohexyl)cyclohexyl)-1-butenyl)cyclohexane (No. 252)

trans-1-((E)-3-pentenyl)-4-((E)-4-(trans-4-(trans-4-pentylcyclohexyl)cyclohexyl)-1-butenyl)cyclohexane (No. 253)

trans-1-ethenyl-4-((E)-4-(trans-4-(trans-4-ethylcyclohexyl)cyclohexyl)-3-butenyl)cyclohexane (No. 218)

trans-1-ethenyl-4-((E)-4-(trans-4-(trans-4-propylcyclohexyl)cyclohexyl)-3-butenyl)cyclohexane (No. 219)

trans-1-ethenyl-4-((E)-4-(trans-4-(trans-4-pentylcyclohexyl)cyclohexyl)-3-butenyl)cyclohexane (No. 220)

trans-1-((E)-1-propenyl)-4-((E)-4-(trans-4-(trans-4-ethylcyclohexyl)cyclohexyl)-3-butenyl)cyclohexane (No. 221)

trans-1-((E)-propenyl)-4-((E)-4-(trans-4-(trans-4-propylcyclohexyl)cyclohexyl)-3-butenyl)cyclohexane (No. 222)

trans-1-((E)-1-propenyl)-4-((E)-4-(trans-4-(trans-4-pentylcyclohexyl)cyclohexyl)-3-butenyl)cyclohexane (No. 223)

trans-1-((E)-butenyl)-4-((E)-4-(trans-4-(trans-4-ethylcyclohexyl)cyclohexyl)-3-butenyl)cyclohexane (No. 224)

trans-1-((E)-butenyl)-4-((E)-4-(trans-4-(trans-4-propylcyclohexyl)cyclohexyl)-3-butenyl)cyclohexane (No. 225)

trans-1-((E)-1-butenyl)-4-((E)-4-(trans-4-(trans-4-pentylcyclohexyl)cyclohexyl)-3-butenyl)cyclohexane (No. 226)

trans-1-(3-butenyl)-4-((E)-4-(trans-4-(trans-4-ethylcyclohexyl)cyclohexyl)-3-butenyl)cyclohexane (No. 230)

trans-1-(3-butenyl)-4-((E)-4-(trans-4-(trans-4-propylcyclohexyl)cyclohexyl)-3-butenyl)cyclohexane (No. 231)

trans-1-(3-butenyl)-4-((E)-4-(trans-4-(trans-4-pentylcyclohexyl)cyclohexyl)-3-butenyl)cyclohexane (No. 232)

trans-1-((E)-3-pentenyl)-4-((E)-4-(trans-4-(trans-4-ethylcyclohexyl)cyclohexyl)-3-butenyl)cyclohexane (No. 233)

trans-1-((E)-3-pentenyl)-4-((E)-4-(trans-4-(trans-4-propylcyclohexyl)cyclohexyl)-3-butenyl)cyclohexane (No. 234)

trans-1-((E)-3-pentenyl)-4-((E)-4-(trans-4-(trans-4-pentylcyclohexyl)cyclohexyl)-3-butenyl)cyclohexane (No. 235)

EXAMPLE 7

Preparation of trans-1-ethenyl-4-((E)-4-((E)-2-(trans-4-(trans-4-propylcyclohexyl)ethenyl)cyclohexyl)-3-butenyl) cyclohexane(compound No.307)

(Wherein, in the formula (I), m=1, n=i=0, ring $A^1$=1,4-cyclohexylene group, $Z^1$=—CH=CH—, $R^1$=n-propyl group, $Z^3$=—CH=CH—$(CH_2)_2$—, and $R^2$=ethenyl group):

In a 1 litter, three-necked flask equipped with a stirrer, a thermometer and a nitrogen gas introducing tube, trans-4-propylcyclohexylmethyl iodide (37.6 g)(71.2 mmol) was suspended in THF (200 ml) in a nitrogen gas atmosphere, followed by cooling the suspension down to −30° C. or lower by means of an acetone-dry ice coolant, adding potassium-t-butoxide (8.4 g)(74.7 mmol), stirring the mixture for 2 hours, while keeping the temperature at −30° C. or lower, dropwise adding a solution of 4-((E)-4-(trans-4-ethenylcyclohexyl)-1-butenyl)cyclohexylcarbaldehyde (15.0 g) (54.7 mmol) prepared according to the process described in Example 4, and dissolved in THF (60 ml) over 15 minutes, while keeping the same temperature, elevating the temperature up to room temperature over 30 minutes further stirring the mixture at room temperature for 4 hours and adding water (100 ml) to the reaction solution to complete the reaction. The reaction solution was extracted three times with toluene (150 ml), following by washing the toluene layer thereof three times with water (100 ml), drying over anhydrous magnesium sulfate, distilling off the solvent under reduced pressure, for concentration, and purifying the concentrated residue according to silica gel chromatography using heptane as a developing solvent, to obtain colorless crystals (13.7 g).

In a 500 ml), eggplant type flask equipped with a cooling tube, the colorless crystals (13.7 g) obtained according to the above process was dissolved in a mixed solvent of toluene/ ethanol(1:1)(100 ml), followed by adding sodium benzenesulfinate (8.5 g) and 6N-hydrochloric acid (8.6 ml), heating the mixture under reflux for 10 hours, cooling it down to room temperature, and adding water (100 ml) to complete the reaction. The reaction solution was extracted twice with toluene (100 ml), following by washing the toluene layer successively twice with water (100 ml), once with a saturated aqueous solution of sodium hydrogen carbonate (50 ml) and further, twice with water (100 ml), drying over anhydrous magnesium sulfate, distilling off the solvent under reduced pressure,for concentration, purifying the concentrated residue according to silica gel chromatography using heptane as a developing solvent, and recrystallizing it from heptane, to obtain the captioned compound of colorless crystals, trans-1-ethenyl-4-((E)-4-((E)-2-(trans-4-(trans-4-propylcyclohexyl)ethenyl) cyclohexyl)-3-butenyl) cyclohexane (2.1 g).

The measurement results of $^1$H-NMR and GC-MS intensely supported the structure of the present compound. GC-MS: $M^{+3}$396

When trans-4-propylcyclohexylmethyl iodide used in the above preparation process is replaced by trans-4-alkylcyclohexylmethyl iodide having a different chain length of alkyl group and the latter is processed according to the above preparation process, the following compounds can be prepared;

trans-1-ethenyl-4-((E)-4-((E)-2-(trans-4-(trans-4-methylcyclohexyl)ethenyl)cyclohexyl)-3-butenyl) cyclohexane
  trans-1-ethenyl-4-((E)-4-((E)-2-(trans-4-(trans-4-ethylcyclohexyl)ethenyl)cyclohexyl)-3-butenyl) cyclohexane
  trans-1-ethenyl-4-((E)-4-((E)-2-(trans-4-(trans-4-butylcyclohexyl)ethenyl)cyclohexyl)-3-butenyl) cyclohexane
  trans-1-ethenyl-4-((E)-4-((E)-2-(trans-4-(trans-4-pentylcyclohexyl)ethenyl)cyclohexyl)-3-butenyl) cyclohexane
  trans-1-ethenyl-4-((E)-4-((E)-2-(trans-4-(trans-4-hexylcyclohexyl)ethenyl)cyclohexyl)-3-butenyl) cyclohexane
  trans-1-ethenyl-4-((E)-4-((E)-2-(trans-4-(trans-4-heptylcyclohexyl)ethenyl)cyclohexyl)-3-butenyl) cyclohexane
  trans-1-ethenyl-4-((E)-4-((E)-2-(trans-4-(trans-4-octylcyclohexyl)ethenyl)cyclohexyl)-3-butenyl) cyclohexane
  trans-1-ethenyl-4-((E)-4-((E)-2-(trans-4-(trans-4-nonylcyclohexyl)ethenyl)cyclohexyl)-3-butenyl) cyclohexane
  trans-1-ethenyl-4-((E)-4-((E)-2-(trans-4-(trans-4-decylcyclohexyl)ethenyl)cyclohexyl)-3-butenyl) cyclohexane When the starting substance or the reaction reagent are variously selected, the following compounds can be prepared according to the above preparation process;

trans-1-((E)-1-propenyl)-4-((E)-4-((E)-2-(trans-4-(trans-4-ethylcyclohexyl)ethenyl)cyclohexyl)-3-butenyl) cyclohexane
trans-1-((E)-1-propenyl)-4-((E)-4-((E)-2-(trans-4-(trans-4-propylcyclohexyl)ethenyl)cyclohexyl)-3-butenyl) cyclohexane
trans-1-((E)-1-propenyl)-4-((E)-4-((E)-2-(trans-4-(trans-4-pentylcyclohexyl)ethenyl)cyclohexyl)-3-butenyl) cyclohexane
trans-1-((E)-1-butenyl)-4-((E)-4-((E)-2-(trans-4-(trans-4-ethylcyclohexyl)ethenyl)cyclohexyl)-3-butenyl) cyclohexane
trans-1-((E)-1-butenyl)-4-((E)-4-((E)-2-(trans-4-(trans-4-propylcyclohexyl)ethenyl)cyclohexyl)-3-butenyl) cyclohexane
trans-1-((E)-1-butenyl)-4-((E)-4-((E)-2-(trans-4-(trans-4-pentylcyclohexyl)ethenyl)cyclohexyl)-3-butenyl) cyclohexane
trans-1-(3-butenyl)-4-((E)-4-((E)-2-(trans-4-(trans-4-ethylcyclohexyl)ethenyl)cyclohexyl)-3-butenyl) cyclohexane
trans-1-(3-butenyl)-4-((E)-4-((E)-2-(trans-4-(trans-4-propylcyclohexyl)ethenyl)cyclohexyl)-3-butenyl) cyclohexane
trans-1-(3-butenyl)-4-((E)-4-((E)-2-(trans-4-(trans-4-pentylcyclohexyl)ethenyl)cyclohexyl)-3-butenyl) cyclohexane
trans-1-((E)-3-pentenyl)-4-((E)-4-((E)-2-(trans-4-(trans-4-ethylcyclohexyl)ethenyl)cyclohexyl)-3-butenyl) cyclohexane
trans-1-((E)-3-pentenyl)-4-((E)-4-((E)-2-(trans-4-(trans-4-propylcyclohexyl)ethenyl)cyclohexyl)-3-butenyl) cyclohexane
trans-1-((E)-3-pentenyl)-4-((E)-4-((E)-2-(trans-4-(trans-4-pentylcyclohexyl)ethenyl)cyclohexyl)-3-butenyl) cyclohexane
trans-1-ethenyl-4-((E)-4-((E)-2-(trans-4-(trans-4-ethylcyclohexyl)ethenyl)cyclohexyl)-1-butenyl) cyclohexane
trans-1-ethenyl-4-((E)-4-((E)-2-(trans-4-(trans-4-propylcyclohexyl)ethenyl)cyclohexyl)-1-butenyl) cyclohexane
trans-1-ethenyl-4-((E)-4-((E)-2-(trans-4-(trans-4-pentylcyclohexyl)ethenyl)cyclohexyl)-1-butenyl) cyclohexane
trans-1-((E)-1-propenyl)-4-((E)-4-((E)-2-(trans-4-(trans-4-ethylcyclohexyl)ethenyl)cyclohexyl)-1-butenyl) cyclohexane (No. 308)
trans-1-((E)-1-propenyl)-4-((E)-4-((E)-2-(trans-4-(trans-4-propylcyclohexyl)ethenyl)cyclohexyl)-1-butenyl) cyclohexane (No. 309)
trans-1-((E)-1-propenyl)-4-((E)-4-((E)-2-(trans-4-(trans-4-pentylcyclohexyl)ethenyl)cyclohexyl)-1-butenyl) cyclohexane
trans-1-((E)-1-butenyl)-4-((E)-4-((E)-2-(trans-4-(trans-4-ethylcyclohexyl)ethenyl)cyclohexyl)-1-butenyl) cyclohexane
trans-1-((E)-1-butenyl)-4-((E)-4-((E)-2-(trans-4-(trans-4-propylcyclohexyl)ethenyl)cyclohexyl)-1-butenyl) cyclohexane
trans-1-((E)-1-butenyl)-4-((E)-4-((E)-2-(trans-4-(trans-4-pentylcyclohexyl)ethenyl)cyclohexyl)-1-butenyl) cyclohexane
trans-1-(3-butenyl)-4-((E)-4-((E)-2-(trans-4-(trans-4-ethylcyclohexyl)ethenyl)cyclohexyl)-1-butenyl) cyclohexane (No. 310)
trans-1-(3-butenyl)-4-((E)-4-((E)-2-(trans-4-(trans-4-propylcyclohexyl)ethenyl)cyclohexyl)-1-butenyl) cyclohexane trans-1-(3-butenyl)-4-((E)-4-((E)-2-(trans-4-(trans-4-pentylcyclohexyl)ethenyl)cyclohexyl)-1-butenyl)cyclohexane trans-1-((E)-3-pentenyl)-4-((E)-4-((E)-2-(trans-4-(trans-4-ethylcyclohexyl)ethenyl)cyclohexyl)-1-butenyl)cyclohexane trans-1-((E)-3-pentenyl)-4-((E)-4-((E)-2-(trans-4-(trans-4-propylcyclohexyl)ethenyl)cyclohexyl)-1-butenyl)cyclohexane (No. 311)

trans-1-((E)-3-pentenyl)-4-((E)-4-((E)-2-(trans-4-(trans-4-pentylcyclohexyl)ethenyl)cyclohexyl)-1-butenyl)cyclohexane

EXAMPLE 8 (Use Example 1)

A nematic liquid crystal composition having the following constitution has the clearing point (Cp) of 72.4° C.

4-(trans-4-propylcyclohexyl)benzonitrile 24% by weight
4-(trans-4-pentylcyclohexyl benzonitrile 36% by weight
4-(trans-4-heptylcyclohexyl)benzonitrile 25% by weight
4-(4-propylphenyl)benzonitrile 15% by weight A TN cell (twisted nematic cell) having a cell thickness of 9 μm enclosed with the above liquid crystal composition gives a threshold voltage (Vth) of 1.78 V, a dielectric anisotropy value ($\Delta\epsilon$) of +11.0, an optical anisotropy value ($\Delta n$) of 0.137, and a viscosity at 20° C. ($\eta 20$) of 27.0 mPa·s.

With this liquid composition (85 parts by weight) as a mother liquid crystal (hereinafter referred to Mother liquid A), was mixed 1-ethenyl-4-(4-(trans-4-pentylcyclohexyl)butyl)cyclohexane (Compound No.5) (15 parts by weight) shown in Example 1. The physical properties of the mixture were measured to be Cp: 71.5° C., Vth: 1.78 V, $\Delta\epsilon$:9.4, $\Delta n$:0.120, $\eta 20$:20.1 mPa·s. The composition was allowed to stand in a freezer at −20° C. , but no deposition of crystals was observed even after 40 days.

EXAMPLE 9 (Use Example 2)

The mother liquid crystal A (85 parts by weight) shown in Example 8 was mixed with 1-ethenyl-4-(4-(trans-4-propylcyclohexyl)butyl)cyclohexane (Compound No.3) (15 parts by weight) shown in Example 1. The physical properties of the mixture were measured to be Cp: 65.7° C. , Vth: 1.76 V, $\Delta\epsilon$:9.3, $\Delta n$:0.121, $\eta 20$:19.8 mPa·s. The composition was allowed to stand in a freezer at −20° C., but no deposition of crystals was observed even after 40 days.

Composition Example

As a compound to be compared with the compound of the present invention, trans-4-(trans-4-(3(E)-pentenyl)cyclohexyl)propylcyclohexane (a-1) and trans-4-(trans-4-(1(E)-pentenyl)cyclohexyl)ethylcyclohexane (a-2) described in the prior art column of Japanese patent application laid-open No. 61-83136 were prepared according to the method described in the publication.

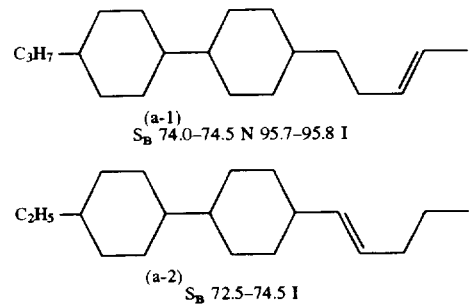

(a-1)
$S_B$ 74.0–74.5 N 95.7–95.8 I (a-2)
$S_B$ 72.5–74.5 I

A liquid crystal composition of the above mother liquid A (85 parts by weight) and each of the above compounds (a-1) and (a-2)(15 parts by weight) was prepared and measured in its physical properties. Further, in order to evaluate its miscibility, each liquid crystal composition was allowed to stand in a freezer at −20° C. , and measured in a time until crystals deposit in the liquid crystal composition from the beginning of the time to stand. The results are shown in Table 1 as well as the measurement results in Example 9.

TABLE 1

|  | NI(°C.) | $\Delta\epsilon$ | $\Delta n$ | $\eta_{20}$ (mPa·s) | $K_{33}/K_{11}$ | *1 miscibility (days) |
|---|---|---|---|---|---|---|
| Mother crystal A | 72.4 | 11.0 | 0.137 | 27.0 | — | — |
| C₃H₇—⬡—⬡—\\ (No.3) | 65.7 | 9.3 | 0.121 | 19.8 | 2.08 | >40 |
| C₃H₇—⬡—⬡—// (a-1) | 74.8 | 9.4 | 0.127 | 22.3 | 2.00 | 13 |
| C₂H₅—⬡—⬡—\/ (a-2) | 65.6 | 9.1 | 0.119 | 21.5 | 1.88 | 18 |

*1 Days until crystals (solid) deposit after allowing to stand in a freezer at −20° C.

As known from the Table, the liquid crystal composition using the compound of the present invention (No. 3) has a very low viscosity in proportion to its high clearing point.

As the viscosity was lowered by about 30% than that of the mother liquid crystal A by the addition of 15% by weight of the compound to the mother liquid crystal A, the compound No.3 was found to be an excellent compound as a viscosity decreasing agent. Further, as to an elastic constant ratio, as compared with compositions using the compound (a-1) or (a-2), the present composition has a very large elastic constant ratio. More further, as to miscibility, the compound of the present invention exhibits a very good miscibility at lower temperatures, such that the liquid crystal composition prepared from the compound of the present invention has no deposition of crystals (solid) even after 40 days standing in a freezer at −20° C., as compared with that the liquid crystal composition prepared from the compound (a-1) or (a-2) has observed deposition of crystals within 3 weeks in the freezer.

As described in the prior art column, since liquid crystalline compounds are usually used in liquid crystal compositions, their miscibility is a very important property. Particularly, miscibility at lower temperatures is the most important characteristic in liquid crystal display elements applied to airplanes and cars which suffer a large temperature change. As apparent from the above comparative tests, the compounds of the present invention have a large elastic constant ratio as well as a very excellent miscibility at lower temperatures, and further has a low viscosity, which are characteristic not to be found in the other compounds having similar structures.

Other use example of the compound of the present invention (Use example 3 to 22) will be described as follows. The compounds in the following Use examples are described by using abbreviated symbols which are defined in the following Table 2. Further, in the Use examples, $T_{NI}$ represents nematic-isotropic liquid transferring temperature, η represents viscosity (mPa·s), Δn represents optical anisotropy value, Δε represents dielectric anisotropy value, Vth represents threshold voltage (V).

TABLE 2

| 1) Left end group | Symbol | 3) Bonding group | Symbol |
|---|---|---|---|
| $C_rH_{2r+1}-$ | s− | $-C_2H_4-$ | 2 |
| $C_rH_{2r+1}O-$ | sO− | $-C_4H_8-$ | 4 |
| $C_2H_{2r+1}OC_rH_{2t}-$ | sOt− | −COO− | E |
| $CH_2=CH-$ | V− | $-C\equiv C-$ | T |
| $CH_2=CHC_rH_{2t}-$ | Vs− | −CH=CH− | V |
| $C_rH_{2r+1}CH=CHC_rH_{2t}-$ | sVt− | $-CF_2O-$ | CF2O |
| $C_2H_{2r+1}CH=CHC_rH_{2t}CH=CHC_uH_{2u}-$ | sVtVu− | $-OCF_2-$ | OCF2 |

| 2) Ring structure | Symbol | 4) Right end group | Symbol |
|---|---|---|---|
| 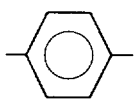 | B | −F<br>−Cl | −F<br>−CL |
| 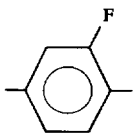 | B(F) | −CN<br>$-CF_3$ | −C<br>−CF3 |
| 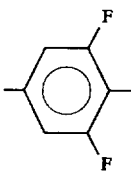 | B(F, F) | $-OCF_3$<br>$-OCF_2H$ | −OCF3<br>−OCF2H |
| 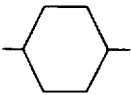 | H | $-C_rH_{2r+1}$<br>$-OC_rH_{2r+1}$ | −s<br>−Os |
| 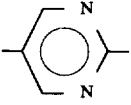 | Py | $-COOCH_3$ | −EMe |
| 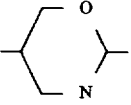 | D | $-C_rH_{2t}CH=CH_2$ | −sV |

TABLE 2-continued

| | Ch | $-C_rH_{2r}CH=CHC_sH_{2s+1}$ | $-tVs$ |

5) Examples for description

EX. 1  3-H2B(F, F)B(F)—F

EX. 3  IV2-BEB(F, F)—C

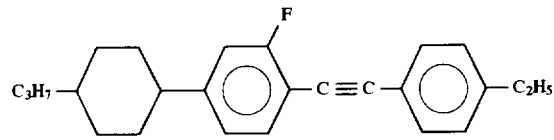

EX. 2  3-HB(F)TB-2

Use Example 3

| | |
|---|---|
| V-H4H-2 (Compound No. 2) | 5.0% |
| 1V2-BEB (F, F)-C | 5.0% |
| 3-HB-C | 25.0% |
| 1-BTB-3 | 5.0% |
| 2-BTB-1 | 10.0% |
| 3-HH-4 | 6.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB (F) TB-2 | 6.0% |
| 3-HB (F) TB-3 | 6.0% |
| $T_{NI}$ = 87.8 (°C.) | |
| η = 15.0 (mPa · s) | |
| Δn = 0.161 | |
| Δε = 7.1 | |
| $V_{th}$ = 2.10 (V) | |

Use Example 4

| | |
|---|---|
| V-H4H-2 (Compound No. 2) | 4.0% |
| V-H4H-3 (Compound No. 3) | 4.0% |
| V-H4H-5 (Compound No. 5) | 2.0% |
| V2-HB-C | 12.0% |
| 1V2-HB-C | 12.0% |
| 3-HB-C | 24.0% |
| 3-HB (F)-C | 5.0% |
| 2-BTB-1 | 2.0% |
| 3-HH-4 | 4.0% |
| 2-HHB-C | 3.0% |
| 3-HHB-C | 6.0% |
| 3-HB (F) TB-2 | 8.0% |
| 3-H2BTB-2 | 5.0% |
| 3-H2BTB-3 | 5.0% |
| 3-H2BTB-4 | 4.0% |
| $T_{NI}$ = 85.2 (°C.) | |
| η = 18.2 (mPa · s) | |
| Δn = 0.152 | |
| Δε = 8.6 | |
| $V_{th}$ = 2.00 (V) | |

Use Example 5

| | |
|---|---|
| V-H4H-5 (Compound No. 5) | 3.0% |
| 201-BEB (F)-C | 5.0% |
| 301-BEB (F)-C | 15.0% |
| 401-BEB (F)-C | 13.0% |
| 501-BEB (F)-C | 13.0% |
| 2-HHB (F)-C | 15.0% |
| 3-HHB (F)-C | 15.0% |
| 3-HB (F) TB-2 | 4.0% |
| 3-HB (F) TB-3 | 4.0% |
| 3-HB (F) TB-4 | 4.0% |
| 3-HHB-1 | 5.0% |
| 3-HHB-O1 | 4.0% |
| $T_{NI}$ = 89.0 (°C.) | |
| η = 86.0 (mPa · s) | |
| Δn = 0.147 | |
| Δε = 30.8 | |
| $V_{th}$ = 0.86 (V) | |

Use Example 6

| | |
|---|---|
| V-H4H-2 (Compound No. 2) | 5.0% |
| V-H4H-3 (Compound No. 3) | 5.0% |
| 5-PyB-F | 4.0% |
| 3-PyB (F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 4.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |

|  |  |
|---|---|
| 3-H2BTB-4 | 5.0% |

$T_{NI} = 87.6$ (°C.)
$\eta = 30.2$ (mPa · s)
$\Delta n = 0.192$
$\Delta\epsilon = 6.0$
$V_{th} = 2.35$ (V)

Use Example 7

|  |  |
|---|---|
| V-H4H-3 (Compound No. 3) | 4.0% |
| 3-DB-C | 10.0% |
| 4-DB-C | 10.0% |
| 2-BEB-C | 12.0% |
| 3-BEB-C | 4.0% |
| 3-PyB (F)-F | 6.0% |
| 3-HEB-04 | 4.0% |
| 4-HEB-02 | 6.0% |
| 5-HEB-01 | 6.0% |
| 3-HEB-02 | 5.0% |
| 5-HEB-02 | 4.0% |
| 5-HEB-5 | 5.0% |
| 4-HEB-5 | 5.0% |
| 10-BEB-2 | 4.0% |
| 3-HHB-1 | 6.0% |
| 3-HHEBB-C | 3.0% |
| 3-HBEBB-C | 3.0% |
| 5-HBEBB-C | 3.0% |

$T_{NI} = 68.4$ (°C.)
$\eta = 37.9$ (mPa · s)
$\Delta n = 0.119$
$\Delta\epsilon = 11.4$
$V_{th} = 1.31$ (V)

Use Example 8

|  |  |
|---|---|
| V-H4H-3 (Compound No. 3) | 5.0% |
| V-H4H-5 (Compound No. 5) | 2.0% |
| 3-HB-C | 18.0% |
| 7-HB-C | 3.0% |
| 101-HB-C | 10.0% |
| 3-HB (F)-C | 10.0% |
| 2-PyB-2 | 2.0% |
| 3-PyB-2 | 2.0% |
| 4-PyB-2 | 2.0% |
| 101-HH-3 | 3.0% |
| 2-BTB-01 | 7.0% |
| 3-HHB-1 | 7.0% |
| 3-HHB-F | 4.0% |
| 3-HHB-01 | 4.0% |
| 3-HHB-3 | 5.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

$T_{NI} = 76.2$ (°C.)
$\eta = 16.9$ (mPa · s)
$\Delta n = 0.137$
$\Delta\epsilon = 7.9$
$V_{th} = 1.77$ (V)

Use Example 9

|  |  |
|---|---|
| V-H4H-3 (Compound No. 3) | 5.0% |
| 201-BEB (F)-C | 5.0% |
| 301-BEB (F)-C | 12.0% |
| 501-BEB (F)-C | 4.0% |
| 1V2-BEB (F, F)-C | 10.0% |
| 3-HH-EMe | 5.0% |
| 3-HB-02 | 15.0% |
| 7-HEB-F | 3.0% |
| 3-HHEB-F | 3.0% |
| 5-HHEB-F | 3.0% |
| 3-HBEB-F | 4.0% |
| 201-HBEB (F)-C | 2.0% |
| 3-HBEB (F, F)-C | 4.0% |
| 3-HHB-F | 4.0% |
| 3-HHB-01 | 4.0% |
| 3-HHB-3 | 13.0% |
| 3-HEBEB-F | 2.0% |
| 3-HEBEB-1 | 2.0% |

$T_{NI} = 73.9$ (°C.)
$\eta = 34.1$ (mPa · s)
$\Delta n = 0.107$
$\Delta\epsilon = 23.4$
$V_{th} = 0.99$ (V)

Use Example 10

|  |  |
|---|---|
| V-H4H-2 (Compound No. 2) | 4.0% |
| 201-BEB (F)-C | 5.0% |
| 301-BEB (F)-C | 12.0% |
| 501-BEB (F)-C | 4.0% |
| 1V2-BEB (F, F)-C | 16.0% |
| 3-HB-02 | 6.0% |
| 3-HH-4 | 3.0% |
| 3-HHB-F | 3.0% |
| 3-HHB-1 | 8.0% |
| 3-HHB-01 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB (F) TB-2 | 5.0% |

$T_{NI} = 90.1$ (°C.)
$\eta = 40.6$ (mPa · s)
$\Delta n = 0.142$
$\Delta\epsilon = 28.1$
$V_{th} = 1.00$ (V)

Use Example 11

|  |  |
|---|---|
| V-H4H-2 (Compound No. 2) | 5.0% |
| V-H4H-3 (Compound No. 3) | 4.0% |
| V-H4H-5 (Compound No. 5) | 3.0% |
| 2-BEB-C | 12.0% |
| 3-BEB-C | 4.0% |
| 4-BEB-C | 6.0% |
| 3-HB-C | 28.0% |
| 3-HEB-04 | 5.0% |
| 4-HEB-02 | 4.0% |
| 5-HEB-01 | 4.0% |
| 3-HEB-02 | 6.0% |
| 5-HEB-02 | 5.0% |
| 3-HHB-1 | 10.0% |
| 3-HHB-01 | 4.0% |

$T_{NI} = 61.2$ (°C.)
$\eta = 22.7$ (mPa · s)
$\Delta n = 0.108$
$\Delta\epsilon = 9.8$
$V_{th} = 1.36$ (V)

Use Example 12

|  |  |
|---|---|
| V-H4H-3 (Compound No. 3) | 5.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 10-BEB-2 | 5.0% |
| 10-BEB-5 | 12.0% |
| 2-HHB-1 | 4.0% |
| 3-HHB-F | 4.0% |

-continued

| | |
|---|---|
| 3-HHB-1 | 7.0% |
| 3-HHB-O1 | 4.0% |
| 3-HHB-3 | 13.0% |

$T_{NI} = 66.9$ (°C.)
$\eta = 17.8$ (mPa · s)
$\Delta n = 0.156$
$\Delta \epsilon = 5.9$
$V_{th} = 1.87$ (V)
[0193]

Use Example 13

| | |
|---|---|
| V-H4H-3 (Compound No. 3) | 4.0% |
| 3-HB (F)-C | 5.0% |
| 201-BEB (F)-C | 5.0% |
| 301-BEB (F)-C | 10.0% |
| V-HB-C | 10.0% |
| 1V-HB-C | 10.0% |
| 2-BTB-O1 | 8.0% |
| 3-HB-O2 | 8.0% |
| V2-HH-3 | 5.0% |
| V-HH-4 | 5.0% |
| V-HHB-1 | 10.0% |
| 1V2-HBB-2 | 10.0% |
| 3-HHB-1 | 10.0% |

$T_{NI} = 65.3$ (°C.)
$\eta = 17.2$ (mPa · s)
$\Delta n = 0.126$
$\Delta \epsilon = 9.4$
$V_{th} = 1.47$ (V)

Use Example 14

| | |
|---|---|
| V-H4H-2 (Compound No. 2) | 5.0% |
| V-H4H-3 (Compound No. 3) | 5.0% |
| V-H4H-5 (Compound No. 5) | 3.0% |
| 2-HHB (F)-F | 15.0% |
| 3-HHB (F)-F | 15.0% |
| 5-HHB (F)-F | 15.0% |
| 2-H2HB (F)-F | 8.8% |
| 3-H2HB (F)-F | 4.4% |
| 5-H2HB (F)-F | 8.8% |
| 2-HBB (F)-F | 5.0% |
| 3-HBB (F)-F | 5.0% |
| 5-HBB (F)-F | 10.0% |

$T_{NI} = 89.4$ (°C.)
$\eta = 21.3$ (mPa · s)
$\Delta n = 0.083$
$\Delta \epsilon = 4.4$
$V_{th} = 2.37$ (V)

Use Example 15

| | |
|---|---|
| V-H4H-2 (Compound No. 2) | 6.0% |
| 7-HB (F)-F | 5.0% |
| 5-H2B (F)-F | 5.0% |
| 3-HH-4 | 2.0% |
| 3-HB-O2 | 7.0% |
| 2-HHB (F)-F | 10.0% |
| 3-HHB (F)-F | 10.0% |
| 5-HHB (F)-F | 10.0% |
| 3-H2HB (F)-F | 5.0% |
| 2-HBB (F)-F | 3.0% |
| 3-HBB (F)-F | 3.0% |
| 5-HBB (F)-F | 6.0% |
| 2-H2BB (F)-F | 5.0% |
| 3-H2BB (F)-F | 6.0% |
| 3-HHB-1 | 8.0% |
| 3-HHB-O1 | 5.0% |
| 3-HHB-3 | 4.0% |

$T_{NI} = 86.3$ (°C.)
$\eta = 18.9$ (mPa · s)
$\Delta n = 0.091$

-continued $\Delta \epsilon = 3.2$
$V_{th} = 2.69$ (V)

Use Example 16

| | |
|---|---|
| V—H4H-5 (Compound No. 5) | 3.0% |
| 7-HB(F,F)—F | 3.0% |
| 3-HB—O2 | 4.0% |
| 2-HHB(F)—F | 10.0% |
| 3-HHB(F)—F | 10.0% |
| 5-HHB(F)—F | 10.0% |
| 2-HBB(F)—F | 9.0% |
| 3-HBB(F)—F | 9.0% |
| 5-HBB(F)—F | 16.0% |
| 2-HBB—F | 4.0% |
| 3-HBB—F | 4.0% |
| 5-HBB—F | 3.0% |
| 3-HBB(F,F)—F | 5.0% |
| 5-HBB(F,F)—F | 10.0% |

$T_{NI} = 85.8$ (°C.)
$\eta = 25.1$ (mPa · s)
$\Delta n = 0.115$
$\Delta \epsilon = 5.6$
$V_{th} = 2.03$ (V)

Use Example 17

| | |
|---|---|
| V—H4H-3 (Compound No. 3) | 5.0% |
| 7-HB(F,F)—F | 4.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 5.0% |
| 4-HHB(F,F)—F | 5.0% |
| 3-HH2B(F,F)—F | 15.0% |
| 5-HH2B(F,F)—F | 10.0% |
| 3-HBB(F,F)—F | 12.0% |
| 5-HBB(F,F)—F | 12.0% |

$T_{NI} = 70.9$ (°C.)
$\eta = 25.7$ (mPa · s)
$\Delta n = 0.083$
$\Delta \epsilon = 8.1$
$V_{th} = 1.63$ (V)

Use Example 18

| | |
|---|---|
| V—H4H-3 (Compound No. 3) | 3.0% |
| 3-HB—CL | 10.0% |
| 5-HB—CL | 4.0% |
| 7-HB—CL | 4.0% |
| 1O1-HH-5 | 2.0% |
| 2-HBB(F)—F | 8.0% |
| 3-HBB(F)—F | 8.0% |
| 5-HBB(F)—F | 14.0% |
| 4-HHB—CL | 8.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 4.0% |
| 3-HB(F)VB-3 | 4.0% |

$T_{NI} = 90.8$ (°C.)
$\eta = 20.5$ (mPa · s)
$\Delta n = 0.129$
$\Delta \epsilon = 4.9$
$V_{th} = 2.32$ (V)

Use Example 19

| | |
|---|---|
| V—H4H-2 (Compound No. 2) | 4.0% |
| 3-HHB(F,F)—F | 7.0% |
| 3-H2HB(F,F)—F | 8.0% |
| 4-H2HB(F,F)—F | 8.0% |
| 5-H2HB(F,F)—F | 8.0% |
| 3-HBB(F,F)—F | 21.0% |
| 5-HBB(F,F)—F | 20.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 1O1-HBBH-4 | 2.0% |
| 1O1-HBBH-5 | 4.0% |
| $T_{NI}$ = 91.6 (°C.) | |
| η = 33.2 (mPa · s) | |
| Δn = 0.112 | |
| Δε = 8.7 | |
| $V_{th}$ = 1.79 (V) | |

Use Example 20

| | |
|---|---|
| V—H4H-2 (Compound No. 2) | 5.0% |
| V—H4H-3 (Compound No. 3) | 5.0% |
| 5-HB—F | 5.0% |
| 6-HB—F | 6.0% |
| 7-HB—F | 7.0% |
| 2-HHB—OCF3 | 7.0% |
| 3-HHB—OCF3 | 11.0% |
| 4-HHB—OCF3 | 7.0% |
| 5-HHB—OCF3 | 5.0% |
| 3-HH2B—OCF3 | 4.0% |
| 5-HH2B—OCF3 | 4.0% |
| 3-HHB(F,F)—OCF3 | 5.0% |
| 3-HBB(F)—F | 10.0% |
| 5-HBB(F)—F | 10.0% |
| 3-HH2B(F)—F | 3.0% |
| 3-HB(F)BH-3 | 3.0% |
| 5-HBBH-3 | 3.0% |
| $T_{NI}$ = 91.2 (°C.) | |
| η = 15.8 (mPa · s) | |
| Δn = 0.093 | |
| Δε = 4.4 | |
| $V_{th}$ = 2.43 (V) | |

Use Example 21

| | |
|---|---|
| V—H4H-3 (Compound No. 3) | 3.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 1O1-HBBH-4 | 2.0% |
| 1O1-HBBH-5 | 5.0% |
| $T_{NI}$ = 89.7 (°C.) | |
| η = 32.8 (mPa · s) | |
| Δn = 0.132 | |
| Δε = 7.2 | |
| $V_{th}$ = 1.92 (V) | |

Use Example 22

| | |
|---|---|
| V—H4H-2 (Compound No. 2) | 2.0% |
| V—H4H-5 (Compound No. 5) | 2.0% |
| 3-H2HB(F,F)—F | 6.0% |
| 4-H2HB(F,F)—F | 5.0% |

-continued

| | |
|---|---|
| 5-H2HB(F,F)—F | 5.0% |
| 3-HH2B(F,F)—F | 5.0% |
| 3-HBB(F,F)—F | 20.0% |
| 5-HBB(F,F)—F | 23.0% |
| 3-HBEB(F,F)—F | 4.0% |
| 4-HBEB(F,F)—F | 2.0% |
| 5-HBEB(F,F)—F | 2.0% |
| 3-HHEB(F,F)—F | 15.0% |
| 4-HHEB(F,F)—F | 4.0% |
| 5-HHEB(F,F)—F | 5.0% |
| $T_{NI}$ = 73.2 (°C.) | |
| η = 32.4 (mPa · s) | |
| Δn = 0.097 | |
| Δε = 11.1 | |
| $V_{th}$ = 1.35 (V) | |

What is claimed is:

1. An alkenylcyclohexane derivative expressed by the formula (1):

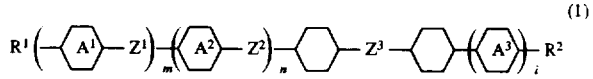

(1)

wherein $R^1$ and $R^2$ represent a linear or branched alkyl group of 1 to 15 carbon atoms or alkenyl group of 2 to 15 carbon atoms; at least one of $R^1$ and $R^2$ represents an alkenyl group; in these groups, one or more non-adjacent $CH_2$ groups may be replaced by oxygen atom, sulfur atom or —C≡C— group; ring $A^1$, ring $A^2$ and ring $A^3$ each independently represent 1,4-cyclohexylene group wherein one or more $CH_2$ groups in the ring may be replaced by oxygen atom or sulfur atom, or 1,4-phenylene group wherein one or more CH groups in the ring may be replaced by nitrogen atom; $Z^1$ and $Z^2$ each independently represent —$CH_2CH_2$—, —$CH_2O$—, —$OCH_2$—, —CH=CH—, —C≡C— or single bond; $Z^3$ represents —$(CH_2)_4$—, —CH=CH—$(CH_2)_2$—, —$CH_2$—CH=CH—$CH_2$— or —$(CH_2)_2$—CH=CH—; and m, n and i each independently represent 0 or 1, provided that when m and n represent 0, and i represents 1, and $Z^3$ represents —$(CH_2)_4$—, and ring $A^3$ represents 1,4-phenylene group; then $R^1$ represents a linear or branched alkenyl group of 2 to 15 carbon atoms, and $R^2$ represents a group other than methoxy;

when m represents 1, and n and i represent 0, and $Z^1$ represents single bond, and $Z^3$ represents —$(CH_2)_4$—, and ring $A^1$ represents 1,4—phenylene group; then $R^1$ represents a group other than methoxy, and $R^2$ represents a linear or branched alkenyl group of 2 to 15 carbon atoms; and when m represents 0, and n represents 1, and i represents 0, and $Z^2$ represents a single bond, and $Z^3$ represents —$(CH_2)_4$—, and ring $A^2$ represents 1,4-phenylene group; then $R^1$ represents a group other than methoxy, and $R^2$ represents a linear or branched alkenyl group of 2 to 15 carbon atoms.

2. A compound according to claim 1, wherein m=n=i=0 in the formula (1).

3. A compound according to claim 2, wherein, in the formula (1), $R^1$ represents an alkyl group, $R^2$ represents an alkenyl group, and $Z^3$ represents —$(CH_2)_4$—.

4. A compound according to claim 2, wherein, in the formula (1), $R^1$ represents an alkyl group, $R^2$ represents an alkenyl group and $Z^3$ represents —CH=CH—$(CH_2)_2$— or —$(CH_2)_2$—CH=CH—.

5. A compound according to claim 1, wherein in the formula (1), m=1 and n=i=0.

6. A compound according to claim 5, wherein, in the formula (1), $R^1$ represents an alkyl group, $R^2$ represents an alkenyl group and $Z^3$ represents —$(CH_2)_4$—.

7. A compound according to claim 5, wherein, in the formula (1), $R^1$ represents an alkyl group, $R^2$ represents an alkenyl group and $Z^3$ represents —CH=CH—(CH$_2$)$_2$— or —(CH$_2$)$_2$—CH=CH—.

8. A compound according to claim 1, wherein, in the formula (1), m=n=1 and i=0.

9. A compound according to claim 8, wherein, in the formula (1), $R^1$ represents an alkyl group, $R^2$ represents an alkenyl group and $Z^3$ represents —(CH$_2$)$_4$—.

10. A compound according to claim 8, wherein, in the formula (1), $R^1$ represents an alkyl group, $R^2$ represents an alkenyl group, and $Z^3$ represents —CH=CH—(CH$_2$)$_2$— or —(CH$_2$)$_2$—CH=CH—.

11. A liquid crystal composition consisting of at least two components, one or more of which is at least one compound expressed by the formula (1) set forth in claim 1.

12. A liquid crystal composition which comprises as a first component, at least one alkenylcyclohexane derivative according to any one of claims 1 to 10, and as a second component, at least one compound selected from the group consisting of the formulas (2), (3) and (4),

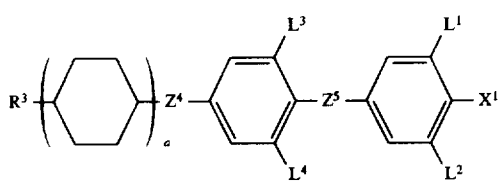

wherein $R^3$ represents an alkyl group of 1 to 10 carbon atoms; $X^1$ represents F, Cl, OCF$_3$, OCF$_2$H, CF$_3$, CF$_2$H or CFH$_2$; $L^1$, $L^2$, $L^3$ and $L^4$ each independently represent H or F; $Z^4$ and $Z^5$ each independently represent —(CH$_2$)$_2$—, —CH=CH— or single bond; and a represents 1 or 2.

13. A liquid crystal composition which comprises as a first component, at least one alkenylcyclohexane derivative according to any one of claims 1 to 10, and as a second component, at least one compound selected from the group consisting of the formulas (5), (6), (7), (8) and (9).

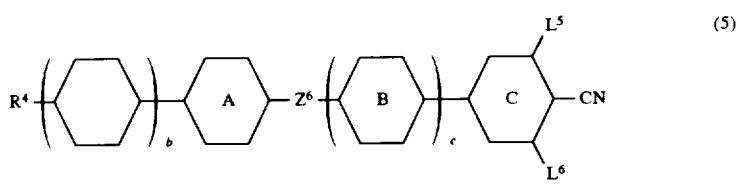 (5)

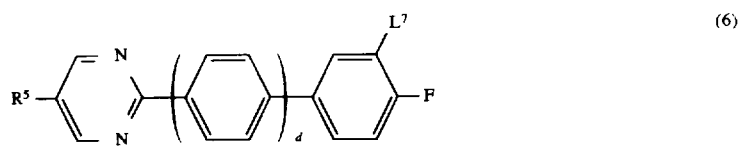 (6)

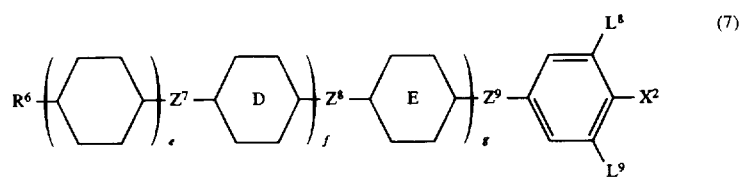 (7)

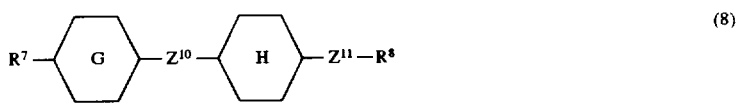 (8)

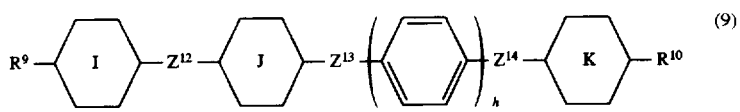 (9)

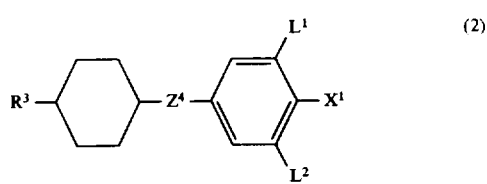 (2)

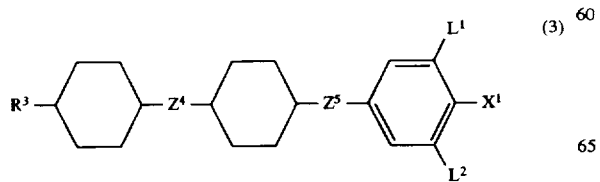 (3)

wherein $R^4$ represents fluorine atom (F), an alkyl group of 1 to 10 carbon atoms or an alkenyl group of 2 to 10 carbon atoms; in these groups, optional methylene groups (—CH$_2$—) may be replaced by oxygen atom (—O—), but two or more adjacent methylene groups are not continuously replaced by oxygen atom; ring A represents trans-1,4-cyclohexylene group, 1,4-phenylene group, pyrimidine-2,5-diyl group or 1,3-dioxane-2,5-diyl group; ring B represents trans-1,4-cyclohexylene group, 1,4-phenylene group or pyrimidine-2,5-diyl group; ring C represents trans-1,4-cyclohexylene group or 1,4-phenylene group; $Z^6$ represents —(CH$_2$)$_2$—, —COO— or single bond; $L^5$ and $L^6$ each independently represent H or F; and b and c each independently represent 0 or 1;

$R^5$ represents an alkyl group of 1 to 10 carbon atoms; $L^7$ represents H or F; and d represents 0 or 1;

$R^6$ represents an alkyl group of 1 to 10 carbon atoms; ring D and ring E each independently represent trans-1,4-cyclohexylene group or 1,4-phenylene group; $Z^7$ and $Z^8$ each independently represent —COO— or single bond; $Z^9$ represents —COO— or —C≡C—; $L^8$ and $L^9$ each independently represent H or F; $X^2$ represents F, $OCF_3$, $OCF_2H$, $CF_3$, $CF_2H$ or $CFH_2$, but when $X^2$ represents $OCF_3$, $OCF_2H$, $CF_3$, $CF_2H$ or $CFH_2$, $L^8$ and $L^9$ both represent H; e, f and g each independently represent 0 or 1;

$R^7$ and $R^8$ each independently represent an alkyl group of 1 to 10 carbon atoms or an alkenyl group of 2 to 10 carbon atoms, and optional methylene groups (—$CH_2$—) among them may be replaced by oxygen atom (—O—), but two or more methylene groups are not continuously replaced by oxygen atom; ring G represents trans-1,4-cyclohexylene group, 1,4-phenylene group or pyrimidine-2,5-diyl; ring H represents trans-1,4-cyclohexylene group or 1,4-phenylene group; $Z^{10}$ represents —C≡C—, —COO—, —($CH_2$)$_2$—, —CH=CH—C≡C— or single bond; $Z^{11}$ represents —COO— or single bond;

$R^9$ and $R^{10}$ each independently represent an alkyl group of 1 to 10 carbon atoms or an alkenyl group of 2 to 10 carbon atoms, and optional methylene groups (—$CH_2$—) among them may be replaced by oxygen atom (—O—), but two or more methylene groups are not continuously replaced by oxygen atom; ring I represents trans-1,4-cyclohexylene group, 1,4-phenylene group or pyrimidine-2,5-diyl group; ring J represents trans-1,4-cyclohexylene group, 1,4-phenylene group wherein one or more hydrogen atoms on the ring may be replaced by F, or pyrimidine-2,5-diyl group; ring K represents trans-1,4-cyclohexylene group or 1,4-phenylene group; $Z^{12}$ and $Z^{14}$ each independently represent —COO—, —($CH_2$)$_2$— or single bond; $Z^{13}$ represents —CH=CH—, —C≡C—, —COO— or single bond; and h represents 0 or 1.

14. A liquid crystal display element comprising a liquid crystal composition according to claim 11.

15. A liquid crystal composition which comprises as a first component, at least one alkenylcyclohexane derivative according to any one of claims 1 to 10, and as a part of a second component, at least one compound selected from the group consisting of the formulas (2), (3) and (4),

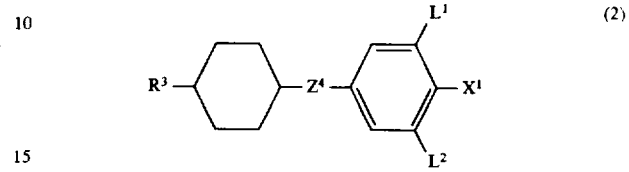
(2)

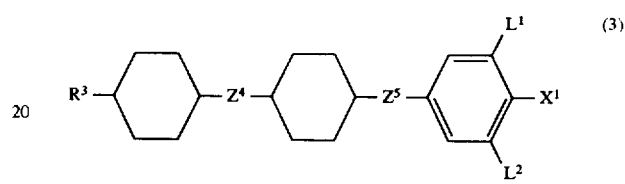
(3)

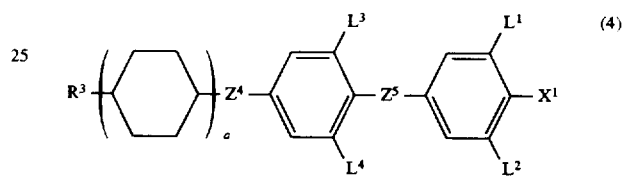
(4)

wherein $R^3$ represents an alkyl group of 1 to 10 carbon atoms; $X^1$ represents F, Cl, $OCF_3$, $OCF_2H$, $CF_3$, $CF_2H$ or $CFH_2$; $L^1$, $L^2$, $L^3$ and $L^4$ each independently represent H or F; $Z^4$ and $Z^5$ each independently represent —($CH_2$)$_2$—, —CH=CH— or single bond; and a represents 1 or 2, and further as another part of the second component, at least one compound selected from the group consisting of the formulas (5), (6), (7), (8) and (9)

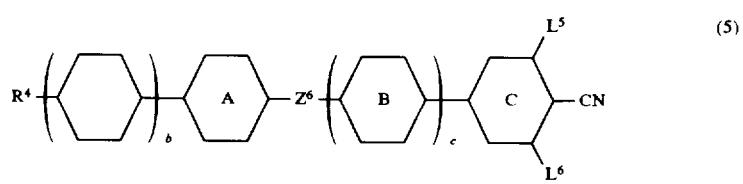
(5)

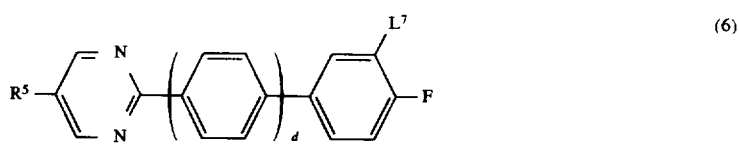
(6)

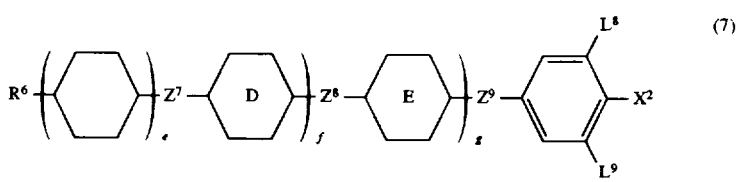
(7)

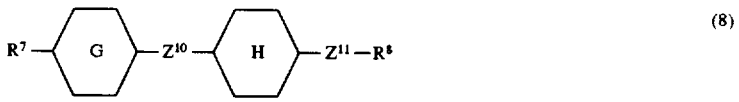
(8)

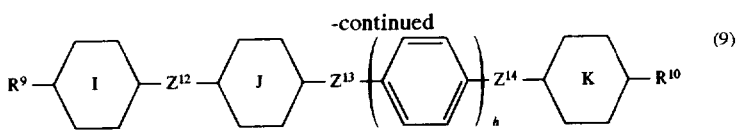

wherein R⁴ represents fluorine atom (F), an alkyl group of 1 to 10 carbon atoms or an alkenyl group of 2 to 10 carbon atoms; in these groups, optional methylene groups (—CH₂—) may be replaced by oxygen atom (—O—), but two or more adjacent methylene groups are not continuously replaced by oxygen atom; ring A represents trans-1,4-cyclohexylene group, 1,4-phenylene group, pyrimidine-2,5-diyl group or 1,3-dioxane-2,5-diyl group; ring B represents trans-1,4-cyclohexylene group, 1,4-phenylene group or pyrimidine-2,5-diyl group; ring C represents trans-1,4-cyclohexylene group or 1,4-phenylene group; $Z^6$ represents —(CH₂)₂—, —COO— or single bond; $L^5$ and $L^6$ each independently represent H or F; and b and c each independently represent 0 or 1;

$R^5$ represents an alkyl group of 1 to 10 carbon atoms; $L^7$ represents H or F; and d represents 0 or 1;

$R^6$ represents an alkyl group of 1 to 10 carbon atoms; ring D and ring E each independently represent trans-1,4-cyclohexylene group or 1,4-phenylene group; $Z^7$ and $Z^8$ each independently represent —COO— or single bond; $Z^9$ represents —COO— or —C≡C—; $L^8$ and $L^9$ each independently represent H or F; $X^2$ represents F, OCF₃, OCF₂H, CF₃, CF₂H or CFH₂, but when $X^2$ represents OCF₃, OCF₂H, CF₃, CF₂H or CFH₂, $L^8$ and $L^9$ both represent H; e, f and g each independently represent 0 or 1;

$R^7$ and $R^8$ each independently represent an alkyl group of 1 to 10 carbon atoms or an alkenyl group of 2 to 10 carbon atoms, and in either, optional methylene groups (—CH₂—) among them may be replaced by oxygen atom (—O—), but two or more methylene groups are not continuously replaced by oxygen atom; ring G represents trans-1,4-cyclohexylene group, 1,4-phenylene group or pyrimidine-2,5-diyl; ring H represents trans-1,4-cyclohexylene group or 1,4-phenylene group; $Z^{10}$ represents —C≡C—, —COO—, —(CH₂)₂—, —CH=CH—C≡C— or single bond; $Z^{11}$ represents —COO— or single bond;

$R^9$ and $R^{10}$ each independently represent an alkyl group of 1 to 10 carbon atoms or an alkenyl group of 2 to 10 carbon atoms, and in either, optional methylene groups (—CH₂—) among them may be replaced by oxygen atom (—O—), but two or more methylene groups are not continuously replaced by oxygen atom; ring I represents trans-1,4-cyclohexylene group, 1,4-phenylene group or pyrimidine-2,5-diyl group; ring J represents trans-1,4-cyclohexylene group, 1,4-phenylene group wherein one or more hydrogen atoms on the ring may be replaced by F, or pyrimidine-2,5-diyl group; ring K represents trans-1,4-cyclohexylene group or 1,4-phenylene group; $Z^{12}$ and $Z^{14}$ each independently represent —COO—, —(CH₂)₂— or single bond; $Z^{13}$ represents —CH=CH—, —C≡C—, —COO— or single bond; and h represents 0 or 1.

16. A liquid crystal display element comprising a liquid crystal composition according to claim 12.

17. A liquid crystal display element comprising a liquid crystal composition according to claim 13.

18. A liquid crystal display element comprising a liquid crystal composition according to claim 15.

* * * * *